US010870851B2

(12) United States Patent
Stampfer et al.

(10) Patent No.: US 10,870,851 B2
(45) Date of Patent: Dec. 22, 2020

(54) NON-CODING RNAS LINKED TO IMMORTALITY AND ASSOCIATED METHODS AND COMPOSITIONS

(71) Applicants: The Regents of the University of California, Oakland, CA (US); The Arizona Board of Regents on Behalf of the University of Arizona, Tucson, AZ (US)

(72) Inventors: Martha R. Stampfer, Oakland, CA (US); James C. Garbe, San Francisco, CA (US); Lukas Vrba, Tucson, AZ (US); Bernard W. Futscher, Tucson, AZ (US)

(73) Assignees: The Regents of the University of California, Oakland, CA (US); The Arizona Board of Regents on Behalf of the University of Arizona, Tucson, AZ (US)

( * ) Notice: Subject to any disclaimer, the term of this patent is extended or adjusted under 35 U.S.C. 154(b) by 0 days.

(21) Appl. No.: 15/764,255

(22) PCT Filed: Oct. 5, 2016

(86) PCT No.: PCT/US2016/055587
§ 371 (c)(1),
(2) Date: Mar. 28, 2018

(87) PCT Pub. No.: WO2017/062517
PCT Pub. Date: Apr. 13, 2017

(65) Prior Publication Data
US 2018/0298382 A1 Oct. 18, 2018

Related U.S. Application Data

(60) Provisional application No. 62/238,029, filed on Oct. 6, 2015.

(51) Int. Cl.
*C12N 15/113* (2010.01)
*C12N 5/09* (2010.01)
*C12N 15/79* (2006.01)
*C12N 15/88* (2006.01)

(52) U.S. Cl.
CPC ......... *C12N 15/113* (2013.01); *C12N 5/0693* (2013.01); *C12N 15/79* (2013.01); *C12N 15/88* (2013.01); *C12N 2310/111* (2013.01); *C12N 2310/113* (2013.01); *C12N 2310/14* (2013.01); *C12N 2510/04* (2013.01)

(58) Field of Classification Search
None
See application file for complete search history.

(56) References Cited

U.S. PATENT DOCUMENTS

| | | | |
|---|---|---|---|
| 2002/0045170 A1* | 4/2002 | Wong | C07K 14/47 435/6.16 |
| 2006/0286552 A1 | 12/2006 | Goldsmith et al. | |
| 2008/0280297 A1* | 11/2008 | Dalla-Favera | C07K 16/3061 435/6.16 |
| 2009/0269774 A1* | 10/2009 | Rothenberg | G01N 33/6893 435/6.11 |
| 2010/0234292 A1* | 9/2010 | Bertucci | C12Q 1/6886 514/19.4 |
| 2010/0280134 A1 | 11/2010 | Renard et al. | |
| 2012/0270317 A1 | 10/2012 | Harper et al. | |
| 2013/0011920 A1 | 1/2013 | Zhou et al. | |
| 2013/0252835 A1 | 9/2013 | Koh et al. | |
| 2017/0130232 A1* | 5/2017 | Stampfer | G01N 33/5014 |

FOREIGN PATENT DOCUMENTS

| | | |
|---|---|---|
| WO | 1998037181 | 8/1998 |
| WO | 2014020048 | 2/2014 |

OTHER PUBLICATIONS

Vrba et al. Epigenetics 10: 11, 1074-1083 (Year: 2015).*
Hrycyna et al. Methods in Enzymology 292, p. 456-473 (Year: 1998).*
Freimuth et al. (2004) "Human Cytosolic Sulfotransferase Database Mining: Identification of Seven Novel Genes and Pseudogenes" The Pharmacogenomics Journal, 4:54-65.

* cited by examiner

*Primary Examiner* — Brian Whiteman
(74) *Attorney, Agent, or Firm* — Brian E. Davy; Bozicevic, Field & Francis LLP

(57) ABSTRACT

Aspects of the present disclosure include RNAs that confer a mortal phenotype and nucleic acids encoding same. Liposomes, recombinant cells, and pharmaceutical compositions that include the RNAs or nucleic acids encoding same are also provided. Further provided are methods involving quantifying MORT RNAs and/or determining the methylation status of the MORT promoter, as well as methods that employ the RNAs or nucleic acids encoding same.

6 Claims, 43 Drawing Sheets
Specification includes a Sequence Listing.

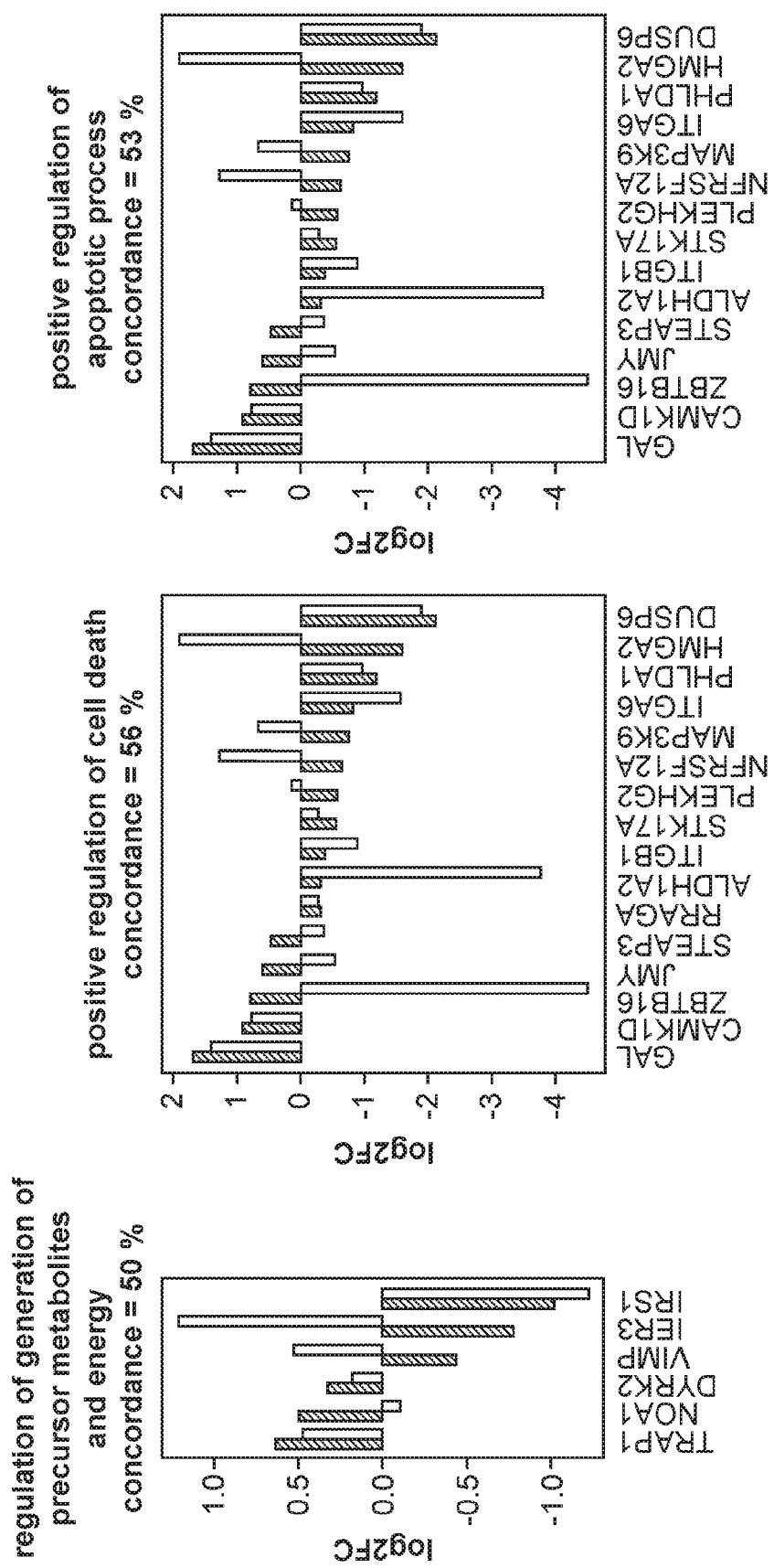
FIG. 3A (Cont. 1)

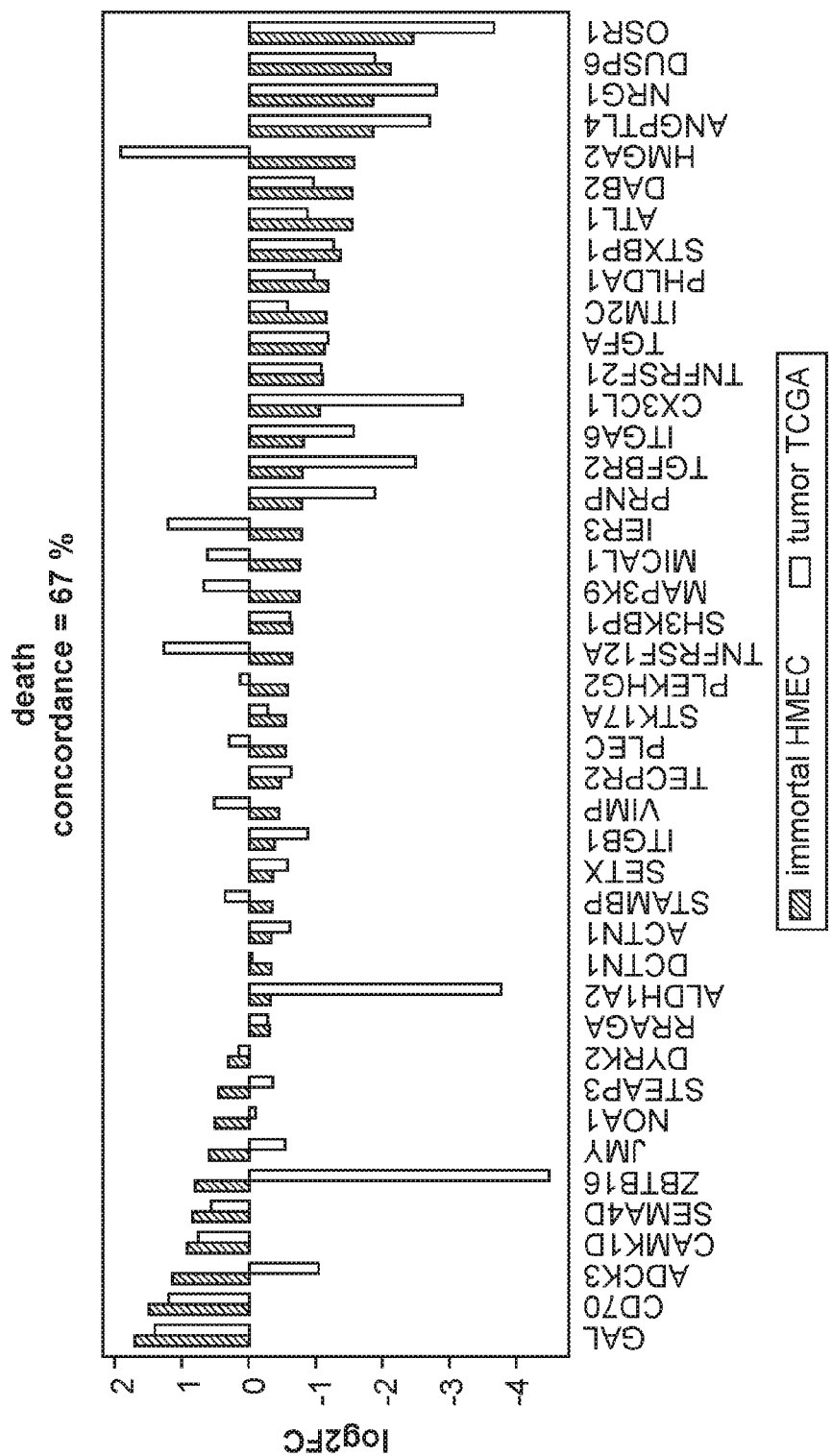
FIG. 3A (Cont. 2)

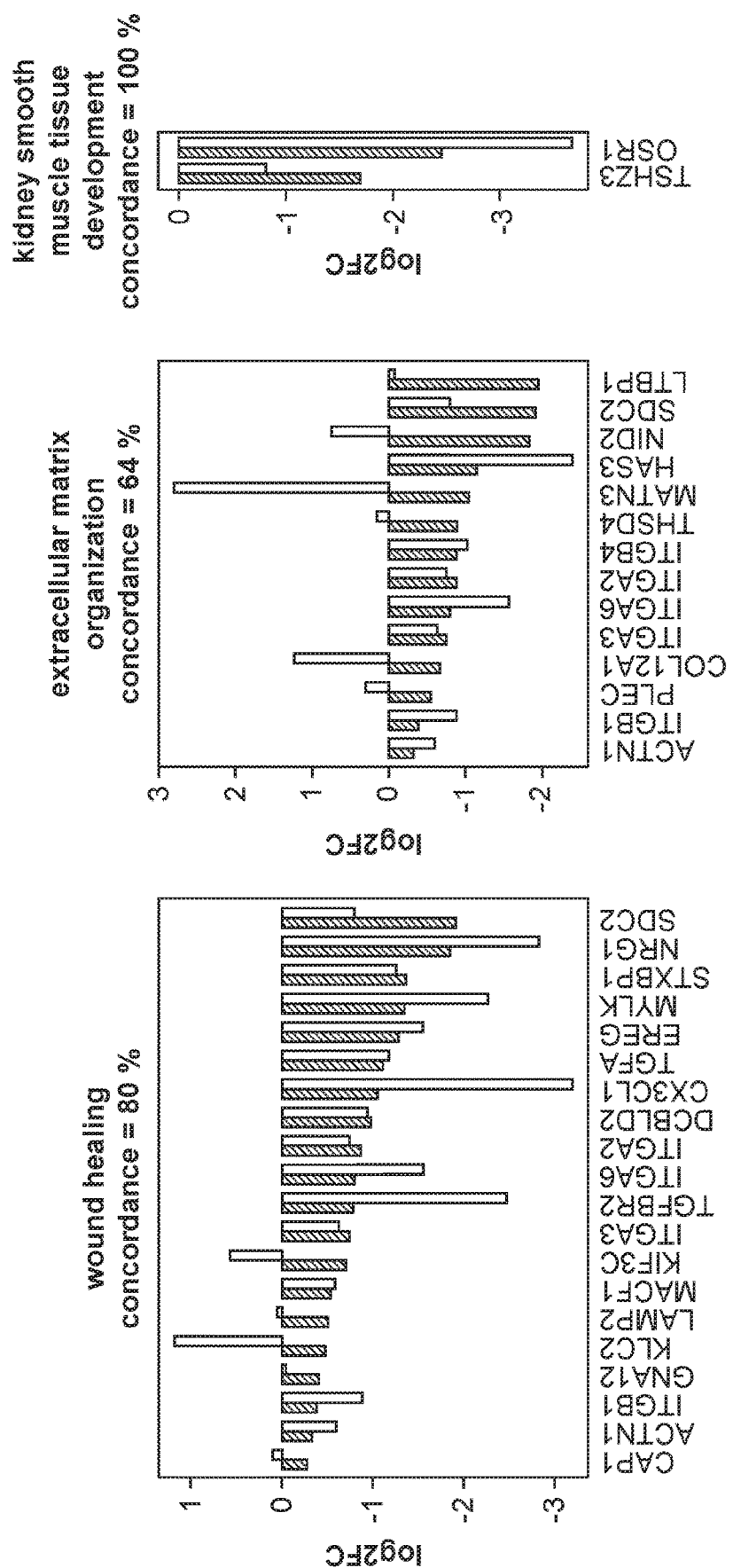
FIG. 3B (Cont. 1)

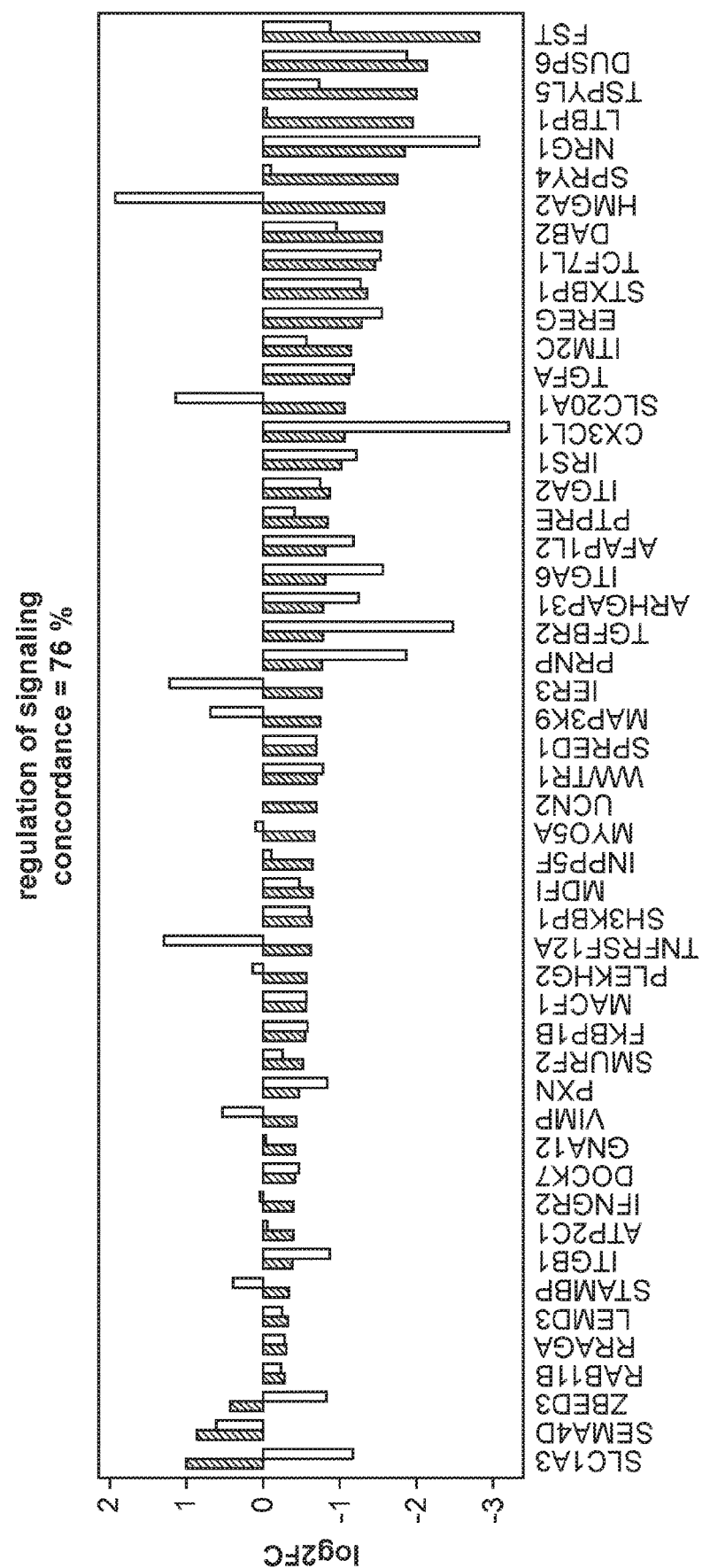
FIG. 3B (Cont. 2)

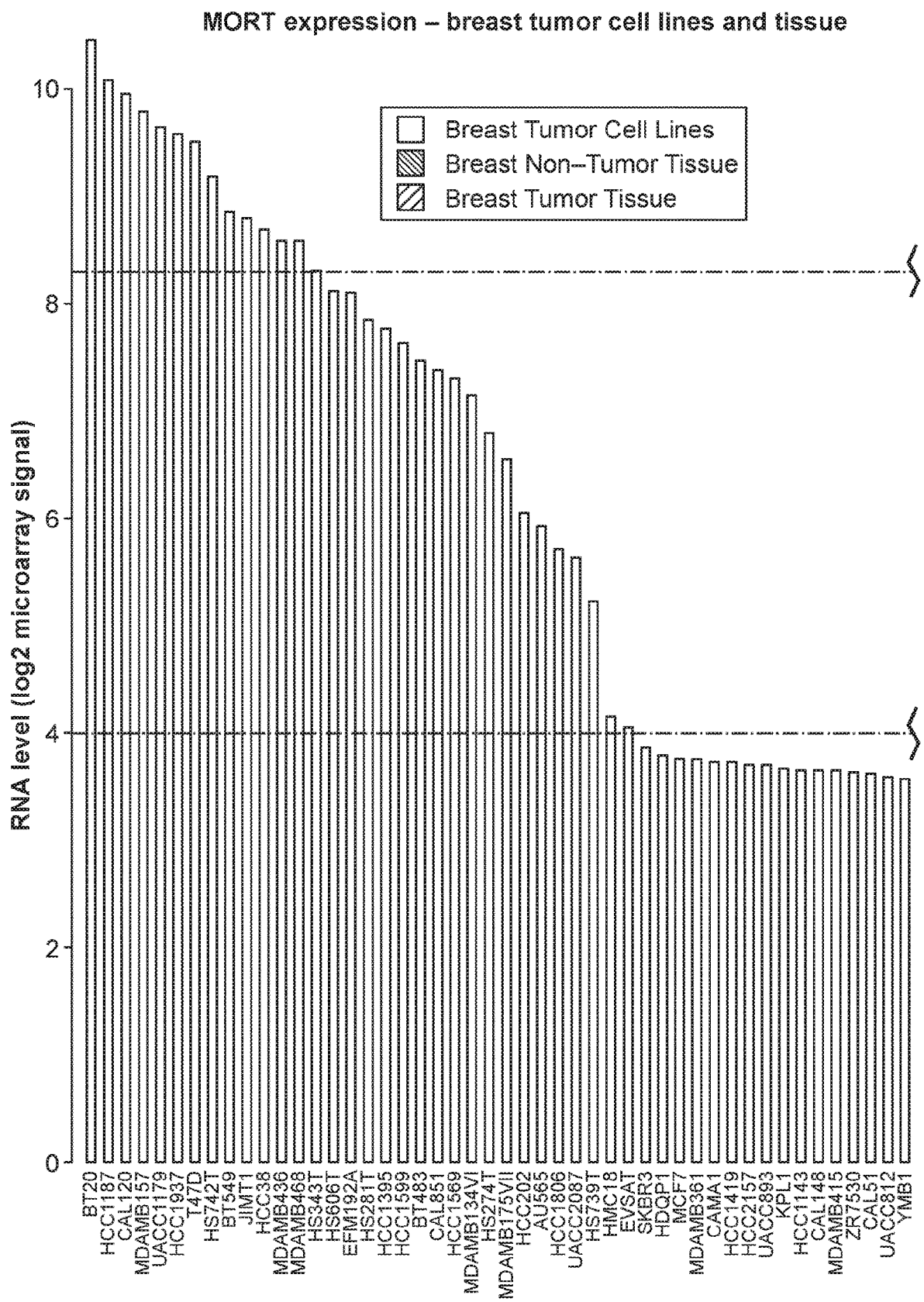
FIG. 9  *CCLE cell lines*

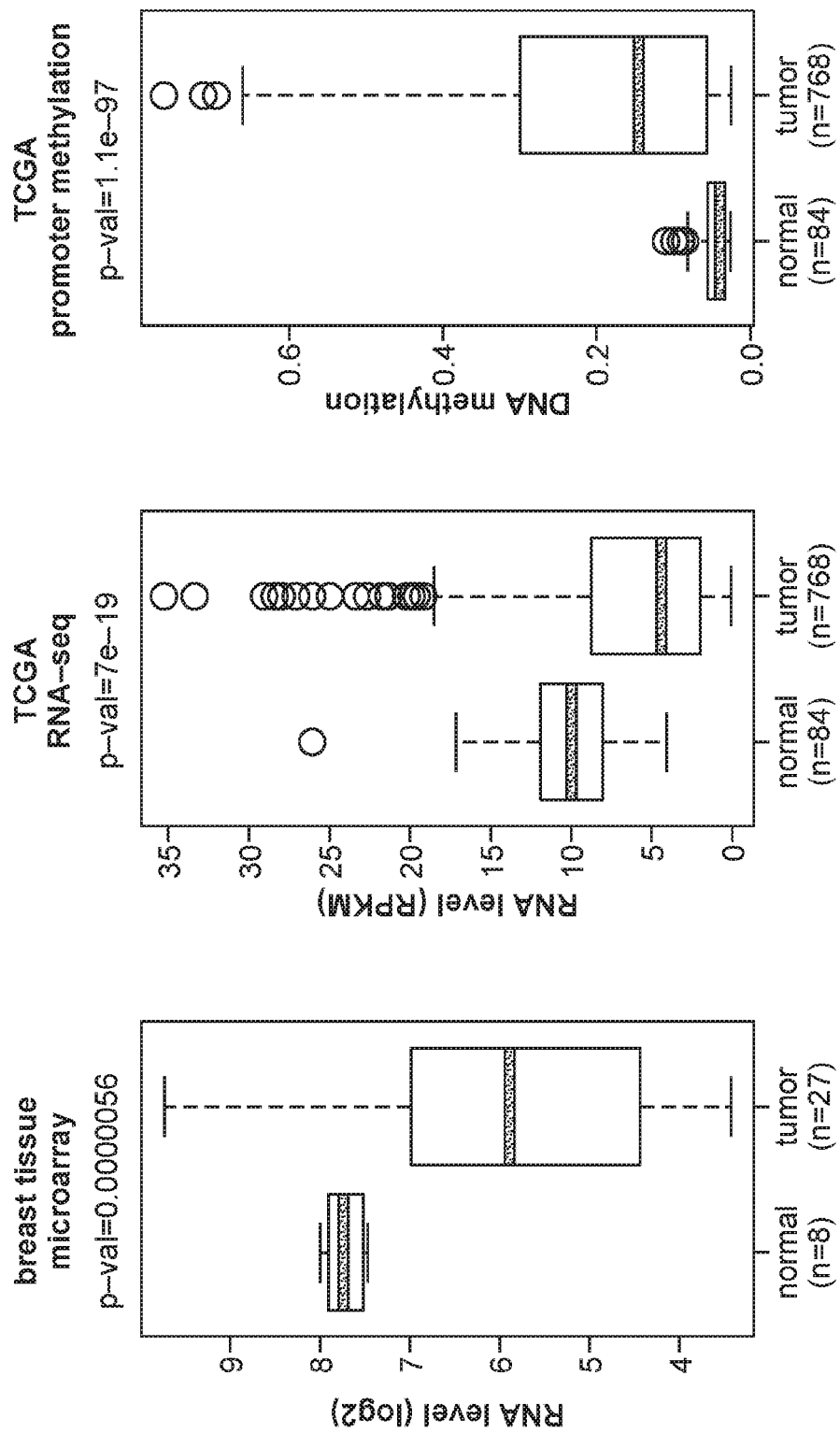

Genes with at least two fold mean expression change after the first genetic modification that led to by passing stasis.

| probe.set.ID | logFC | AveExpr | adj.P.Val | ACCNUM | SYMBOL |
|---|---|---|---|---|---|
| 8141374 | -2.212037439 | 7.710436018 | 0.999729896 | NM_001185 | AZGP1 |
| 8112428 | -2.101947105 | 6.388443225 | 0.999729896 | NM_005582 | CD180 |
| 8109926 | -1.939789606 | 10.28941087 | 0.999729896 | NM_014211 | GABRP |
| 7938608 | -1.931441488 | 6.370195536 | 0.999729896 | NM_006108 | SPON1 |
| 7947481 | -1.90285413 | 5.861400609 | 0.999729896 | NM_198381 | ELF5 |
| 7997139 | -1.893596417 | 7.368168361 | 0.999729896 | NM_001740 | CALB2 |
| 7951217 | -1.858801272 | 8.521212052 | 0.999729896 | NM_002423 | MMP7 |
| 8099476 | -1.853403013 | 7.557655579 | 0.999729896 | NM_006017 | PROM1 |
| 7969288 | -1.752922945 | 6.184364994 | 0.999729896 | NM_006418 | OLFM4 |
| 7930593 | -1.703062859 | 6.04630433 | 0.999729896 | NM_024889 | PLEKHS1 |
| 8178439 | -1.681045272 | 6.934848396 | 0.999729896 | NM_014070 | C6orf15 |
| 8124859 | -1.663367933 | 7.011884271 | 0.999729896 | NM_014070 | C6orf15 |
| 8097017 | -1.656060033 | 7.761837873 | 0.999729896 | NM_001128174 | UGT8 |
| 8109752 | -1.585339403 | 8.520954508 | 0.999729896 | AK302302 | ODZ2 |
| 8179713 | -1.579877011 | 6.85592452 | 0.999729896 | NM_014070 | C6orf15 |
| 8151369 | -1.561986428 | 8.217718314 | 0.999729896 | NM_153225 | SBSPON |
| 8077366 | -1.531976421 | 5.977153435 | 0.999729896 | NM_020873 | LRRN1 |
| 7968678 | -1.521211714 | 5.079057514 | 0.999729896 | NM_207361 | FREM2 |
| 8138888 | -1.51225359 | 6.305037918 | 0.999729896 | NM_005020 | PDE1C |
| 8070467 | -1.477870967 | 5.832141792 | 0.999729896 | NM_001135099 | TMPRSS2 |
| 7918936 | -1.444940546 | 8.145878055 | 0.999729896 | NM_024626 | VTCN1 |
| 7926334 | -1.433486324 | 6.622172377 | 0.999729896 | NM_018324 | OLAH |
| 8069795 | -1.42914793 | 6.633803765 | 0.999729896 | NM_199328 | CLDN8 |
| 8095110 | -1.396593844 | 5.222362528 | 0.999729896 | NM_000222 | KIT |
| 8135378 | -1.393735244 | 6.32244061 | 0.999729896 | NM_002736 | PRKAR2B |
| 8001800 | -1.374337921 | 6.405462967 | 0.999729896 | NM_001797 | CDH11 |
| 7961540 | -1.369675368 | 6.689768709 | 0.999729896 | NM_032918 | RERG |
| 8083978 | -1.342442921 | 6.260594922 | 0.999729896 | NM_207015 | NAALADL2 |
| 8023710 | -1.341333958 | 4.989013529 | 0.999729896 | NM_021153 | CDH19 |
| 7971461 | -1.338898195 | 9.4586604 | 0.999729896 | NM_002298 | LCP1 |
| 8096301 | -1.337923018 | 7.889030697 | 0.999729896 | NM_001040058 | SPP1 |
| 7934997 | -1.304719909 | 8.279706293 | 0.999729896 | NM_005398 | PPP1R3C |
| 8020724 | -1.29991834 | 5.830481632 | 0.999729896 | NM_001942 | DSG1 |
| 7932407 | -1.286597021 | 4.3189919 | 0.999729896 | NM_001004470 | ST8SIA6 |
| 8169504 | -1.284579757 | 9.445209626 | 0.999729896 | NM_007231 | SLC6A14 |
| 8094441 | -1.265600199 | 6.53027762 | 0.999729896 | NM_006424 | SLC34A2 |
| 8107798 | -1.258286258 | 7.091885276 | 0.999729896 | NM_001017372 | SLC27A6 |
| 8012896 | -1.249057909 | 8.920513572 | 0.999729896 | NM_000304 | PMP22 |

FIG. 15

| | | | | | |
|---|---|---|---|---|---|
| 8126153 | -1.241949777 | 6.555614921 | 0.999729896 | NM_003740 | KCNK5 |
| 8139488 | -1.240521251 | 8.647517846 | 0.999729896 | NM_001013398 | IGFBP3 |
| 7923547 | -1.198741132 | 6.946228404 | 0.999729896 | NM_001276 | CHI3L1 |
| 8098439 | -1.192905624 | 9.634830083 | 0.999729896 | NM_002354 | EPCAM |
| 7976496 | -1.187968647 | 11.54510679 | 0.999729896 | NM_001085 | SERPINA3 |
| 8115234 | -1.186374811 | 9.100152586 | 0.999729896 | NM_001155 | ANXA6 |
| 7912937 | -1.185123283 | 7.707539939 | 0.999729896 | NM_007365 | PADI2 |
| 8143221 | -1.179338461 | 6.844269088 | 0.999729896 | NM_020632 | ATP6V0A4 |
| 8067140 | -1.175571197 | 5.399046408 | 0.999729896 | NM_000782 | CYP24A1 |
| 8136709 | -1.173114233 | 6.038950618 | 0.999729896 | NR_003715 | LOC93432 |
| 8111932 | -1.172074292 | 8.569848154 | 0.999729896 | NM_148672 | CCL28 |
| 8100393 | -1.16958113 | 6.136396261 | 0.999729896 | NM_002253 | KDR |
| 8146957 | -1.155747246 | 7.526480355 | 0.999729896 | NM_015886 | PI15 |
| 8129573 | -1.141654518 | 6.667108528 | 0.999729896 | NM_015529 | MOXD1 |
| 8130867 | -1.132502663 | 7.404409752 | 0.999729896 | NM_003247 | THBS2 |
| 8134351 | -1.119928295 | 5.52326548 | 0.999729896 | NM_001166160 | PPP1R9A |
| 7950641 | -1.112271956 | 9.371530967 | 0.999729896 | NM_023930 | KCTD14 |
| 8042788 | -1.109461902 | 8.342537332 | 0.999729896 | NM_001615 | ACTG2 |
| 7936968 | -1.108758613 | 7.859559875 | 0.999729896 | NM_003474 | ADAM12 |
| 8091723 | -1.085908271 | 10.35975666 | 0.999729896 | NM_206963 | RARRES1 |
| 8099834 | -1.069865501 | 6.304042008 | 0.999729896 | NM_003263 | TLR1 |
| 8101788 | -1.068760675 | 8.080512446 | 0.999729896 | NM_003728 | UNC5C |
| 8138363 | -1.068457034 | 7.723016 | 0.999729896 | NM_015464 | SOSTDC1 |
| 7948354 | -1.057625869 | 7.454915783 | 0.999729896 | NM_145016 | GLYATL2 |
| 8029779 | -1.053749956 | 8.224270909 | 0.999729896 | NM_198541 | IGFL1 |
| 7920642 | -1.051937853 | 9.491610998 | 0.999729896 | NM_001018016 | MUC1 |
| 8150978 | -1.043523704 | 4.416269092 | 0.999729896 | NM_004056 | CA8 |
| 8174527 | -1.031428285 | 7.602411827 | 0.999729896 | NM_014289 | CAPN6 |
| 7947156 | -1.017892136 | 6.475125303 | 0.999729896 | NM_001135091 | MUC15 |
| 8092800 | -1.008502693 | 5.937687532 | 0.999729896 | NM_032279 | ATP13A4 |
| 8097957 | -1.008259418 | 8.573746754 | 0.999729896 | NM_000856 | GUCY1A3 |
| 8045882 | 1.016655849 | 7.865041476 | 0.999729896 | NM_001017920 | DAPL1 |
| 8158976 | 1.019131353 | 7.000842987 | 0.999729896 | NM_001807 | CEL |
| 8156360 | 1.020495814 | 5.947549963 | 0.999729896 | NR_026868 | ANKRD19P |
| 8054712 | 1.022489308 | 9.837148445 | 0.999729896 | NM_000575 | IL1A |
| 8126428 | 1.033461518 | 8.021825852 | 0.999729896 | NM_033502 | TRERF1 |
| 8136662 | 1.070037157 | 7.171466908 | 0.999729896 | NM_004668 | MGAM |
| 7933733 | 1.078583263 | 6.742884475 | 0.999729896 | NM_198215 | FAM13C |
| 8046020 | 1.084881553 | 6.780164129 | 0.999729896 | NM_021007 | SCN2A |

FIG. 15 (Cont. 1)

| | | | | | |
|---|---|---|---|---|---|
| 7905525 | 1.096338175 | 5.55882267 | 0.999729896 | NM_178349 | LCE1B |
| 7958884 | 1.106302642 | 8.287636132 | 0.999729896 | NM_016816 | OAS1 |
| 8111255 | 1.121604618 | 5.910068397 | 0.999729896 | NM_006727 | CDH10 |
| 7967117 | 1.124805881 | 6.982783761 | 0.999729896 | NM_003733 | OASL |
| 8014316 | 1.128121194 | 6.517588844 | 0.999729896 | NM_002985 | CCL5 |
| 7925320 | 1.132444844 | 7.787556016 | 0.999729896 | NM_002508 | NID1 |
| 7976812 | 1.13702929 | 6.738085651 | 0.999729896 | NR_003232 | SNORD113-4 |
| 8114287 | 1.145359835 | 8.036171115 | 0.999729896 | NM_004598 | SPOCK1 |
| 8142079 | 1.152407544 | 5.200006643 | 0.999729896 | NM_021930 | RINT1 |
| 7954864 | 1.171652399 | 6.090306778 | 0.999729896 | AK093065 | MUC19 |
| 8081826 | 1.181116119 | 7.874543353 | 0.999729896 | NM_006952 | UPK1B |
| 8160459 | 1.181155278 | 7.343136196 | 0.999729896 | NM_004432 | ELAVL2 |
| 8068713 | 1.18735644 | 7.345624098 | 0.999729896 | NM_002462 | MX1 |
| 8045835 | 1.199830672 | 9.690183382 | 0.999729896 | NM_014568 | GALNT5 |
| 8171472 | 1.22013927 | 7.27697454 | 0.999729896 | NM_020665 | TMEM27 |
| 8014063 | 1.236058479 | 8.081872747 | 0.999729896 | NM_006495 | EVI2B |
| 8165808 | 1.25990601 | 8.011750348 | 0.999729896 | NM_001141919 | XG |
| 8049246 | 1.268063634 | 10.65513366 | 0.712697347 | NM_001017915 | INPP5D |
| 8103563 | 1.279150889 | 7.810074277 | 0.999729896 | NM_017631 | DDX60 |
| 8057599 | 1.289845792 | 6.203739495 | 0.999729896 | NM_006287 | TFPI |
| 7957861 | 1.34440468 | 6.663391342 | 0.999729896 | NM_178826 | ANO4 |
| 8105061 | 1.35248357 | 5.766629574 | 0.999729896 | NM_001465 | FYB |
| 7929052 | 1.35909515 | 7.15877398 | 0.999729896 | NM_001031683 | IFIT3 |
| 8126279 | 1.362063573 | 8.045950482 | 0.999729896 | NM_018965 | TREM2 |
| 8096361 | 1.378418098 | 5.954980638 | 0.999729896 | NM_016323 | HERC5 |
| 7958913 | 1.392984512 | 8.803259101 | 0.999729896 | NM_002535 | OAS2 |
| 7902660 | 1.41905858 | 7.894732021 | 0.455315593 | NM_145172 | WDR63 |
| 8027002 | 1.424044009 | 9.194510614 | 0.999729896 | NM_004864 | GDF15 |
| 7902553 | 1.482087815 | 6.691796934 | 0.999729896 | NM_006417 | IFI44 |
| 8077899 | 1.501842605 | 7.866811645 | 0.999729896 | NM_138712 | PPARG |
| 7929047 | 1.577676559 | 6.213741015 | 0.999729896 | NM_001547 | IFIT2 |
| 8109528 | 1.602798398 | 8.768169442 | 0.999729896 | NM_001037332 | CYFIP2 |
| 7902541 | 1.664165881 | 8.88478647 | 0.999729896 | NM_006820 | IFI44L |
| 8111739 | 1.676898053 | 9.148251912 | 0.999729896 | NM_001465 | FYB |
| 7914127 | 1.924394298 | 9.461259522 | 0.999729896 | NM_002038 | IFI6 |
| 8101131 | 1.932315025 | 5.207188054 | 0.999729896 | NM_005409 | CXCL11 |
| 7922174 | 2.111870284 | 7.21208608 | 0.999729896 | NM_000130 | F5 |
| 8101126 | 2.182927545 | 6.028542096 | 0.999729896 | NM_001565 | CXCL10 |
| 7929065 | 2.192918844 | 6.808837701 | 0.999729896 | NM_001548 | IFIT1 |

FIG. 15 (Cont. 2)

Genes with significant expression change after the second genetic modification, which led to immortalization.

| probe.set.ID | logFC | AveExpr | adj.P.Val | ACCNUM | SYMBOL |
|---|---|---|---|---|---|
| 8031646 | -4.393933565 | 7.15639777 | 0.001455237 | AK302988 | MORT(ZNF667-AS1) |
| 8105302 | -2.824723024 | 9.514861046 | 0.014739226 | NM_006350 | FST |
| 8180352 | -2.821794888 | 9.452763643 | 0.04642681 | NM_054031 | MRGPRX3 |
| 7938741 | -2.774890625 | 8.473144131 | 0.043055002 | NM_054031 | MRGPRX3 |
| 7962000 | -2.687648595 | 9.811437683 | 0.005777699 | NM_198965 | PTHLH |
| 7964733 | -2.677709065 | 6.623666674 | 0.014150055 | NR_026825 | RPSAP52 |
| 7976816 | -2.524327512 | 7.266038447 | 0.014739226 | NR_003195 | SNORD114-3 |
| 7952490 | -2.510831456 | 8.148392501 | 0.043989612 | NM_005103 | FEZ1 |
| 8050497 | -2.460431917 | 8.076337774 | 0.003454147 | NM_145260 | OSR1 |
| 8126784 | -2.418978668 | 7.813243746 | 0.013591143 | NM_001168357 | PLA2G7 |
| 7942135 | -2.393604548 | 8.455958339 | 0.01721316 | NM_018043 | ANO1 |
| 8136200 | -2.241452726 | 10.28361335 | 0.030511682 | NM_016352 | CPA4 |
| 7965335 | -2.114550704 | 10.61455063 | 0.003559168 | NM_001946 | DUSP6 |
| 8069676 | -2.074094027 | 7.38859308 | 0.006924425 | NM_006988 | ADAMTS1 |
| 8151931 | -2.001022017 | 7.456055593 | 0.026072854 | NM_033512 | TSPYL5 |
| 8041383 | -1.953124279 | 9.739121801 | 0.044666194 | NM_206943 | LTBP1 |
| 8147461 | -1.918256098 | 7.854381263 | 0.014739226 | NM_002998 | SDC2 |
| 8081620 | -1.917518614 | 7.641629498 | 0.009793219 | NM_013259 | TAGLN3 |
| 7965036 | -1.877752095 | 7.890956627 | 0.028027496 | GENSCAN00000024161 | NA |
| 7943197 | -1.869948947 | 7.183902595 | 0.043055002 | NM_001098672 | HEPHL1 |
| 8145766 | -1.848572501 | 9.189528026 | 0.01721316 | ENST00000423322 | NA |
| 8025402 | -1.845388359 | 10.88515077 | 0.046246198 | NM_139314 | ANGPTL4 |
| 7979133 | -1.831541779 | 8.330391601 | 0.028027496 | NM_007361 | NID2 |
| 8033667 | -1.804980237 | 6.455382267 | 0.023676901 | NM_144693 | ZNF558 |
| 8169073 | -1.787991189 | 6.470496965 | 0.019044605 | NM_194324 | TMSB15B |
| 8172204 | -1.778905952 | 6.825998695 | 0.018078882 | NM_000898 | MAOB |
| 8114797 | -1.760409313 | 7.186580114 | 0.044666194 | NM_030964 | SPRY4 |
| 7976826 | -1.711415779 | 5.873506743 | 0.014150055 | NR_003219 | SNORD114-26 |
| 8035896 | -1.691822358 | 7.861611008 | 0.005217438 | NM_020856 | TSHZ3 |
| 8169115 | -1.688485376 | 6.110217523 | 0.013591143 | NM_198465 | NRK |
| 8059854 | -1.675701811 | 9.559478779 | 0.00077923 | NM_005737 | ARL4C |
| 7963406 | -1.586161956 | 12.45916716 | 0.0179214 | NM_005555 | KRT6B |
| 7956867 | -1.582446399 | 8.741997949 | 0.014150055 | NM_003483 | HMGA2 |
| 8111772 | -1.54535793 | 9.098686317 | 0.039263916 | NM_001343 | DAB2 |
| 7965941 | -1.541984183 | 8.97997023 | 0.013591143 | NM_031302 | GLT8D2 |
| 7974270 | -1.541510624 | 8.678199931 | 0.039805163 | NM_015915 | ATL1 |
| 8027247 | -1.475672985 | 7.604024306 | 0.047165889 | NM_031218 | ZNF93 |
| 8046824 | -1.459342532 | 6.376244281 | 0.043055002 | AK092099 | FSIP2 |

FIG. 16

| | | | | | |
|---|---|---|---|---|---|
| 8043114 | -1.447205431 | 7.75485795 | 0.037117447 | NM_031283 | TCF7L1 |
| 8101260 | -1.440042866 | 9.877093986 | 0.034173104 | NM_058172 | ANTXR2 |
| 7976795 | -1.439980258 | 7.083203127 | 0.037117447 | NR_003530 | MEG3 |
| 7944803 | -1.403028942 | 8.006613342 | 0.037795501 | NM_001130142 | VWA5A |
| 8145736 | -1.401141385 | 8.823056229 | 0.028027496 | NM_013958 | NRG1 |
| 8175217 | -1.398777565 | 6.180981323 | 0.032855281 | NM_001448 | GPC4 |
| 7930208 | -1.392403846 | 7.116375556 | 0.026072854 | NM_032727 | INA |
| 8158059 | -1.367452315 | 10.12293764 | 0.014739226 | NM_003165 | STXBP1 |
| 8090098 | -1.354274842 | 8.754329362 | 0.017481608 | NM_053025 | MYLK |
| 8031659 | -1.280923229 | 7.21615561 | 0.013591143 | NM_020828 | ZFP28 |
| 8095728 | -1.280857552 | 10.28616865 | 0.039805163 | NM_001432 | EREG |
| 7945245 | -1.239459868 | 7.573323787 | 0.019680151 | NM_016522 | NTM |
| 8024518 | -1.234486997 | 6.937525769 | 0.039805163 | NM_152791 | ZNF555 |
| 7976810 | -1.214260901 | 4.392251847 | 0.046161381 | NR_003231 | SNORD113-3 |
| 7917942 | -1.179111939 | 6.294183536 | 0.022996376 | AK092728 | MIR137HG |
| 7965040 | -1.174201899 | 10.78774889 | 0.009982281 | NM_007350 | PHLDA1 |
| 8048995 | -1.140757503 | 9.244928814 | 0.017042116 | NM_030926 | ITM2C |
| 7996883 | -1.140260039 | 8.612932187 | 0.024345369 | NM_005329 | HAS3 |
| 8052872 | -1.124338954 | 9.653641485 | 0.006522024 | NM_003236 | TGFA |
| 8081686 | -1.105581803 | 6.51235577 | 0.036763775 | NM_033254 | BOC |
| 8126839 | -1.079934975 | 10.31779566 | 0.044054948 | NM_014452 | TNFRSF21 |
| 8044499 | -1.064488012 | 11.41639184 | 0.032600488 | NM_005415 | SLC20A1 |
| 7996027 | -1.061814274 | 7.335571109 | 0.044666194 | NM_002996 | CX3CL1 |
| 8050537 | -1.046172752 | 6.730047549 | 0.005217438 | NM_002381 | MATN3 |
| 8031768 | -1.041402666 | 6.431661244 | 0.048919214 | NM_001010879 | ZIK1 |
| 8084794 | -1.0247322 | 9.78691922 | 0.030666931 | NM_002182 | IL1RAP |
| 8059470 | -1.017706177 | 9.569609062 | 0.029842637 | NM_005544 | IRS1 |
| 8051187 | -1.013830597 | 8.336420671 | 0.039143824 | NM_022823 | FNDC4 |
| 8089082 | -0.997254494 | 12.02004515 | 0.01923928 | NM_080927 | DCBLD2 |
| 7917944 | -0.991060439 | 5.285298693 | 0.02414674 | NR_029679 | MIR137 |
| 8046646 | -0.970744415 | 8.689027255 | 0.044054948 | NM_032523 | OSBPL6 |
| 8166442 | -0.966559276 | 10.45467618 | 0.030666931 | NM_014888 | FAM3C |
| 8142540 | -0.965518551 | 10.50682172 | 0.030511682 | NM_014888 | FAM3C |
| 8151756 | -0.96394698 | 7.605477235 | 0.013591143 | NM_018710 | TMEM55A |
| 8161701 | -0.952714455 | 9.941597642 | 0.013591143 | NM_013390 | TMEM2 |
| 8132725 | -0.938467941 | 8.677246226 | 0.043055002 | NM_003364 | UPP1 |
| 7915955 | -0.933382576 | 7.49825962 | 0.031118858 | NM_019073 | SPATA6 |
| 7990080 | -0.923086484 | 9.035455406 | 0.032448937 | NM_018357 | LARP6 |
| 7946142 | -0.921746452 | 10.56021122 | 0.013591143 | NM_145040 | PRKCDBP |
| 7970844 | -0.914402626 | 7.890883395 | 0.013591143 | NM_001014380 | KATNAL1 |

FIG. 16 (Cont. 1)

| | | | | | |
|---|---|---|---|---|---|
| 7984588 | -0.892393075 | 8.264920214 | 0.028027496 | NM_024817 | THSD4 |
| 8009951 | -0.884532975 | 12.31598878 | 0.01721316 | NM_000213 | ITGB4 |
| 8061447 | -0.878331883 | 11.81283453 | 0.014739226 | NM_002862 | PYGB |
| 8180282 | -0.876586014 | 8.318452817 | 0.043055002 | NM_032098 | PCDHGB4 |
| 8105267 | -0.873889846 | 11.61054519 | 0.013591143 | NM_002203 | ITGA2 |
| 8015049 | -0.863510705 | 4.388368372 | 0.042101603 | NM_152349 | KRT222 |
| 8034334 | -0.86149741 | 5.519247393 | 0.013591143 | NM_021143 | ZNF20 |
| 8039593 | -0.856109169 | 5.544553054 | 0.044054948 | NM_022103 | ZNF667 |
| 7931353 | -0.848658133 | 8.788277044 | 0.043055002 | NM_006504 | PTPRE |
| 8094911 | -0.847995696 | 10.76554831 | 0.045936624 | NM_020453 | ATP10D |
| 7995697 | -0.839067495 | 11.61434699 | 0.014739226 | NM_017839 | LPCAT2 |
| 8172035 | -0.832069288 | 9.887484399 | 0.032448937 | NM_006520 | DYNLT3 |
| 8025382 | -0.826953637 | 7.385548699 | 0.030666931 | NM_024552 | CERS4 |
| 7936439 | -0.810031312 | 8.248968781 | 0.013591143 | NM_001001936 | AFAP1L2 |
| 8072413 | -0.803688123 | 8.873015026 | 0.024544012 | NM_134269 | SMTN |
| 8046380 | -0.803169334 | 12.07993131 | 0.04642681 | NM_000210 | ITGA6 |
| 8081838 | -0.797869522 | 7.90857498 | 0.024345369 | NM_020754 | ARHGAP31 |
| 8078350 | -0.795569317 | 11.93184636 | 0.013591143 | NM_001024847 | TGFBR2 |
| 8172268 | -0.795396692 | 6.356284592 | 0.039805163 | NR_029636 | MIR222 |
| 8060758 | -0.777484609 | 12.21817339 | 0.016599866 | NM_000311 | PRNP |
| 8178435 | -0.777098183 | 11.31128771 | 0.048503685 | NM_003897 | IER3 |
| 8095736 | -0.772980138 | 12.90170882 | 0.030229825 | NM_001657 | AREG |
| 8099388 | -0.762893247 | 8.025362444 | 0.044666194 | NM_005114 | HS3ST1 |
| 8042038 | -0.758679591 | 6.216046445 | 0.031115383 | NR_002229 | RPL23AP32 |
| 8124848 | -0.755777799 | 11.00415019 | 0.04875233 | NM_003897 | IER3 |
| 8179704 | -0.755777799 | 11.00415019 | 0.04875233 | NM_003897 | IER3 |
| 8128737 | -0.755262195 | 7.633180634 | 0.035700102 | NM_022765 | MICAL1 |
| 8008237 | -0.753023137 | 11.88847655 | 0.013591143 | NM_002204 | ITGA3 |
| 7979943 | -0.744302316 | 8.808471514 | 0.030666931 | NM_033141 | MAP3K9 |
| 7956166 | -0.738876054 | 10.83882529 | 0.019044605 | NM_015292 | ESYT1 |
| 8133459 | -0.721826703 | 7.553556859 | 0.039805163 | NM_003388 | CLIP2 |
| 7982564 | -0.70795576 | 9.696741125 | 0.030666931 | NM_152594 | SPRED1 |
| 8050894 | -0.701412397 | 8.484070446 | 0.014739226 | NM_002254 | KIF3C |
| 8091422 | -0.699453998 | 10.14296651 | 0.013591143 | NM_001168278 | WWTR1 |
| 7918275 | -0.697897524 | 9.26072294 | 0.037795501 | NM_001142550 | WDR47 |
| 8154848 | -0.691293267 | 8.15038944 | 0.029484433 | NM_007343 | PRSS3 |
| 8086981 | -0.691102158 | 6.611963198 | 0.039795523 | NM_033199 | UCN2 |
| 8099965 | -0.686436444 | 9.261633703 | 0.028027496 | NM_007274 | ACOT7 |
| 7972003 | -0.664554773 | 8.371644053 | 0.037795501 | NM_007249 | KLF12 |
| 8095744 | -0.663034639 | 13.09305562 | 0.041007289 | NM_001657 | AREG |

FIG. 16 (Cont. 2)

| | | | | | |
|---|---|---|---|---|---|
| 7988921 | -0.659491075 | 9.560541053 | 0.014150055 | NM_000259 | MYO5A |
| 8167815 | -0.659338493 | 8.32721972 | 0.043055002 | NM_014599 | MAGED2 |
| 8078405 | -0.658032961 | 10.88740363 | 0.014739226 | NM_138410 | CMTM7 |
| 8127563 | -0.657429326 | 10.87860588 | 0.013591143 | NM_004370 | COL12A1 |
| 7930927 | -0.65567875 | 8.446385712 | 0.038498274 | NM_014937 | INPP5F |
| 8015635 | -0.655111499 | 9.582189608 | 0.01721316 | NM_012232 | PTRF |
| 8118682 | -0.650036268 | 7.971232526 | 0.013591143 | NR_027692 | PHF1 |
| 7913237 | -0.648418959 | 12.04916352 | 0.014739226 | NM_018584 | CAMK2N1 |
| 8119466 | -0.645277057 | 8.884281894 | 0.032448937 | NM_005586 | MDFI |
| 8089329 | -0.643585617 | 5.537303473 | 0.01721316 | NM_014981 | MYH15 |
| 8021047 | -0.643285406 | 7.871080246 | 0.039805163 | NM_015559 | SETBP1 |
| 7990674 | -0.639089672 | 6.613525181 | 0.043055002 | NM_006383 | CIB2 |
| 8171684 | -0.639067735 | 9.874269088 | 0.013591143 | NM_031892 | SH3KBP1 |
| 8110486 | -0.636692076 | 5.845501499 | 0.031115383 | NM_001136116 | ZNF879 |
| 8042168 | -0.631206862 | 7.643786879 | 0.013591143 | NM_001129993 | KIAA1841 |
| 7992789 | -0.630446971 | 11.29180114 | 0.04642681 | NM_016639 | TNFRSF12A |
| 8131339 | -0.629687459 | 11.7201246 | 0.02213762 | NM_003088 | FSCN1 |
| 7958253 | -0.625337417 | 11.07690608 | 0.039805163 | NM_001145199 | C12orf75 |
| 7999598 | -0.60795425 | 9.61543967 | 0.03297621 | NM_173474 | NTAN1 |
| 8100318 | -0.604250004 | 10.29452691 | 0.015271814 | NM_000232 | SGCB |
| 7912257 | -0.603243769 | 10.353727 | 0.025448717 | NM_001009566 | CLSTN1 |
| 8051814 | -0.602986539 | 11.31375582 | 0.034337931 | NM_006887 | ZFP36L2 |
| 8131205 | -0.601026217 | 6.818047866 | 0.014739226 | NM_152744 | SDK1 |
| 8083569 | -0.598821143 | 11.04838122 | 0.039263916 | NM_015508 | TIPARP |
| 7912004 | -0.597347279 | 8.650769179 | 0.041530736 | NM_207370 | GPR153 |
| 7915801 | -0.589341859 | 9.609250227 | 0.001455237 | NM_017739 | POMGNT1 |
| 7928395 | -0.576793496 | 9.528175267 | 0.037795501 | NM_173540 | FUT11 |
| 8086517 | -0.570417743 | 11.37446245 | 0.042976155 | NM_022842 | CDCP1 |
| 8107673 | -0.568834562 | 9.754167417 | 0.030666931 | NM_023927 | GRAMD3 |
| 8028656 | -0.566791146 | 7.546021378 | 0.043055002 | NM_022835 | PLEKHG2 |
| 7969626 | -0.560899463 | 9.788614937 | 0.016599866 | NM_180989 | GPR180 |
| 7900235 | -0.550526977 | 10.02539414 | 0.032855281 | NM_012090 | MACF1 |
| 7932554 | -0.546842855 | 10.48863642 | 0.003454147 | NM_020824 | ARHGAP21 |
| 8132503 | -0.546328558 | 11.21277785 | 0.045088338 | NM_004760 | STK17A |
| 8080714 | -0.546259155 | 11.95260632 | 0.024345369 | NM_001164317 | FLNB |
| 8040530 | -0.545121844 | 9.208364476 | 0.039696797 | NM_054033 | FKBP1B |
| 8153568 | -0.544867478 | 10.17460981 | 0.030511682 | NM_201384 | PLEC |
| 8140534 | -0.544588285 | 10.68870391 | 0.01585329 | NM_006379 | SEMA3C |
| 8120880 | -0.528899649 | 10.41494304 | 0.031115383 | NM_006670 | TPBG |
| 7927955 | -0.525604095 | 9.602140327 | 0.035849339 | NM_015634 | KIAA1279 |

FIG. 16 (Cont. 3)

| | | | | | |
|---|---|---|---|---|---|
| 8093145 | -0.518980291 | 5.841756036 | 0.044958902 | NM_032898 | CEP19 |
| 8110491 | -0.518958236 | 5.95103927 | 0.025448717 | NM_014594 | ZNF354C |
| 8017651 | -0.51567555 | 10.29295237 | 0.027021203 | NM_022739 | SMURF2 |
| 8029969 | -0.511599321 | 10.03420794 | 0.034823559 | NM_003009 | SEPW1 |
| 8174779 | -0.511070061 | 11.30443773 | 0.039563825 | NM_013995 | LAMP2 |
| 7899153 | -0.503724319 | 8.943268036 | 0.019017729 | NM_031286 | SH3BGRL3 |
| 7980616 | -0.503038972 | 7.92528491 | 0.014739226 | NM_007039 | PTPN21 |
| 7941565 | -0.485850242 | 8.81060581 | 0.014739226 | NM_022822 | KLC2 |
| 8100615 | -0.484694765 | 10.61835309 | 0.029947602 | NM_018227 | UBA6 |
| 8169519 | -0.483392455 | 8.534028864 | 0.039263916 | NM_019045 | WDR44 |
| 8147019 | -0.48323584 | 8.88665761 | 0.032448937 | NM_016010 | ZC2HC1A |
| 7984743 | -0.478366418 | 9.657715732 | 0.039805163 | NM_001024736 | CD276 |
| 8155062 | -0.478071293 | 9.354779499 | 0.04642681 | NM_006285 | TESK1 |
| 8132214 | -0.477128425 | 9.019932071 | 0.044666194 | NM_007270 | FKBP9 |
| 8072894 | -0.473647931 | 7.559957527 | 0.036662306 | NM_001039141 | TRIOBP |
| 7967002 | -0.47167528 | 9.659546106 | 0.014739226 | NM_001080855 | PXN |
| 7976976 | -0.467804376 | 8.020000832 | 0.026072854 | NM_014844 | TECPR2 |
| 8020220 | -0.463873246 | 11.38569639 | 0.039696797 | NM_032525 | TUBB6 |
| 7926189 | -0.461612523 | 8.415566261 | 0.026072854 | NM_018144 | SEC61A2 |
| 7927786 | -0.459485689 | 11.20980431 | 0.043055002 | NM_001001330 | REEP3 |
| 8017582 | -0.449544653 | 10.08089548 | 0.048958622 | NM_018469 | TEX2 |
| 7991587 | -0.434036466 | 8.046752296 | 0.046368147 | NM_203472 | VIMP |
| 8175299 | -0.43216524 | 9.241644798 | 0.026318775 | NM_001078173 | FAM127C |
| 8077458 | -0.429440612 | 9.575659479 | 0.030511682 | NM_014674 | EDEM1 |
| 8137865 | -0.418977286 | 9.507700434 | 0.048489078 | NM_007353 | GNA12 |
| 7916669 | -0.411577066 | 10.09063141 | 0.014739226 | NM_033407 | DOCK7 |
| 7912012 | -0.410598438 | 8.798900422 | 0.032448937 | NM_007274 | ACOT7 |
| 8068280 | -0.391048052 | 9.644266814 | 0.039263916 | NM_005534 | IFNGR2 |
| 8082607 | -0.390802461 | 9.653042186 | 0.036763775 | NM_014382 | ATP2C1 |
| 8076046 | -0.389748934 | 10.67337086 | 0.030746917 | NM_012264 | TMEM184B |
| 7932966 | -0.375749708 | 11.75550602 | 0.044054948 | NM_033666 | ITGB1 |
| 8135576 | -0.373742477 | 11.68239129 | 0.046161381 | NM_015641 | TES |
| 8145624 | -0.37329115 | 9.228920705 | 0.042101603 | NM_001440 | EXTL3 |
| 8164701 | -0.349249278 | 9.49587009 | 0.028027496 | NM_015046 | SETX |
| 8042772 | -0.339401621 | 10.44274014 | 0.034823559 | NM_213622 | STAMBP |
| 8095566 | -0.337537443 | 9.505843072 | 0.029484433 | NM_173468 | MOB1B |
| 8103646 | -0.337125053 | 8.214958235 | 0.043055002 | NM_012224 | NEK1 |
| 7956842 | -0.327466455 | 8.466555455 | 0.026072854 | NM_014319 | LEMD3 |
| 7979824 | -0.322395528 | 12.8174353 | 0.042976155 | NM_001130004 | ACTN1 |
| 8053107 | -0.320999386 | 9.722441345 | 0.030666931 | NM_004082 | DCTN1 |

FIG. 16 (Cont. 4)

| | | | | | |
|---|---|---|---|---|---|
| 8028162 | -0.315568581 | 11.12487484 | 0.01721316 | NM_001281 | TBCB |
| 8012304 | -0.313863946 | 11.72762962 | 0.015268365 | NM_021210 | TRAPPC1 |
| 7989199 | -0.307001789 | 5.192573961 | 0.039247088 | NM_003888 | ALDH1A2 |
| 8154523 | -0.301909669 | 8.563314201 | 0.039805163 | NM_006570 | RRAGA |
| 8084818 | -0.296304317 | 10.15955646 | 0.0381791 | NM_178335 | CCDC50 |
| 8025414 | -0.273877778 | 10.64454238 | 0.042101603 | NM_004218 | RAB11B |
| 7900382 | -0.271388217 | 12.51713418 | 0.037530872 | NM_006367 | CAP1 |
| 7948534 | 0.282215947 | 11.20891382 | 0.028027496 | NM_001923 | DDB1 |
| 8155234 | 0.293087731 | 8.630582633 | 0.043055002 | NM_032226 | ZCCHC7 |
| 8147503 | 0.303716263 | 11.82919939 | 0.046558342 | NM_018407 | LAPTM4B |
| 8052934 | 0.312089688 | 6.506959923 | 0.043055002 | NM_032601 | MCEE |
| 7973826 | 0.315850792 | 8.044606166 | 0.046161381 | NM_025152 | NUBPL |
| 7956930 | 0.319383101 | 8.570464664 | 0.039805163 | NM_006482 | DYRK2 |
| 8023871 | 0.333128414 | 9.263014944 | 0.04642681 | NM_175907 | ZADH2 |
| 7971615 | 0.364951232 | 10.63904441 | 0.039263916 | NM_032565 | EBPL |
| 7961767 | 0.366324668 | 9.326117337 | 0.044054948 | AK295862 | KIAA0528 |
| 8135268 | 0.377761399 | 12.02834333 | 0.042976155 | NM_001417 | EIF4B |
| 7969364 | 0.383554681 | 3.639515466 | 0.024544012 | ENST00000365608 | NA |
| 8165046 | 0.385528231 | 9.603111536 | 0.04875233 | NM_015447 | CAMSAP1 |
| 8060063 | 0.392296169 | 8.649742071 | 0.013591143 | NM_004544 | NDUFA10 |
| 7914245 | 0.405934944 | 8.90186866 | 0.037795501 | NM_001024732 | MECR |
| 8173629 | 0.418151949 | 9.855368613 | 0.039795523 | NM_004299 | ABCB7 |
| 8112740 | 0.422689287 | 7.653151344 | 0.019680151 | NM_032367 | ZBED3 |
| 8063337 | 0.422743739 | 9.031441867 | 0.044054948 | NR_003605 | ZNFX1-AS1 |
| 8000603 | 0.425558005 | 10.09926303 | 0.029484433 | NM_003321 | TUFM |
| 7985248 | 0.427767031 | 5.940508844 | 0.014739226 | NM_015206 | KIAA1024 |
| 8010137 | 0.441514822 | 7.954975907 | 0.039263916 | NR_003013 | SCARNA16 |
| 7901110 | 0.443305087 | 10.3113997 | 0.039805163 | NM_006066 | AKR1A1 |
| 7986323 | 0.462757095 | 10.28079651 | 0.036763775 | NM_015710 | GLTSCR2 |
| 7942274 | 0.465051651 | 6.491892295 | 0.035700102 | ENST00000329336 | NA |
| 8044793 | 0.466755689 | 8.969507905 | 0.035093032 | NM_182915 | STEAP3 |
| 8090559 | 0.492883654 | 6.815394378 | 0.015271814 | NR_003111 | RPL32P3 |
| 8100532 | 0.497383982 | 10.44299206 | 0.018078882 | NM_032313 | NOA1 |
| 8096753 | 0.509798624 | 9.774931898 | 0.030522047 | NM_005327 | HADH |
| 8138277 | 0.540151494 | 7.708491254 | 0.039805163 | NM_001135924 | VWDE |
| 7925174 | 0.558777633 | 10.44874731 | 0.02414674 | NM_014765 | TOMM20 |
| 8010080 | 0.564110794 | 5.105909204 | 0.045173568 | NR_004396 | SNORD1B |
| 7977497 | 0.564584291 | 7.585771253 | 0.039805163 | NM_021178 | CCNB1IP1 |
| 7919038 | 0.57803626 | 9.144758966 | 0.026072854 | NM_201263 | WARS2 |
| 7971757 | 0.582845247 | 5.418630243 | 0.044054948 | NM_199289 | NEK5 |

FIG. 16 (Cont. 5)

| | | | | | |
|---|---|---|---|---|---|
| 7979351 | 0.584220098 | 7.835913631 | 0.013591143 | NR_027123 | KTN1-AS1 |
| 8109576 | 0.59417069 | 9.1809966 | 0.019044605 | NM_017872 | THG1L |
| 8073311 | 0.595856225 | 9.440693475 | 0.034823559 | NM_022098 | XPNPEP3 |
| 7913154 | 0.596638243 | 7.825450008 | 0.013591143 | AK094604 | NA |
| 7922402 | 0.596783471 | 10.10909639 | 0.026395095 | NR_002746 | SNORD47 |
| 7923810 | 0.602811122 | 3.840259494 | 0.043055002 | ENST00000365074 | NA |
| 8106516 | 0.608468225 | 8.405686857 | 0.039263916 | NM_152405 | JMY |
| 8098995 | 0.608677025 | 8.785941721 | 0.017042116 | NM_006454 | MXD4 |
| 7980773 | 0.612448694 | 7.288374242 | 0.019680151 | NM_001080414 | CCDC88C |
| 8069332 | 0.622901692 | 7.268573705 | 0.024544012 | NR_002776 | MCM3AP-AS1 |
| 7999025 | 0.632556002 | 11.37324489 | 0.028027496 | NM_016292 | TRAP1 |
| 7911341 | 0.665791655 | 9.431956765 | 0.030511682 | NC_001807 | NA |
| 7955450 | 0.669615726 | 10.41490481 | 0.021087037 | NM_015416 | LETMD1 |
| 8005957 | 0.682019922 | 8.874599936 | 0.048503685 | NR_000009 | SNORD4B |
| 8092328 | 0.708433869 | 8.148767142 | 0.039805163 | NM_020166 | MCCC1 |
| 8094688 | 0.729501778 | 8.90008444 | 0.023490552 | NM_006859 | LIAS |
| 7972579 | 0.731464255 | 8.106210751 | 0.014150055 | NM_032813 | TMTC4 |
| 8130556 | 0.741662494 | 9.00462803 | 0.013591143 | NM_001024465 | SOD2 |
| 8010078 | 0.752445428 | 9.362725725 | 0.048489078 | NR_004397 | SNORD1C |
| 8128726 | 0.778224734 | 6.201114551 | 0.024544012 | NM_173672 | PPIL6 |
| 7943984 | 0.808593385 | 7.4949797 | 0.036763775 | NM_006006 | ZBTB16 |
| 8051001 | 0.832415128 | 7.179948481 | 0.028868465 | NM_006569 | CGREF1 |
| 8162236 | 0.856334007 | 6.709742203 | 0.030569061 | NM_006378 | SEMA4D |
| 7911339 | 0.880694127 | 11.08386877 | 0.044054948 | NR_031741 | NA |
| 8165698 | 0.880694127 | 11.08386877 | 0.044054948 | NR_031741 | NA |
| 7926223 | 0.920641376 | 6.86415244 | 0.026072854 | NM_153498 | CAMK1D |
| 7970989 | 0.937882958 | 6.760761177 | 0.019496163 | NM_001144981 | CCDC169 |
| 8104930 | 0.993407553 | 8.812963684 | 0.031902297 | NM_004172 | SLC1A3 |
| 7993756 | 1.025654172 | 5.91039783 | 0.018078882 | NM_005622 | ACSM3 |
| 7910164 | 1.158988119 | 7.748883833 | 0.003373783 | NM_020247 | ADCK3 |
| 7955441 | 1.215439687 | 8.948615108 | 0.024544012 | NM_014033 | METTL7A |
| 8001918 | 1.258480168 | 6.673876935 | 0.025448717 | NM_001128850 | RRAD |
| 7997942 | 1.315127787 | 6.956497223 | 0.013591143 | NM_014427 | CPNE7 |
| 8011415 | 1.401296871 | 8.408104221 | 0.024690221 | NM_002561 | P2RX5 |
| 8103769 | 1.471902081 | 5.387612603 | 0.047165889 | NM_000860 | HPGD |
| 8033241 | 1.496557308 | 7.424126691 | 0.013591143 | NM_001252 | CD70 |
| 7942064 | 1.704493931 | 8.73762634 | 0.014739226 | NM_015973 | GAL |
| 7956826 | 1.863544121 | 6.18631099 | 0.013591143 | AB449914 | TBC1D30 |
| 7983650 | 2.172119935 | 7.499791368 | 0.044054948 | NM_003645 | SLC27A2 |

FIG. 16 (Cont. 6)

Genes whose expression were significantly changed after multiple testing.

| GOBPID | Pvalue | OddsRatio | ExpCount | Count | Size | Term | DE gene SYMBOLS | concordance with TCGA |
|---|---|---|---|---|---|---|---|---|
| GO:0007229 | 1.182E-05 | 8.48 | 1.08 | 8 | 75 | integrin-mediated signaling pathway | DAB2, ITGA6, ITGA2, ITGA3, ITGB1, ITGB4, PXN, ADAMTS1 | 100.0 |
| GO:0009653 | 0.0001042 | 1.92 | 30.49 | 51 | 2119 | anatomical structure morphogenesis | DAB2, DUSP6, EREG, GPC4, GNA12, NRG1, HPGD, ITGA6, ITGA2, ITGB1, MDFI, MYLK, MYO5A, NEK1, PRNP, PTHLH, PXN, CX3CL1, SDC2, SLC1A3, STXBP1, TGFA, TGFBR2, ZBTB16, HMGA2, ALDH1A2, IER3, ADAMTS1, FEZ1, WARS2, FST, CAP1, SEMA4D, SEMA3C, LIAS, TRIOBP, MACF1, WWTR1, TIPARP, SH3KBP1, ATL1, ANGPTL4, TNFRSF12A, TSHZ3, CCNB1IP1, NUBPL, TCF7L1, DOCK7, BOC, OSR1, CAMSAP1 | 74.5 |
| GO:0043467 | 0.000147 | 8.44 | 0.81 | 6 | 56 | regulation of generation of precursor metabolites and energy | IRS1, DYRK2, IER3, TRAP1, VIMP, NOA1 | 50.0 |
| GO:0010942 | 0.000182 | 3.07 | 5.66 | 16 | 393 | positive regulation of cell death | DUSP6, ITGA6, ITGB1, MAP3K9, ZBTB16, HMGA2, ALDH1A2, STK17A, RRAGA, PHLDA1, GAL, TNFRSF12A, STEAP3, CAMK1D, PLEKHG2, JMY | 56.3 |
| GO:0043065 | 0.0002782 | 3.07 | 5.28 | 15 | 367 | positive regulation of apoptotic process | DUSP6, ITGA6, ITGB1, MAP3K9, ZBTB16, HMGA2, ALDH1A2, STK17A, PHLDA1, GAL, TNFRSF12A, STEAP3, CAMK1D, PLEKHG2, JMY | 53.3 |

FIG. 17

Genes whose expression were significantly changed after multiple testing.

| GOBPID | Pvalue | OddsRatio | ExpCount | Count | Size | Term | DE gene SYMBOLS | concordance with TCGA |
|---|---|---|---|---|---|---|---|---|
| GO:0016265 | 0.0002983 | 1.93 | 25.30 | 43 | 1758 | death | ACTN1, CD70, DAB2, DCTN1, DUSP6, NRG1, ITGA6, ITGB1, MAP3K9, PLEC, PRNP, CX3CL1, STXBP1, TGFA, TGFBR2, ZBTB16, HMGA2, DYRK2, ALDH1A2, IER3, STK17A, TECPR2, SEMA4D, STAMBP, RRAGA, PHLDA1, SETX, TNFRSF21, SH3KBP1, ATL1, GAL, ANGPTL4, TNFRSF12A, STEAP3, VIMP, ADCK3, CAMK1D, MICAL1, PLEKHG2, ITM2C, NOA1, OSR1, JMY | 67.4 |
| GO:0007160 | 0.0003198 | 4.53 | 2.16 | 9 | 150 | cell-matrix adhesion | ACTN1, ITGA6, ITGA2, ITGA3, ITGB1, ITGB4, PXN, NID2, MACF1 | 88.9 |
| GO:0072189 | 0.000327 | 29.78 | 0.14 | 3 | 10 | ureter development | ALDH1A2, TSHZ3, OSR1 | 100.0 |
| GO:0031581 | 0.0004448 | 26.06 | 0.16 | 3 | 11 | hemidesmosome assembly | ITGA6, ITGB4, PLEC | 66.7 |
| GO:0042060 | 0.0004722 | 2.49 | 8.72 | 20 | 606 | wound healing | ACTN1, EREG, GNA12, NRG1, ITGA6, ITGA2, ITGA3, ITGB1, KIF3C, LAMP2, MYLK, CX3CL1, SDC2, STXBP1, TGFA, TGFBR2, CAP1, MACF1, KLC2, DCBLD2 | 80.0 |
| GO:0030198 | 0.0005349 | 3.00 | 5.02 | 14 | 349 | extracellular matrix organization | ACTN1, COL12A1, HAS3, ITGA6, ITGA2, ITGA3, ITGB1, ITGB4, LTBP1, MATN3, PLEC, SDC2, NID2, THSD4 | 64.3 |
| GO:0072194 | 0.0006123 | 138.35 | 0.04 | 2 | 3 | kidney smooth muscle tissue development | TSHZ3, OSR1 | 100.0 |

FIG. 17 (Cont. 1)

Genes whose expression were significantly changed after multiple testing.

| GOBPID | Pvalue | OddsRatio | ExpCount | Count | Size | Term | DE gene SYMBOLS | concordance with TCGA |
|---|---|---|---|---|---|---|---|---|
| GO:0023051 | 0.0006663 | 1.76 | 32.88 | 51 | 2285 | regulation of signaling | DAB2, DUSP6, EREG, FKBP1B, GNA12, NRG1, IFNGR2, ITGA6, IRS1, ITGA2, ITGB1, LTBP1, MDFI, MAP3K9, MYO5A, PRNP, PTPRE, PXN, CX3CL1, SLC1A3, SLC20A1, STXBP1, TGFA, TGFBR2, HMGA2, IER3, RAB11B, FST, SEMA4D, STAMBP, RRAGA, INPP5F, MACF1, LEMD3, WWTR1, ATP2C1, SH3KBP1, TNFRSF12A, VIMP, ARHGAP31, SMURF2, PLEKHG2, ITM2C, SPRY4, TCF7L1, ZBED3, AFAP1L2, DOCK7, TSPYL5, UCN2, SPRED1 | 76.0 |
| GO:0061098 | 0.0007455 | 11.16 | 0.42 | 4 | 29 | positive regulation of protein tyrosine kinase activity | EREG, NRG1, TGFA, AFAP1L2 | 100.0 |
| GO:0017145 | 0.0008506 | 10.73 | 0.43 | 4 | 30 | stem cell division | ZFP36L2, ZBTB16, WWTR1, DOCK7 | 75.0 |
| GO:0007155 | 0.0008832 | 2.11 | 13.41 | 26 | 932 | cell adhesion | ACTN1, COL12A1, DAB2, NRG1, ITGA6, ITGA2, ITGA3, ITGB1, ITGB4, PXN, CX3CL1, STXBP1, TPBG, FEZ1, SEMA4D, CGREF1, TRIOBP, NID2, CLSTN1, MACF1, ATP2C1, NTM, TNFRSF12A, BOC, DCBLD2, SDK1 | 80.8 |
| GO:0012501 | 0.0009428 | 1.85 | 22.68 | 38 | 1576 | programmed cell death | ACTN1, CD70, DAB2, DUSP6, NRG1, ITGA6, ITGB1, MAP3K9, PLEC, PRNP, CX3CL1, STXBP1, TGFA, TGFBR2, ZBTB16, HMGA2, DYRK2, ALDH1A2, IER3, STK17A, SEMA4D, STAMBP, RRAGA, PHLDA1, TNFRSF21, SH3KBP1, GAL, ANGPTL4, TNFRSF12A, STEAP3, VIMP, CAMK1D, MICAL1, PLEKHG2, ITM2C, NOA1, OSR1, JMY | 65.8 |

FIG. 17 (Cont. 2)

MassARRAY primers.

| | | |
|---|---|---|
| SEQ ID NO:3 | mort_Up_10F | aggaagagagTGGTTTTGTTTTTATTTTTTAGGAG |
| SEQ ID NO:4 | mort_Up_T7R | cagtaatacgactcactataggagagaaggctCAAATAAATCCCCACTATTAACCAA |
| SEQ ID NO:5 | mort_Start_10F | aggaagagagTTGGTTAATAGTGGGGATTTATTTG |
| SEQ ID NO:6 | mort_Start_T7R | cagtaatacgactcactataggagagaaggctTCCTCACACATATTCAAAATAACACA |

FIG. 18

SEQUENCE LISTING

<160> NUMBER OF SEQ ID NOS: 8

<210> SEQ ID NO 1

```
<211> LENGTH: 20501
<212> TYPE: DNA
<213> ORGANISM: Homo sapiens

<400> SEQUENCE: 1
ttaagtaagc tctctcagtc acacagccag ccagtggtga aaccaggagt caacaccaga      60
cagcggggcg ccacagtcca tgctcttatt tttccaagct accttggtag aaggggaca     120 caaccatact tagcgtcagt ggagggctct gtcctccact caaatgtaca catgcagaaa    180
actgacgacg caggtggttg gcggggggcag cgcaccactg ctcaactgga gatggtcaga   240
tgccctggta tgtggacaaa gatagcccag tccgaagctc agagatgcaa agtcctccag    300
tattcaccac tacctctgcc tctgtatagg gtcaaagaaa aacgaccacc agcaccataa    360
ccaacaccta aacacggtga ttagtatgtg acaagctctg tgcagggtgt ttcagctacg    420
tcatcccatt taatcttccc aataacaccc aggcaggtgc tattaatatg ctattttacc    480
aaggaggaaa gtcatgcaca attaaacagt tccacagatt tccagggcag cccatcacat    540
cttagagctg ctaagaattc ttcccctgtg ggcctccatt tccatggtta cagtgagata    600
tacaccagaa aggcacagtc acacactcat aaccgcaaag ccactgacgc taagtggcag    660
acagacgccc aggcaagtca cacagtaacc caaggctaca ataaacgccc acatcagcct    720
gacactgaca cacgcacaca ctccagaaac acaaatcttc acagtcagcg tcacacaccc    780
actcccggct tcccaatggc tccattgttt ccttcgcgtg ggtcacgcag cgatacacat    840
ccgcggtccc gacatagctc cctcacacac aggcacacac ggctcgcctc acacgcggcg    900
ccaacttcac acttgggcgc acaagccccg agaaccacag cagcgaaggg cgcaaacccc    960
acgccgtggc gggccgagaa cccacgcagg cgcgagccca ccgcccacgc aagcacccgc   1020
gcagacgccc acgccatcgt ggatgcgcaa acccacgcgc gccttggcag gaacgtccac   1080
gcagtggcgg gcgcgccgcc cacgccctca gacacaccca cactctcgcc agccccctta   1140
cctcggtctt cccgggctca gacccggcg gcgaccaccg agacagccga gcagggactc    1200
agcgcctgcg cactcccctc cgggaccccg ggaccgcgcg ctgcaccccc cttcacacac   1260
gcaccacgca tgcgggcgcg tgccccgccc cccaaacaag gccacgcggc gtgcgctcac   1320
ccgcctctcg gggacagtac caccagcccc ggcctgaggc cccgaccccc cagcgccaca   1380
cgcacaagcg cgttcgcacg attggtgcag gcggacgcgc gaggtcccgc gcctgcgcac   1440 accccgagg ctggcacgca caccggtctc ctaggggact ggcgcctggc cctgcttttc    1500
atcctctcag gagatcacgt gtggacactg aggcccttcc tcgagctctt taaccaaacc   1560
caacctcccc aattcgccgc cttccccgct cccacaacca cacgttcccg tgtgagggct   1620
tattgcctcc agccagccag cgtccttcgc ccccacattc acgaggtttg gagcggcct    1680 cacccgcgga ggcggacacc gcccaccgc gcgtgcgcac tacgcagtca tcctgcgacc   1740
tccagaatcc accggggtgc agcgaggctg tggaaagtcc cacccagaac gtgaggtgaa   1800
gaaggcttgg gctgcgctgg ttctgctctg tccgggtcgg agatgaactg acccgggaga   1860
gcagcggagg gatgtttctt ttggccaaca gtggggactc acctgcacgt tttgcgaaga   1920
ggcccacagt cctttgcgtg gcgctcggac tacatttccc aacggcccct gcacgccctg   1980
ggggctgttc catgcggtgt tgcgcctgcg tagccggcgg gctggcagtg agactgactg   2040
cgtcggggtt gagactgggt ggatgaggct caccccggcg gggagaaggg acgaggaggg   2100
gcggacagcg gaaggtccgg gagtgtccgc cataaagtcg tttgaggtga ccgttgcgta   2160
attgtgagtc tgtgagagaa gatgtgaagt atggcctcgt cccggtcatc tgggcgtgcg   2220
```

```
ggtcccgggt tttgatcgcg cgtttgtgta ggtgagaccc acattgtgtt accctgaaca   2280
tgtgtgagga cgaacctttg tgttttctta tacgtgtgtc tctgaggcga tttttgtggt   2340
tttgtacgtg gcggggggca ctgattttga atatgtgtgt atgttctgga catttgttta   2400
gcttctgcat ccacttctgc ggaagggcag agttgagtag gtgggaacag gtactgtgtg   2460
gccccacaaa gcctgaacta tttactgttg actctagagc ccagttttcg cggtgtgtac   2520
gtctctgtgg ggaaccacac attttgaata tgtatacttg tgtatattta cgtctattct   2580
atgactgctt ttgcacaatg gcagggttca gtacttgcag cagagatctt gtggcccata   2640
aagcctaaaa tactatccga ctaaggtttc gagccgtagc cagttttgt ggatgagtgt    2700
tgtgtgtgtg tgggaagcca gtgattgatt gattgattga ttgatttggg acggagtctc   2760
gctctgtcgc ccaggctgga gtgcagtggc gcgatctcgg ctcactgcaa cctccgcctc   2820
caggttcaag ccattcttct gcctcatcct ccctagtagc tgggactaca ggcgcccgcc   2880
accacgcccg gctaagtttt ttgtattttt agtagattcg ggtttcacc atgtgggctc    2940
ttgacctcgt gatccgcccg cctcggcctc ccaaagtgct gggattacag gcgtgagcca   3000
ccgcgaccgg ccaaggaaag ccagtgtttt tgactctgtg tgtgtgtacc cgcctgtgtg   3060
ttgagaccca gtttttgtag ttgcataggt gggtatatgt gtgaggggaa cccagggcct   3120
gtgatttctt tcttcccagg tgactctgag caagttttgg ggactaggta gtagggagaa   3180
tgtgtgagga actagttttg gtttcccatt tctgtgatta ggtagtagca ataataaaaa   3240
taaaagctaa cagatactac tattaggact tttaccatta cctctgtgac tagcagctag   3300
cacttactga ttgttgtccc tggtcaaaag tgaattttc catttaaggt tttctttaat    3360
cctgtaagcc gttctctgag ttgttccttg gagcaagttt ctttctagac tggagattgt   3420
tctaaatacc tggtaatact agaataaggg gtgtggtcaa gagatccaag aaatcttagg   3480
ataaatctgt cacttggcag tttctttgtt ttctttaaac cacctcccaa gaaagtatgt   3540
catcctttct gctgtttag gggcatgtta gtgcgaaaat ctgggaaaaa gctttatgcc    3600
tcagactgtc ctagttcaga gaaaccagag tgtgtgggtc ggatgtcttg gctcctgatc   3660
aggctctgtt gtgcccattc tccgaataaa gcaactatct cccaagacac ccatgagttt   3720
tctaagacag tttgtcccag agcccaggtc cagaatctag tcctggtctt ggatttggtc   3780
agaccttccc tcactctcac ctcaggactc cccaccactt ccccccctgc cccaggaacc   3840
catgggaatt acaggcataa attaaatacc tgatcctatg acagctccag agtatctgga   3900
atcttttttt ttttttttg agacagtgtc ttgctctgtc gcccaggctg gagtgcagtg   3960
gcgtgatctc tgctcactgc aagctccgcc tcctgggttc aggccattct tctgcctcag   4020
cctcccgagt agctgggact gcgagtgtcc atcaccacac ccagctaatt ttttgtact    4080
tttagtagac acggggtttc accttgttag ccatgatggt ttcactctcc tgacttcgtg   4140
atctgcccgc ttcagcctcc caaagtgctg gattacagg cgtgagccac cacgcccagc    4200
ccaagattta atttgttaaa aaaaaaaaa aaaaaaaaa aagtagggta aagacgctag     4260
aaagtctaga gaggaaggag ggattatttt acacaggatg gtcaggggag gccactttga   4320
taggtggcat ttagcagtga ggcttcctga actcagcatg actgctccgc ttggctcaga   4380
ttccagctct gtccactgta gttgaggaat tatccctaga cagagaatgg ggagataaag   4440
aggctcagct tgttaacagg ttcccctctc acatgaatct tttgtccact gcctcaaaac   4500
tgccccgata tagtttaatt tcgtagtatg ctattgtgtc atgctgcaac tctttcagct   4560
```

-continued

| | |
|---|---|
| ccaaaaggga tggcaccagg ttcaagaggc tgaagaagag actcagatcc aggaaatgag | 4620 |
| gcataggtta tatgtgagat ggaacttaca tacagagtgg tccagtggtg gtaggctgaa | 4680 |
| caggagaact gccaccgcct gcagaaagca tggactttgt atagcatttt cacttaatac | 4740 |
| tctcctccta acagcatcca catggcaacc ctcatttaac ccaagacaaa gagcctcagc | 4800 |
| ccccataggg ccagcgttcc acaggacagg ccagggactc atttaaccca agacaaagag | 4860 |
| ccttaatccc ctatagggcc cacgttccac aggacaggcc agggactcag gcatttatca | 4920 |
| tagataaaga tgaatctcca tgttggtcat atttggaact ccgaacatgt attcaggtgc | 4980 |
| gtctgccatg ctgggtcatt ttcagagtat gcttaagtta ttgctatcag tgtctaccat | 5040 |
| acacagttgg atctaccata catagttgca tctgccatat gctatgatag aaagacttgt | 5100 |
| ctagtacaag cttctgtatc atagcccata gcagaactca tatttgtgag tattgtttga | 5160 |
| agggattaag cagagagaat tgagtcagga tatcactggg gaggtataca gtttatttgt | 5220 |
| gggatttcaa gggcctgaat tgtgacaaca gaataaagtt cttgtgggag aaatattttc | 5280 |
| agaggatttg agagcatggt gttgaagagt taaggaaaca gcatatatct tttcgtgcta | 5340 |
| gatgcttaca tgcaaatgaa tctccttatg ctgtcacaaa tgtatgcttc tctctccctc | 5400 |
| cctttcactt atcagtcaca tcccactagt cctggagctt ctcctaccct gaggtcaggc | 5460 |
| atgaaccctg gtgtgtagtt ttgctcaaat gcttacgatc gataacccag ttgtgcacca | 5520 |
| ggtttcttta tatcttgaag ttatctactg aacacatgaa aaataaattc agcaaattat | 5580 |
| agaaactacg agacactgct gtctacccct tgacaaacat ttactcagtg ttgtgtgctg | 5640 |
| gcttatttgc attgtgtttt gcaaaagtct taaaatcaca gtcatatcta ggttttttc | 5700 |
| aagcaattct cctgcctcag cccccctgagt agctgggatt acaggcacct gccaccatgc | 5760 |
| ccggctaatt tttgtatttt tagtagagac agggtttcac catgttagcc aggttggtct | 5820 |
| tgaaatcctg gcctcgatgg tatacacatt cctatggaag gcaagcatta tcttgtgagg | 5880 |
| tacatagctg atatgatgct tctgcatggt cttcaaagaa gggggggcctt atctttcaag | 5940 |
| aaactgaatg aaactcttct taaagcaaaa ataaggctaa agagaatatg actgtttaag | 6000 |
| atctacaact tcatctgctt atatgtccca tctccggtcc taaagccaac tcttcctca | 6060 |
| tcaagggtcc aactttggct tgggagactt gtgtagttga gaaattgagc ctgagtcacc | 6120 |
| tcttccaata agtgcatatg ctcggacttg agctctgcct gccctctgac tgcaagagat | 6180 |
| gacagtttct ttaaatgctc cttttgatat tcacgcttta gaatgctgat taaggtatct | 6240 |
| gagattgtta ttttctctgc tctttgcatt agtagcactt tttaaaaggc acctattcca | 6300 |
| cagtcctaat ggttgctatt tctgctgtac taatcaaagg ctagaggtac tgcacatggc | 6360 |
| agggcattct tctgcaccta tatcccatca cagtatataa tcttagcaat tgtactgtga | 6420 |
| aagctggcca ggagctgtct gtccttttga tgtccgtttc cttgatgctt agtgatatag | 6480 |
| agcatttctc atatacctgc ttgccatttg tgtgtcttat tttgagaagt atctattcag | 6540 |
| gtttttcc attttaaaat cagattattt agttttttgc tatcgaattg agttccttac | 6600 |
| atattctgaa tattaatccc ttgttagatg catggtttgc aaattactct ttcccaatct | 6660 |
| gtaggttgtc tctttacctg cccaaggctt atggctgcca gtgaattgat ttgaggctgc | 6720 |
| ctgccagtga attgatttag ggctgaggcc atttagtca gccagcagtg aagtggtctg | 6780 |
| ggacatggga ccctcctgtg tgggtggcag attctcttct ggcctggggt ggatctaaaa | 6840 |
| tctctgttca tggccaccat tctgtactca ggggccttga ggttctgccc agtgctgtgt | 6900 |
| tttactgtgg cagggcaagt acttgtacca tgcacgtttc cctctccttc ctttaaggcc | 6960 |

| | |
|---|---|
| ttccgtgcta tgctgcctag ggttggaaga agggaggtga ggccagtggg agagtatcct | 7020 |
| tcttactgtc ttcaattgtc tttccttgtt atgctaagac caggtactgt gatctttcat | 7080 |
| ctagtttcct tagctcttgt gaatatattt tcttgcatgg atagttgttg aaatttattt | 7140 |
| tcctgcctgg gggtttgctg aagtgttcct tcctgccatc ttgctccacc tctctgttcc | 7200 |
| ttgacctttt ctagtgacca tgtcttctac cccatcagcc actcaactaa aagattaccc | 7260 |
| cacctgtgtt tcattaataa tgtatgtatt tccaccatca tttcaatgtc acatatctat | 7320 |
| attttaagaa aatgtgcatt agcagctact ccatttccac agtacttcaa ctcgagaatt | 7380 |
| acaattgagt gatctacctt catcttacta tcccttttcct ctcatgagct aatttacttc | 7440 |
| atagcccaca ttgagatgct gaaattaatt actttagtca ctttaattac tttagtcact | 7500 |
| tctttgcatt ttttgctaga gagaattcat ctgataaaca ctaatcccaa gtaaactcaa | 7560 |
| ctttaaacat gacaggagat gaaaccagaa aaccttgctt acttatctct ctttaacctt | 7620 |
| aatgtccact tacaccaaga cttgttgcct gagaaaacat cataccttat atttctgctt | 7680 |
| taccttcagt agcttcttcc aatcttctct ttcatccgat gaccttgagg cacatttaat | 7740 |
| gagtaaacca ggatgggtca ggaagaagtt ccacatttcc caacaggaca atcatcccc | 7800 |
| tgcccctcc cattactgtg gatgagctgt ccatgttcct gctgaagggc aaccactcat | 7860 |
| ctgaggctca cttttctcac tgctttgctt acttgctcag ggtgtagctc taataattat | 7920 |
| gagcattgtc tgctgtaata attatgagca ttgtctgctc taataattat gagcattgtc | 7980 |
| ttccacataa ttttcctact ctcttaaatc attctagaat aataaaaatg ttctggaatt | 8040 |
| tcccttaatt taaaaacact gttactctaa gtcatgcata ctctttaaac aactccccca | 8100 |
| tttctctgtt ccccatttca gaaaagatcc taaaaagagt agtctttgtt ctttgtctgt | 8160 |
| ggctccttga taacattttt ccttgaacac actgggcctc taacgccacc attgaaattg | 8220 |
| ctcttataaa tgtcaccaaa agttgtccat gatgctaaat taaggatca attagtcctt | 8280 |
| cttctaccta aatctttacc aagatgtgag gttgctgatg aacccccat ccttgaacct | 8340 |
| cttttattt ggccatttga tgattgacac catcattttc cacgtggatt acttcaacaa | 8400 |
| cttgttaact cattctgtca cttttttata gtcatgtatt cttaacatat caggtagatt | 8460 |
| aattttataa aaccttaagt cagatcatgt tctggtctcc tttaacttct ccagcgactt | 8520 |
| tctacctcac aaagaataga atccagattc ctcacaatgg cctagacaac tctaatgaaa | 8580 |
| ccccacactg tgatctctca gattccactt tagtcccact ggcctcctgt gttcttcctc | 8640 |
| aaacgtggct ggtttgcttc cacatcaagg ttttgtacat tgctgttcgt ttacctggaa | 8700 |
| tgctcttccc ttggggagcc cagcaaatag gtcaatatca tcctctcctt gaggtcttcc | 8760 |
| caaccacccc attgtagact gcaggttgaa aatggaatct tcccaccctg tgaagtcagc | 8820 |
| aacctcattc tttccagtgc ccactgtgtg gtgagcatgt ttaggcttta ttacagggtc | 8880 |
| tcagatgaag gtttgacctg taataagtca catgtctgcc ctctgttttt ctccataggg | 8940 |
| gttctattca gcctctttgg tgggataaac attccttatt ttcagtatat gtgaagaaag | 9000 |
| actcactcca cagggctagg gcctagatca gcactgtgag cagaagaaac tctctaagaa | 9060 |
| gaaaacgtga gagtgctcta catgatgaac aatatctaga aaatgagtgt ggccaggcct | 9120 |
| ggcacggtgg ctcatgcctg taatcccagc actttgggag gccgaggcgg gcggatcatg | 9180 |
| aggtcaggag atcaagacca tcctggccaa cacagtgaaa ccccgtctct actaaaaata | 9240 |
| caaaaaatta gccaggcgtg gtggcaggcg cctgtagtcc cagctactcg ggaggctgag | 9300 |

```
gcaggagaat ggcgtgaacc cgggaggtgg agcttgcagt gatccgagat tgcaccactg    9360
cactccagcc tgggcaacag agcgagactc cgtctcaaaa aaaaaaaaaa aaaaagagtg    9420
tggccagagg ccagatggtt tcccaagata tacactattc attaacaatg ctctgttttc    9480
agaagtcttc ttcataatct taaaaatact ccatttctta gtcattcaaa gtcatgagcc    9540
acttatgtta ttttataaag tcaaatattt ttcttgtctc atgtcttagt gtatcaatag    9600
aagaagggaa attcagtctt tatttctttc acatcctaat actagaactc ttaccttttc    9660
tcatgaacca tcctttactg tgatgcatat agttatcaag tacccattta tggctagtgt    9720
tccattattg gaatgctaag catgtgggag ttatatccta ctgttcaagt cattgccaag    9780
gtctgattgc agaaattcaa aaaattgcaa cctcaggcat aaatggtaag gaatagttgc    9840
tcattttatt atctttcatg gtctggaagg atgtgtgctt aatgacttga gttcagttct    9900
tctgggctta gtttcttgcc cagtaattgg ctgattatct ctacactggc tcttatgtcc    9960
taggatgaga accacaagag agaggacatg agggtaaata caatggggaa aagaaaaca    10020 aacagtggca gcagagaatg aagatgagga ggaaagaaaa aatgagaaat aggaagagaa    10080
tgagtttgtt atgctcgtct ggcaaacgtg taatctgaat aaatgataga gaatagtgtt    10140 tataagaaa tgctcttcag aggcaaatag actgttttaaa tgccgttaga tctgagtgtc    10200
cttgatacat tcttagcctg aaaactagag gaacatgggc tggcaaacca acactgacat    10260
aaataaacgg caaggaatat taaaaagaa aacaagtttt gagagctacg ggaacatata    10320
actttaggat attaattatt tcagaaaagg cttttatgaa gtagtgaatt ttttcattc    10380 tttcttgaat agttttattt ttaaataagt ttggattacc aaagagctgc agagatggta    10440
cagagtttct atatacacat tccccagctt tccttaatgc taccatcata tagaaccatg    10500
gtaccttagt caacctaaaa ccttcacatt ggtacaatac tctcagagaa actgcagact    10560
attcagattt ccactgtttt tccaagtatt atctttttta gttccaggtt ctagtcacaa    10620
atctcacatt tctttaagcc atcatgtccc ttagtctact tgggtctgca atgattcctc    10680
agtctttatc ttttatgacc ttgtcactca tcaggatttt tatcaaatgt ccctcagttt    10740
gagtttgtgt gacttttgtg tgtgtgtgat tagtctgagg gtatgaattt ttagggagat    10800
tatatgctag ataatttaa gctgttttgt aaagaattag tcaaatcaat gcaaggacac    10860
cataaatttt tctagcagaa gaaacagcaa cagcatagat ggtgagtggg aaatgattat    10920
ggtgtatttt acctcttta atccaactta aatctctaag atagagctat ctttcaacca    10980
aaatgaccag ctttcctaat tttgtatatc acccatgtaa atggactaga acagaaatga    11040
tagattcccc agttttccct cttttatttt cttctctacc ccataaatgg ttattaactg    11100 actcttgtg agatttgcaa aacagttctt tagagtggga ttgtcccaac cactctgagc    11160
aagggacaag aaaccaaga gaggctagaa cagtaggttt cacaatagac gaaaactgcc    11220
acctgagttc agacacagag atatactcct ctcttctcat cctgtaaaac tcaaaccttg    11280
gttccccttg aggagagccc ggcctttagc tgccccaatg cacattgact gaactttaag    11340
ctctatttca gccacttttg atggcaccca tccctttctg tgcatgtctt tgaatattga    11400
cgtgctccat ccttgctgga atccaatttc ctgtcaatct tggaatatat aaatacttct    11460
tgctccattt ttgaagcccc ctcaaagccc catcttcctt cccacccatt cctgacactg    11520
cctctgggtt tctagaattc atcaaaattt tccctagaat tgttgatagc cctcagcatg    11580
tatatgttaa gctcttcctc aatacatgca tgaaatgttg ccagaggaaa taagaaaatt    11640
gaataaataa catttgccac ctaactggaa caatgaagaa aaggcagaca gcgaccatcc    11700
```

```
ttgatcttct cactgggata acctttgaat gggacagtgg aatagaacca ttaatggagg    11760
gaagatagct gtgaaatggt gtgaaagaga gtgaattttg gggaaagatg gttacctgat    11820
gcagttcctc acatgctact atcaggacat tctttttttcc tctcatttgt agccagccat   11880
gagtgtggtc ataccatgag tcatgagtca ctgtgagaaa gatgaggaaa agaggtgatg    11940
ggtttgattg tctgcacagt tgcagcccac tgtatgcatg ccataagtag ttaaggagca    12000
catgggtgaa gtgaatggaa atccttttcc cttttttctc atttgcaaga gaatagaat    12060 tctgcccta ctgcctagat acaaggcagc aggtgctgtg tgagatcgag tattgaagat     12120
aagtttcacc tctacctgtg aagtggattt tcaattatga agaaaattca gttagcaaat    12180
ataggagcta aacttcattg ttctttttttt tttgaagtca atgactttgt tgtttctatc   12240
atgaatttag ttgctttctc ttatgccaga aaatgatgta attaatggct gctaacacat    12300
gttttttgct tatcttctac ccaccaagaa ggttttcct cacatttgca ctgtattcag     12360
atgactgtgg ctggaggggt catgtctcaa gggatcctgt tacttggata ttgttgacat    12420
atagtgtggg gcatctgaca catgcacacc agcatctccc cttgatattt ttagtcttca    12480
tatcaagagt aaacttgctg tttctctctg taaatctgga cagtaaaata gaagaactaa    12540
tattcaggaa tggtcagctt gctttcgggt catacgtaat agaaacctat gctgaaacat    12600
aaaaagtgaa acattcaagc agaaaagtgc agagattgag ggaattctgt ttgattccac    12660
tgctccagct cattctaagg aggtcgagtt gaattcttat gtaggattca ttgaaaaagc    12720
atagtgtttt cataattgcc cttttgctca aattatttac atttaatatt tcttgcaact    12780
aaaggtttgg cataattcag taaaagctat ggctgtggac atgatggtgc tgaagtgcaa    12840
ataatgaagt gatctgctca attccatgta gatcatatac cccaagaact tcaaatacca    12900
aagtggatgc ttttaaaaat cttacaataa agatgccaag tattttaca ttttttttta     12960 atttttattt tttgagacag aaccgtgctc tgtcatccag gctggagtgc agtggcatga    13020
tcttggctca ttgcaacctc actgcctctc aggttcaagc tcttctcctg cctcagcctc    13080
ccaagtagct gggattacat gtgcccacca ccatgcacgg ctaatttttt tgtattttta    13140
gtaaagacgg ggtttcacca tgttagccag gctggtcttt aactcctgac ctcaagtgat    13200
ccgcctgcct tagcctccca aattgctagg attacaggtg tgagccactg cacccagcca    13260
gagatgctaa gtattttgt aacatggagc agctctgaac actttggtca ataagaaaat     13320
tgaggctcgt agaagttaaa ccattcttct gctgaaaata gctagtaaaa ggttgaataa    13380
tcgctgtttg aatgccgaca ttgggacctc tgagaggaga gcatttatgc aggaacatgc    13440
tagatcatgg actttgggag catgttatgc tgctatagca aaaattgtac tagttaaaaa    13500
tatggttact ccatgaatta caaggtaatc tcacaagatg ccagataatt gcacaagctg    13560
gcagaaagaa aaatgatgtt ttaaattttt tattttttggc atgatagcct ttaaaaataa    13620
cttttatgga agtccaccct ttaaaaacaa tattttaaaa aattgaaata caggttaaat    13680
ttgaagctct ttaatatagt gattaaagct gcacatgatg ttgaccatgc agatattagt    13740
accttaatgc cttcaccaca cctaactccc atcctggttc taagctgtac cagcttttct    13800
cacctcatgc agtttcctga gtttgtcctt cagcttggtt ccttggtagc ctagtctaca    13860
ggttttcttt tatatcttat ttttttttaag ttaacaatgg atcctggagg ccactgtgcg   13920
gtgatgtggc agtattccct attcctgttt taagttgggt actattccag aatattgtca    13980
gtggcaattt tggttctttc ttgtttgcta tttcaagtaa agaacatttg aatagttttg    14040
```

-continued

```
taaatccatc ttttttttgtg tttttgcttt tgtacttctt ctgtttgata agggggaatt    14100
ctgcatgaac atgtaactgc aggaacgtga gaatttgcaa acttttccta catagattta    14160
tgtcattttc catctaacca ccaatatatg agcatgcctg tctatgagag tctcaccact    14220
agggtgattg gaatgatctg aatgctagct gtggtaggca gcaggtcccc cagtacacac    14280
acaccaaaga tgtccatatc ctaatcctca aatctgtgaa tgtgttactt ttcatagcgc    14340
aagtgacttt gaaggtgtga ttaaagaatc ttcagatggg gagattatct tggcctatcc    14400
agctggagac agtgtaatca aagggtcat tttaagaggc aggcataagt ggcaaaagca    14460
gagaaagaga tgtgatgaca agaaggatgt ggccatgtga cgaagtgagg gcagcctcta    14520
gaagctagaa aaggcaagag gtagatcctc tcctggagcc tcaggaatgg caggtagcta    14580
ggcccacaga ttaattttag ctcataagac atattttgga attctgaact gcagaacatg    14640
gcagtttaaa caaaactgct tagttttaac tgctgtattt gtggtaattc atcacagcag    14700
agagaaacta atgaacctcc tagtgtgata ggtgagaaat ggtatctcgg tgtggtttga    14760
attacacttc tcttattttg agtatggtaa gttgtatttt taaatggtca cagcacttag    14820
aataatttgg agggacaaag catgttcact gagattctgt tgctaactgg aggtaccaga    14880
gatttaacca acacctaggt ttggagggca aaatttgttt aaaccatgag acagtaagac    14940
ctggacgtag aaactccacc attcttctag gaaccctat tttgagtcat agtcaccatg    15000
tccttgaaga aaccattcaa aatattcttc agatgactct ggatttttga ccatccttat    15060
tgctctccag aaatagtaac tagaaataac agcatctctg ggatttctca ctatgtaaat    15120
aatcgtaaat gaaaagggg atattgagaa taaatatatc catttccttt gctccaggat    15180
ttttgcaagt ggataaaaaa atttaactca cattagagtc tttggctgta gctcagcctt    15240
ctttaaatca ttcatttaac aaaatgtatt gagaacctac tatgtgctag acatacagct    15300
ataatggatc aatgaaagaa gtctgcgtcc gagtcctctg tacatttatg gctaagggct    15360
gggctgtaca ggcatggggc aagatcacca gaattttacc aaatagtagt gacttctaac    15420
agcttcttaa cactcctgtt atctagctga gtcattgaaa gcagccagct acaaacagac    15480
acattccagg cagtggagaa agaggagaaa aatgcccccct aacttctcat cagaaaaaca    15540
aaggcctaat gaaaatggaa agttgtcttt aaagtgctga agggggaaaa aaaaccttca    15600
tgctaaatat gcttcacgta tgaggatgaa ctcaaggtaa tcttagaaac atgaaagctg    15660 tgagaatta ttgctgtcag ctctacacga caacgaattc taaagtcctt cagtctgtga    15720
ggaatcatag tgtatgtcaa gggggaagga aggaagaagc caagaaacag taaaggagta    15780
aatttaaaag acattttctt tcctcttcca attaacttaa aagacagctg agtgtttaaa    15840
gcaaaataac cccgtagaca gtttttgcaa tgtagataag agtgaaaatt gtgagggaaa    15900
tagtacaaag aaagatggtg ggtaaatgga atcagttaat aactccagat tttctcctcg    15960
ttcagcttga caaagtcacc aaatcctcca tctgcataac tccatcagta aacactgcat    16020
ttaatctcct gggacaacca atactttttc tgtattttttc tccctgcctc accctcttta    16080
cctatctatg atatttctta aaatagatgt tttcaccaac tgcaccctgg gatctgatac    16140
taagctaggc tgtcagtaaa tgatattgtc accacagaaa ccaagtatat gtctactctt    16200
tgtcgtgccc aaatacaaat ctgtaaattc ccttaatatg tgggttgggg tcatcttaat    16260
catcaccttt ttctcaatcc tgtttcagag cctgacacat gataggtgca taatacttaa    16320
atgtatgaag gaataaaagg catgaatgca tacataagtt aattaataat cagaagtgag    16380
tacatggaag aatcagtact gccagtttaa acacacagaa actgtgcttc aaagacgctg    16440
```

```
cactatttgc cagtagacaa aatgtggaac caaggttcaa actggaattt tctgagataa    16500
agtcacaatc atattacaga gcttggtctt gggctgtttg cttgggctat ttgttttctt    16560
tttcatttat tcatcctata ttttcttaaa tctctacaac gttttaagca ctttgccaaa    16620
ttagtataaa acagtaaaaa tagtaagata ataaacatgg tcttcataat catggatgtc    16680
acggtaaaat gaatcagcct gacagtaagt aagccagcaa atgaaacata gcacagtagt    16740
aatacaatgt gatagcataa tactgtaata ccttttttt ttttttcctt ttcttgagat     16800
ggagtctcta tctgttgcct aggctggagt gcagtgccgt gatctcggct cactgcaacc    16860
tctgcctccc aggttcaagc gattctcctg cctcaacctc ccgggtagct gggattacag    16920
gcatgtgcca ccatgccctg ctaattttg tatttttcat agagatgggg tttcatcatg     16980
ttggccaggc tggtctcaaa ctcctgacct caggtgatct gcccaccttg gcctcccaaa    17040
gtactgggat tacaggtgtg agccatcaca cctggcctat aatatcttga taatactgct    17100
actaccacat cacctaagat gcttcaaggg agtttcatac agttttgatg gttttaatgc    17160
catatgattt aaactataat ctatgatgag tacacattca cattttatag cacagggtca    17220
ctcaatgcta gaggttttat gtagagctcc tgaaatgatg catctgagtc ctttcagctg    17280
ggaaagacat ggtctgaata ggtaatatca tggttagaaa aacccaattg ggtttcacat    17340
gtgagtacca aacctatatt tcctctcaaa tagaggtact ggcttataat tgaggtgctt    17400
cccacatggg cttgtcaaca ttgggtgcct ctgtgttgag ggtgcagcca ggatttataa    17460
aactgaagac tgaatattct ctggggcaat accaggcaga ttctcttgta tatgacattg    17520
tagcttagaa caagattttc taatctgctt actttactga atcacatttt aagtttgttt    17580
ctaaaacaaa gatattgagg gcagtcagaa aagtagtcca catggacatt cttttttttt    17640 ttttttgag acggagtctc actctgttat gcaggctgga gtgcagtggc gcaatctcgg    17700
ctcactgcaa cctccgcctt ctgggttcaa gcgattctcc tgcctcagcc caccaagtag    17760
ctgtgccacc acaccccggct aatttttttg tatttttagt agaaatgggg ttttaccatg   17820
ctagccagga tggtctcgat ctcctgacct cgtgatctgc acacctcggc ctcccaaagt    17880
gctgggatta caggcgtgag caccatgcct ggtggacatt ccattattaa ctcaccttgg    17940
ccttggaatt aatgacttgg agaagacctg aatgggagg ggagagcagt agaagcatga     18000
gcctttctga ctgtctacat gttcttgccc agttttaact tctagtcatg gcgaatgatc    18060
gcaggagagc acagactgga ccctgctacg atctctcttg gagtggatca gactgatgat    18120
caccaacaac caactcattc ccggataagg aagaagagag tgtcacctac ttcagtgtgg    18180
tttcaaccct acttctgcat cttaaagaca ctgtatggtt tcagcagtag tgcccctgtt    18240
cattagtccc cctgatgttt tcattcctca tctcatcttt ttcttagcag cattcaatga    18300
atccttcatt ctagaaacac tctatatctt tggttttcat gagaccattc tcaccttgtt    18360
ttgtcctgtg acttttttga aaaaacaaa aacaaaaaac ccttttttc ttttttaaatt     18420 ctggtaaaaa acacaatgaa aatttgctat cttaaccatg ttgaaatgtg cagttagtaa    18480
agtacattca cattgtggtg caagccatca ctaccatcca tcactagaac ccttttcatc    18540
ttgcagatct gaaactctac ccattaaacg acttcccatc ttcccatccc cacagctcct    18600
agcaaccaac attctacttt ctctatcagt ttgactactc taggtacctc atatgagtag    18660
aatcatacag catttatcct tctctgcctg gcttatttca cttgtataat gtcctcaagg    18720
ttcattcatg ttgtagcatg catcagaact tcctccccctt ttaaaggctg gataatattt    18780
```

-continued

| | |
|---|---|
| catggtatgt ttagatcaca ttctgtttat ccattcatcc atcagtgaac acttgtgctc | 18840 |
| cttccaactt tgggctgttg ggtgtcctgc cactgttgct cctagtgctc aatctcgttt | 18900 |
| attccctcct aatcaagtgt acaacgttgg acactgtgca ggatgatgcc acttcatctt | 18960 |
| ggatgctaat ctgccatgtt gacttctgat taacccagg cccaggaatg cctcaagatt | 19020 |
| tctactttac ttactgttgc ttgtgtaagc caagacaacc ttgatgttat cataaacatg | 19080 |
| tacttaccta agtcctgtcc tttggcaaat tatgggctat gagacacagc attcttgcct | 19140 |
| ttccctgagg ggtcaatttc agcgatccta cacattcctt ctgaagcact tatgctcttt | 19200 |
| ctatatggta tgtaagctct cggtctgggg agtaacagtg cagagatcta cctgtcttgt | 19260 |
| tgccacatgt ttctaaactt tccaataaat caccttctac tgacaaactg gatttgtctt | 19320 |
| ccttattctt tggtttcttg gttccttttt ggtatggatt tgctttccct atgtggttct | 19380 |
| ttcatgaaac tgttggtgag ctagccagga ggaattcagg agccaaagta tgggcaaggg | 19440 |
| aaggaagcct cagttgggga agtcttgggg cagccctctg tgtgtgtggg gtgatattgc | 19500 |
| ccgtttgctg gatgcctgca gaccaccgcc tgagtacggg gatggcccag aacactacag | 19560 |
| ggtctagagt gcttgtgaga agaaaaccac accatgcact gaaggtccct gaaggtggca | 19620 |
| acagagggt ggccgctatt atgggttgca catgtgaccc cagaagtaca gttagcaacc | 19680 |
| gagacaaagg tacagaagct agagaagtaa ttacagttag agaaggatat gaggatctcc | 19740 |
| acatctgtgt tagcatctaa tttggtgcat aagcttgaaa ctcaggaggt gcaggtggaa | 19800 |
| actgttgtct gccgctttta tgcagctgcg aggacaaaaa ctgcactggt tgcaagtgtg | 19860 |
| agctgtcctt gctagaccag accaagatgc tgagacctgg aatccttggg aatcgacttg | 19920 |
| tgagtcagat gaagacagag gttatctcag agtaggagga ttgtcctccc cttttgaggg | 19980 |
| caggaggaaa acaaaaccca acagatacag ctgtacaata gcaagcagtc ttttcacagc | 20040 |
| aaagcttaac tctgagagta caccctcagca gaactattgg acacagcaag aactcttaaa | 20100 |
| gcagctgcca agagacagca tagccacatg gatggtggtg tggctatgcg agaggcccag | 20160 |
| tgaaggggac ttcccaggtc agacactggc atggtggtct ctggaggagg cacagagcaa | 20220 |
| ttcaggggag ctgggtatgc agcaggccat ctatgaccag cagttgcagt tgtccccttg | 20280 |
| taggacaaga tgtatattat gtgcgggatg ccgtagctgg tcttggagaa actgaaaggg | 20340 |
| gaagggataa ggtccaactg gttaccaagg gaaaagaaaa ggagatagca agtctgttgg | 20400 |
| acttgaaaaa ggaggtctaa aagacccagt taggattacc agaaaacaaa tgtggtacaa | 20460 |
| tctgatctca gctgggataa accaagaaac ggaatcagca a | 20501 |

<210> SEQ ID NO 2
<211> LENGTH: 1695
<212> TYPE: DNA
<213> ORGANISM: Artificial sequence
<220> FEATURE:
<223> OTHER INFORMATION: Synthetic nucleic acid

<400> SEQUENCE: 2

| | |
|---|---|
| actacatttc ccaacggccc ctgcacgccc tgggggctgt tccatgcggt gttgcgcctg | 60 |
| cgtagccggc gggctggcag tgagactgac tgcgtcgggg ttgagactgg gtggatgagg | 120 |
| ctcaccccgg cggggagaag ggacgaggag gggcggacag cggaaggtcc gggagtgtcc | 180 |
| gccataaagt cgtttgaggt gaccgttgcg taattgtgag tctgtgagag aagatgtgaa | 240 |
| gtatggcctc gtcccggtca tctgggcgtg cgggtcccgg gttttgatcg cgcgtttgtg | 300 |
| tagttttaac ttctagtcat ggcgaatgat cgcaggagag cacagactgg accctgctac | 360 |

-continued

```
gatctctctt ggagtggatc agactgatga tcaccaacaa ccaactcatt cccggataag      420
gaagaagaga gtgtcaccta cttcagtgtg gtttcaaccc tacttctgca tcttaaagac      480
actgtatggt tcagcagta gtgcccctgt tcattagtcc ccctgatgtt ttcattcctc       540
atctcatctt tttcttagca gcattcaatg aatccttcat tctagaaaca ctctatatct      600
ttggttttca tgagaccatt ctcaccttgt tttgtcctgt gacttttttg aaaaaaacaa      660
aaacaaaaaa cccttttttt cttttaaat tctggtaaaa aacacaatga aaatttgcta       720
tcttaaccat gttgaaatgt gcagttagta aagtacattc acattgtggt gcaagccatc      780
actaccatcc atcactagaa ccctttcat cttgcagatc tgaaactcta cccattaaac       840
aacttcccat cttcccatcc ccacagctcc tagcaaccaa cattctactt tctctatcag      900
tttgactact ctaggtacct catatgagta gaatcataca gcatttatcc ttctctgcct      960
ggcttatttc acttgtataa tgtcctcaag gttcattcat gttgtagcat gcatcagaac     1020
ttcctcccct tttaaaggct ggataatatt tcatggtatg tttagatcac attctgttta     1080
tccattcatc catcagtgaa cacttgtgct ccttccaact ttgggctgtt gggtgtcctg     1140
ccactgttgc tcctagtgct caatctcgtt tattccctcc taatcaagtg tacaacgttg     1200
gacactgtgc aggatgatgc cacttcatct tggatgctaa tctgccatgt tgacttctga     1260
ttaaccccag gcccaggaat gcctcaagat ttctacttta cttactgttg cttgtgtaag     1320
ccaagacaac cttgatgtta tcataaacat gtacttacct aagtcctgtc ctttggcaaa     1380
ttatgggcta tgagacacag cattcttgcc tttccctgag gggtcaattt cagcgatcct     1440
acacattcct tctgaagcac ttatgctctt tctatatggt atgtaagctc tcggtctggg     1500
gagtaacagt gcagagatct acctgtcttg ttgccacatg tttctaaact ttccaataaa     1560
tcaccttcta ctgacaaact ggatttgtct tccttattct ttggtttctt ggttcctttt     1620
tggtatggat ttgctttccc tatgtggttc tttcatgaaa ctgttggtga gctagccagg     1680
aggaattcag gagcc                                                      1695
```

```
<210> SEQ ID NO 3
<211> LENGTH: 37
<212> TYPE: DNA
<213> ORGANISM: Artificial sequence
<220> FEATURE:
<223> OTHER INFORMATION: Synthetic nucleic acid

<400> SEQUENCE: 3
aggaagagag tggttttgtt ttttattttt ttaggag                                37

<210> SEQ ID NO 4
<211> LENGTH: 56
<212> TYPE: DNA
<213> ORGANISM: Artificial sequence
<220> FEATURE:
<223> OTHER INFORMATION: Synthetic nucleic acid

<400> SEQUENCE: 4
cagtaatacg actcactata gggagaaggc tcaaataaat ccccactatt aaccaa           56

<210> SEQ ID NO 5
<211> LENGTH: 35
<212> TYPE: DNA
<213> ORGANISM: Artificial sequence
<220> FEATURE:
<223> OTHER INFORMATION: Synthetic nucleic acid
```

```
<400> SEQUENCE: 5
aggaagagag ttggttaata gtggggattt atttg                               35

<210> SEQ ID NO 6
<211> LENGTH: 57
<212> TYPE: DNA
<213> ORGANISM: Artificial sequence
<220> FEATURE:
<223> OTHER INFORMATION: Synthetic nucleic acid

<400> SEQUENCE: 6
cagtaatacg actcactata gggagaaggc ttcctcacac atattcaaaa taacaca      57

<210> SEQ ID NO 7
<211> LENGTH: 1578
<212> TYPE: RNA
<213> ORGANISM: Artificial sequence
<220> FEATURE:
<223> OTHER INFORMATION: Synthetic nucleic acid

<400> SEQUENCE: 7
acuacauuuc caacggcccc ugcacgcccc uggggcugu uccaugcggu guugcgccug     60
cguagccggc gggcuggcag ugagacugac ugcgucgggg uugagacugg guggaugagg   120
cucaccccgg cggggagaag ggacgaggag gggcggacag cggaaggucc gggagugucc   180
gccauaaagu cguuugaggu gaccguugcg uaauugugag ucugugagag aagaugugaa   240
guauggccuc gucccgguca ucugggcgug cgggucccgg guuugaucg cgcguuugug    300 uaguuuuaac uucuagucau ggcgaaugau cgcaggagag cacagacugg acccugcuac   360
gaucucucuu ggaguggauc agacugauga ucaccaacaa ccaacucauu cccggauaag   420
gaagaagaga gugucaccua cuucagugug guuucaaccc uacuucugca ucuuaaagac   480
acuguauggu ucagcaguag ugcccccugu cauuaguccc ccugauguu ucauuccuc     540 aucucaucuu uuucuuagca gcauucaaug aauccuucau ucuagaaaca cucuauaucu   600
uugguuuuca ugagaccauu cucaccuugu uuugccugu gacuuuuug aaaaaaacaa     660 aaacaaaaaa cccuuuuuuu cuuuuuaaau ucugguaaaa aacacaauga aaauuugcua   720
ucuuaaccau guugaaaugu gcaguuagua aaguacauuc acauguggu gcaagccauc    780 acuaccaucc aucacuagaa cccuuuucau cuugcagauc ugaaacucua cccauuaaac   840
aacuucccau cuucccauuc ccacagcucc uagcaaccaa cauucuacuu ucucuaucag   900
uuugacuacu cuagguaccu cauaugagua gaaucauaca gcauuuaucc uucucugccu   960
ggcuuauuuc acuguauaa uguccucaag guucauucau guuguagcau gcaucagaac   1020 uuccucccu uuuaaaggcu ggauaauauu ucaugguaug uuuagaucac auucuguuua   1080
uccauucauc caucagugaa cacuugugcu ccuuccaacu ugggcuguu ggguguccug   1140 ccacuguugc uccuaugcu caaucucguu uauccccucc uaaucaagug uacaacguug   1200
gacacugugc aggaugaugc cacucaucu uggaugcuaa ucugccaugu ugacuucuga   1260
uuaaccccag gcccaggaau gccucaagau uucuacuuua cuuacuguug cuuguguaag   1320
ccaagacaac cuugauguua ucauaaacau guacuuaccu aagucctguc cuuuggcaaa   1380
uuaugggcua ugagacacag cauucuugcc uuucccugag gggucaauuu cagcgauccu   1440
acacauuccu ucugaagcac uuaugcucuu ucuauaugu auguaagcuc ucgguucggg    1500
gaguaacagu gcagagaucu accugucuug uugccacaug uuucuaaacu uuccaauaaa   1560
ucaccuucua cugacaaa                                                1578
```

```
<210> SEQ ID NO 8
<211> LENGTH: 1597
<212> TYPE: RNA
<213> ORGANISM: Artificial sequence
<220> FEATURE:
<223> OTHER INFORMATION: Synthetic nucleic acid

<400> SEQUENCE: 8
acuacauuuc ccaacggccc cugcacgccc uggggcugu uccaugcggu guugcgccug      60
cguagccggc gggcuggcag ugagacugac ugcgucgggg uugagacugg guggaugagg    120
cucaccccgg cggggagaag ggacgaggag gggcggacag cggaaggucc gggagugucc    180
gccauaaagu cguuugaggu gaccguugcg uaauugugag ucugugagag aagaugugaa    240
guauggccuc gucccgguca ucugggcgug cgggucccgg guuugaucg cgcguuugug     300 uaguuuuaac uucuagucau ggcgaaugau cgcaggagag cacagacugg acccugcuac    360
gaucucucuu ggaguggauc agacugauga ucaccaacaa ccaacucauu cccggauaag    420
gaagaagaga gugucaccua cuucagugug guuucaaccc uacuucugca ucuuaaagac    480
acuguauggu uucagcagua gugcccugu ucauuaagucc cccugauguu uucauuccuc    540
aucucaucuu uuucuuagca gcauucaaug aauccuucau ucuagaaaca cucuauaucu    600
uugguuuuca ugagaccauu cucaccuugu uuuguccugu gacuuuuug aaaaaaacaa     660 aaacaaaaaa cccuuuuuuu cuuuuuaaau ucgguaaaa aacacaauga aaauugcua      720 ucuuaaccau guugaaaugu gcaguuagua aaguacauuc acauuggu gcaagccauc      780 acuaccaucc aucacuagaa cccuuuucau cuugcagauc ugaaacucua cccauuaaac    840
aacuucccau cuucccaucc ccacagcucc uagcaaccaa cauucuacuu ucucuaucag    900
uuugacuacu cuagguaccu cauaugagua gaaucauaca gcauuuaucc uucucugccu    960
ggcuuauuuc acuuguauaa uguccucaag guucauucau guugucagcau gcaucagaac   1020 uuccucccu uuuaaaggcu ggauaauauu ucaugguaug uuuagaucac auucuguuua     1080
uccauucauc caucagugaa cacuugugcc ccuccaacu uggggcuguu ggguguccug     1140
ccacuguugc uccagugcu caaucucguu uauucccucc uaaucaagug uacaacguug     1200 gacacgugc aggaugaugc cacuucaucu uggaugcuaa ucugccaugu ugacuucuga     1260
uuaaccccag gcccaggaau gccucaagau uucuacuuua cuuacuguug cuuguguaag    1320
ccaagacaac cuugauguua ucauaaacau guacuuaccu aagccuguc cuuuggcaaa     1380 uuaugggcua ugagacacag cauucuugcc uuucccugag gggucaauuu cagcgauccu    1440
acacauuccu ucugaagcac uuaugcucuu ucuauauggu auguaagcuc ucggucuggg    1500
gaguaacagu gcagagaucu accugucuug uugccacaug uuucuaaacu uuccaauaaa    1560
ucaccuucua cugacaaaaa aaaaaaaaaa aaaaaa                              1597
```

NON-CODING RNAS LINKED TO IMMORTALITY AND ASSOCIATED METHODS AND COMPOSITIONS

CROSS-REFERENCE TO RELATED APPLICATIONS

This application claims the benefit of U.S. Provisional Patent Application Ser. No. 62/238,029, filed Oct. 6, 2015, and is related to U.S. patent application Ser. No. 14/505,491, filed Oct. 2, 2014, which applications are incorporated herein by reference in their entireties.

STATEMENT OF GOVERNMENTAL SUPPORT

This invention was made during work supported by U.S. Department of Energy under Contract No. DE-AC02-05CH11231 and by the Margaret E. and Fenton L. Maynard Endowment for Breast Cancer Research and Center grants ES006694, CA23074, CA65662, P42 ES04940. The government has certain rights in the invention.

INTRODUCTION

Immortality is an essential characteristic of human carcinoma cells. We recently reported the development of an efficient and reproducible method that immortalizes human mammary epithelial cells (HMEC) by targeting two critical senescence barriers[1]. This immortalization method uses agents pathologically relevant to breast carcinogenesis, works with HMEC from all individuals tested, and produces transformed lines that reflect the various phenotypes seen in clinical breast cancer[1,2]. The first senescence barrier, stasis (stress-associated senescence), is bypassed by disrupting the RB pathway such as by inhibiting p16 function using a p16-directed shRNA or by constitutively overexpressing cyclin D1. These post-stasis cells are then made to bypass the second proliferation barrier, replicative senescence due to critically shortened telomeres, by transduction of a dysregulated c-MYC. Importantly, this controlled genetic approach produces non-clonal immortalized cell lines lacking gross genomic alterations[1, 2]. Thus, these immortal cells carry minimal confounding passenger errors, thereby providing a unique system to identify important and still unknown participants in breast cancer immortalization.

SUMMARY OF THE INVENTION

Aspects of the present disclosure include RNAs that confer a mortal phenotype and nucleic acids encoding same. Liposomes, cells, and pharmaceutical compositions that include the RNAs or nucleic acids encoding same are also provided. Further provided are methods involving quantifying the RNAs and/or determining the methylation status of the MORT promoter, as well as methods that employ the RNAs or nucleic acids encoding same.

According to certain embodiments, provided is a nucleic acid encoding a ribonucleic acid (RNA) comprising the ribonucleotide sequence set forth in SEQ ID NO:7, or a variant RNA thereof that confers a mortal phenotype. In certain aspects, the nucleic acid is operably linked to a promoter. The promoter may be a heterologous promoter, e.g., a constitutive, inducible, tissue-specific, or other heterologous promoter. Also provided is an expression vector that a nucleic acid of the present disclosure. An RNA encoded by a nucleic acid of the present disclosure (which may be present in an expression vector of the present disclosure) is also provided. In certain aspects, the RNA is transcribed/expressed from a nucleic acid or expression vector of the present disclosure.

Also provided are liposomes. In certain aspects, a liposome of the present disclosure includes any of the nucleic acids, expression vectors, and/or RNAs of the present disclosure.

The present disclosure also provides a recombinant cell (e.g., a recombinant host cell) that includes any of the nucleic acids, expression vectors, and/or RNAs of the present disclosure. In certain aspects, the recombinant cell is present in a container. In other aspects, the recombinant cell is present in a subject. According to certain embodiments, the subject (e.g., a primate subject, such as a human subject) has been identified as having a disease or disorder associated with cell immortalization.

Also provided are pharmaceutical compositions that include any of the nucleic acids, expression vectors, RNAs, recombinant cells, and/or liposomes of the present disclosure. Such compositions further include a pharmaceutically acceptable carrier.

Methods are also provided. In certain aspects, provided is a method that includes quantifying a level of a MORT RNA in a biological sample obtained from a subject. According to certain embodiments, the quantifying is performed by quantitative reverse transcription polymerase chain reaction (qRT-PCR). In certain aspects, the quantifying is performed by next-generation sequencing, microarray analysis, RNAse protection assay, northern blot analysis, or fluorescence in situ hybridization (FISH). According to certain embodiments, the biological sample is a fluid sample. In certain aspects, the biological sample is a tissue sample. According to certain embodiments, the tissue sample is premalignant lesion. Premalignant lesions of interest include, but are not limited to, a ductal carcinoma in situ (DCIS) lesion. The methods may further include, prior to the quantifying, obtaining the biological sample from the subject. In certain aspects, the methods further include identifying the subject as having a disease or disorder associated with cell immortalization when the quantified level of the MORT RNA is below a threshold level.

The present disclosure also provides methods that include determining the methylation status of the MORT promoter in a biological sample obtained from a subject. According to certain embodiments, the biological sample is a fluid sample. In certain aspects, the biological sample is a tissue sample. According to certain embodiments, the tissue sample is premalignant lesion. Premalignant lesions of interest include, but are not limited to, a ductal carcinoma in situ (DCIS) lesion. The methods may further include, prior to the determining, obtaining the biological sample from the subject. In certain aspects, the methods further include identifying the subject as having a disease or disorder associated with cell immortalization based on the determining.

Also provided are treating a disease or disorder associated with cell immortalization by administering to the subject a therapeutically effective amount of a pharmaceutical composition, e.g., a pharmaceutical composition of the present disclosure. Such methods may be stand-alone methods, or may be combined with other methods of the present disclosure, such as the present methods that include quantifying a level of a MORT RNA, the present methods that include determining the methylation status of the MORT promoter, and/or the like.

Methods for reversing immortalization in a cell are also provided. Such methods include introducing into an immortalized cell any of the nucleic acids, expression vectors, and/or RNAs of the present disclosure.

Also provided are methods for immortalizing a cell. Such methods include introducing into a non-immortalized cell an agent that reduces MORT RNA levels in the cell. In certain aspects, the agent is a MORT small interfering RNA (siRNA).

In one embodiment, a long non-coding RNA MORT that is linked to immortality and epigenetically-silenced in most common human cancers having a sequence of SEQ ID NO:2, operably linked to a promoter.

In one embodiment, methods of using MORT sequences described herein to detect abnormal levels of MORT expression in a primary tissue, solid tumor, tissue biopsy, or other bodily substances and fluids (e.g. blood, excreta, saliva), from a subject for the detection or monitoring of cancer growth, progression or evolution, or response to therapy (chemical, biological, or physical).

In another embodiment, methods of using MORT sequences described herein to detect abnormal levels of MORT DNA methylation in primary tissue, solid tumor tissue, tissue biopsy, or other bodily substances or fluids (e.g. blood, excreta, saliva), from a subject for the detection or monitoring of cancer growth, progression or evolution, or response to therapy (chemical, biological, or physical). In other embodiments, methods of using MORT gene constructs to express MORT lncRNA or MORT lncRNA molecules themselves either in their natural form produced by primate cells or in various chemically-modified forms that enhance RNA stability, penetration, potency, or therapeutic efficacy. These chemical modifications to the native MORT nucleic acid include, but are not limited to, for example, morpholino or "locked nucleic acid" modifications, which are used to increase or modulate in vitro or in vivo MORT RNA expression.

In another embodiment, delivery of MORT lncRNA to an organism or subject where MORT expression is at abnormal levels. Delivery of MORT lncRNA is contemplated to require in vivo delivery vehicles or administration methods as is known in the art.

In another embodiment, smaller RNA sequences derived from the full-length or spliced MORT lncRNA sequence that are still capable of performing MORT function. These smaller RNA fragments may act as contact points with other cellular RNAs (e.g. mRNAs and miRNAs) or proteins (e.g. PCBP-1) that functionally mimic full-sized or spliced MORT RNA.

In another embodiment, provided are methods for administration of a cytidine analog such as 5-aza-2'-deoxycytidine (5-AdC) to a subject to reactivate MORT expression.

In one embodiment, methods of using "anti" MORT sequences to block and eliminate MORT function to stimulate cell proliferation and tissue regeneration are provided.

BRIEF DESCRIPTION OF THE DRAWINGS

FIG. 11A is a plot of MORT transcript level in a cohort of 27 breast carcinomas and 8 breast non-tumor samples as determined by Affymetrix microarray. FIG. 11B is a plot of MORT expression in the large cohort of TCGA breast invasive carcinoma data. FIG. 11C is a plot of MORT promoter DNA methylation in the large cohort of TCGA breast invasive carcinoma data.

FIG. 15 depicts a table showing genes with at least two fold mean expression change after the first genetic modification that led to bypassing stasis.

FIG. 16 depicts a table showing genes with significant expression change after the second genetic modification, which led to immortalization.

FIG. 17 depicts a table showing genes whose expression were significantly changed after multiple testing.

FIG. 18 depicts a table showing a list of MassARRAY primers.

FIG. 19A is a plot of cell population doublings versus time for untreated immortal, HMEC 184Dp16sMY, and those transduced with eGFP, MORT-Null, and MORT-Exact. FIG. 19B shows photomicrographs of untreated and transduced cells after assaying for senescence-associated β-galactosidase expression.

DETAILED DESCRIPTION

Figure 1:
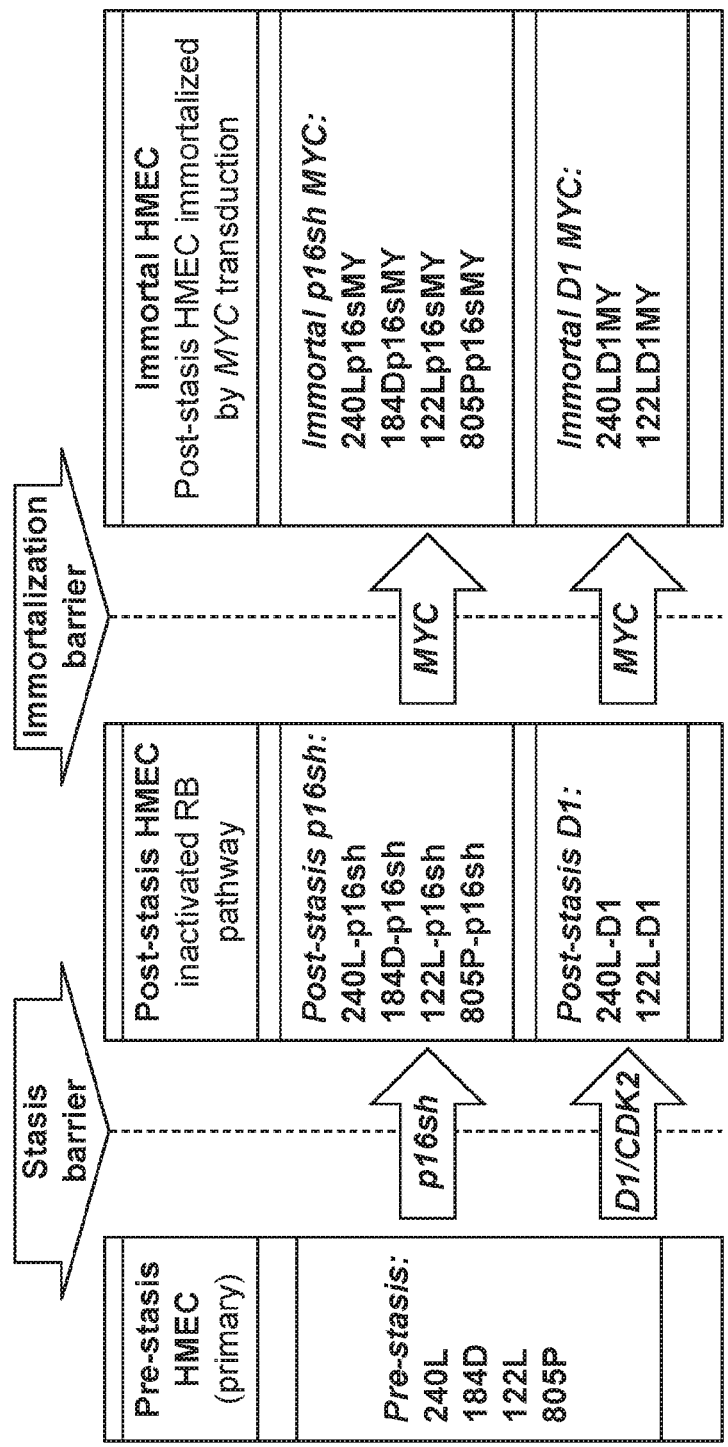
FIG. 1 is a scheme of the in vitro HMEC immortalization model and analyzed samples. HMEC from four different individuals were immortalized in vitro. The stasis barrier was bypassed by either targeting p16 using p16sh RNA or overexpression of a ccnd1/CDK2 fusion gene. The immortalization barrier was bypassed by transduction of c-MYC.

As shown herein, a long non-coding RNA (lncRNA) designated "MORT" is expressed in all normal finite lifespan human cells examined to date and is down-regulated or lost in immortalized HMEC. MORT silencing during immortalization is linked to the aberrant epigenetic event of DNA hypermethylation of its CpG island promoter. This epigenetic silencing is also seen in human breast cancer cell lines and in a majority of human breast tumor tissues. The functional importance of DNA hypermethylation in MORT gene silencing is supported by the ability of 5-aza-2'-deoxycytidine (5-AdC) to reactivate MORT expression. Furthermore, analysis of TCGA data across 16 additional human cancers revealed that deregulation of MORT expression due to DNA hypermethylation is a frequent event in most common human cancers. Together these results identify a lncRNA whose epigenetic silencing is likely involved in the immortalization of human epithelial cells and the progression of multiple human cancer types.

Aspects of the present disclosure include RNAs that confer a mortal phenotype and nucleic acids encoding same. Liposomes, cells, and pharmaceutical compositions that include the RNAs or nucleic acids encoding same are also provided. Further provided are methods involving quantifying the RNAs and/or determining the methylation status of the MORT promoter, as well as methods that employ the RNAs or nucleic acids encoding same.

Nucleic Acids, Expression Vectors, Cells and Liposomes

As summarized above, aspects of the present disclosure include RNAs that confer a mortal phenotype and nucleic acids encoding same. In certain aspects, the present disclosure provides a nucleic acid encoding a ribonucleic acid (RNA) that includes the ribonucleotide sequence set forth in SEQ ID NO:7, or a variant RNA thereof that confers a mortal phenotype. In the context of the present invention, "encodes" or "encoding" is meant that an RNA transcribed/expressed from the nucleic acid either includes the ribonucleotide sequence set forth in SEQ ID NO:7 (the sequence of a wild-type MORT RNA), or is a variant RNA thereof that confers a mortal phenotype (a functional variant MORT RNA).

In certain aspects, the nucleic acid is (or includes) a complementary deoxyribonucleotide (cDNA) that encodes the RNA. According to certain embodiments, the nucleic acid is a genomic DNA (e.g., including introns) that encodes the RNA. In certain aspects, the nucleic acid is non-naturally occurring (that is, does not occur in nature). According to certain embodiments, the nucleic acid is an isolated nucleic acid. By "isolated nucleic acid" is meant the nucleic acid is not present in its native (e.g., genomic) environment, e.g., has been removed from its native environment. Examples of isolated nucleic acids include, but are not limited to, recombinant DNA molecules (e.g., contained in a vector), recombinant DNA molecules maintained in a heterologous host cell, partially or substantially purified nucleic acid molecules, and synthetic nucleic acid molecules.

The RNA sequence of SEQ ID NO:7 is provided in Table 1 below.

TABLE 1

| MORT RNA (SEQ ID NO: 7) | ACUACAUUUCCCAACGGCCCCUGCACGCCCUGGGGGCUG UUCCAUGCGGUGUUGCGCCUGCGUAGCCGGCGGGCUGGC AGUGAGACUGACUGCGUCGGGGUUGAGACUGGGUGGAU GAGGCUCACCCCGGCGGGGAGAAGGGACGAGGAGGGGCG GACAGCGGAAGGUCCGGGAGUGUCCGCCAUAAAGUCGUU UGAGGUGACCGUUGCGUAAUUGUGAGUCUGUGAGAGAA GAUGUGAAGUAUGGCCUCGUCCCGGUCAUCUGGGCGUGC GGGUCCCGGGUUUUGAUCGCGCGUUUGUGUAGUUUUAA CUUCUAGUCAUGGCGAAUGAUCGCAGGAGAGCACAGACU GGACCCUGCUACGAUCUCUCUUGGAGUGGAUCAGACUGA UGAUCACCAACAACCAACUCAUUCCCGGAUAAGGAAGAA GAGAGUGUCACCUACUUCAGUGUGGUUUCAACCCUACUU CUGCAUCUUAAAGACACUGUAUGGUUUCAGCAGUAGUG CCCCUGUUCAUUAGUCCCCUGAUGUUUUCAUUCCUCAU CUCAUCUUUUUCUUAGCAGCAUUCAAUGAAUCCUUCAUU CUAGAAACACUCUAUAUCUUUGGUUUUCAUGAGACCAU UCUCACCUUGUUUUGUCCUGUGACUUUUUUGAAAAAAA |

TABLE 1-continued

```
CAAAAACAAAAAACCCUUUUUUUCUUUUUAAAUUCUGG
UAAAAAACACAAUGAAAAUUUGCUAUCUUAACCAUGUU
GAAAUGUGCAGUUAGUAAAGUACAUUCACAUUGUGGUG
CAAGCCAUCACUACCAUCCAUCACUAGAACCCUUUUCAU
CUUGCAGAUCUGAAACUCUACCCAUUAAACAACUUCCCA
UCUUCCCAUCCCCACAGCUCCUAGCAACCAACAUUCUAC
UUUCUCUAUCAGUUUGACUACUCUAGGUACCUCAUAUGA
GUAGAAUCAUACAGCAUUUAUCCUUCUCUGCCUGGCUUA
UUUCACUUGUAUAAUGUCCUCAAGGUUCAUUCAUGUUG
UAGCAUGCAUCAGAACUUCCUCCCCUUUUAAAGGCUGGA
UAAUAUUUCAUGGUAUGUUUAGAUCACAUUCUGUUUAU
CCAUUCAUCCAUCAGUGAACACUUGUGCUCCUUCCAACU
UUGGGCUGUUGGGUGUCCUGCCACUGUUGCUCCUAGUGC
UCAAUCUCGUUUAUUCCCUCCUAAUCAAGUGUACAACGU
UGGACACUGUGCAGGAUGAUGCCACUUCAUCUUGGAUGC
UAAUCUGCCAUGUUGACUUCUGAUUAACCCCAGGCCCAG
GAAUGCCUCAAGAUUUCUACUUUACUUACUGUUGCUUG
UGUAAGCCAAGACAACCUUGAUGUUAUCAUAAACAUGU
ACUUACCUAAGUCCUGUCCUUUGGCAAAUUAUGGGCUAU
GAGACACAGCAUUCUUGCCUUUCCCUGAGGGGUCAAUUU
CAGCGAUCCUACACAUUCCUUCUGAAGCACUUAUGCUCU
UUCUAUAUGGUAUGUAAGCUCUCGGUCUGGGGAGUAAC
AGUGCAGAGAUCUACCUGUCUUGUUGCCACAUGUUUCUA
AACUUUCCAAUAAAUCACCUUCUACUGACAAA
```

An example nucleic acid that encodes a ribonucleic acid (RNA) that includes the ribonucleotide sequence set forth in SEQ ID NO:7 is a nucleic acid that is (or includes) the nucleotide sequence set forth in SEQ ID NO:2.

A further example nucleic acid that encodes a ribonucleic acid (RNA) that includes the ribonucleotide sequence set forth in SEQ ID NO:7 is a nucleic acid that is (or includes) the nucleotide sequence set forth in SEQ ID NO:1.

As will be appreciated, RNAs transcribed from a particular nucleic acid may differ at their 5' ends (e.g., due to transcription being initiated at different possible start sites), their 3' ends (e.g., because of the presence or absence of a polyA tail or variations in length thereof), or both.

By "functional variant" is meant that the RNA differs in sequence, length, or both, as compared to a MORT RNA having the ribonucleotide sequence set forth in SEQ ID NO:7, but retains the ability to confer a mortal phenotype. In certain aspects, a functional variant MORT RNA has a ribonucleotide sequence that has 70% or greater, 75% or greater, 80% or greater, 85% or greater, 90% or greater, 95% or greater, or 99% or greater identity to a MORT RNA having the ribonucleotide sequence set forth in SEQ ID NO:7 or a fragment thereof, such as a fragment having a length of from 1 to 20, 1 to 30, 1 to 40, 1 to 50, 1 to 60, 1 to 70, 1 to 80, 1 to 90, 1 to 100, 1 to 150, 1 to 200, 1 to 250, 1 to 300, 1 to 350, 1 to 400, 1 to 450, 1 to 500, 1 to 550, 1 to 600, 1 to 650, 1 to 700, 1 to 750, 1 to 800, 1 to 850, 1 to 900, 1 to 950, 1 to 1000, 1 to 1050, 1 to 1100, 1 to 1150, 1 to 1200, 1 to 1250, 1 to 1300, 1 to 1350, 1 to 1400, 1 to 1450, or 1 to 1500 nucleotides. Accordingly, the present disclosure provides such variant MORT RNAs and nucleic acids encoding such variants.

Determining whether a variant MORT RNA is a functional variant may be accomplished using any suitable approach. For example, a variant MORT RNA or nucleic acid encoding and configured to express same may be introduced into a cell having a mortal phenotype (e.g., a mortal epithelial cell, such as a mortal human epithelial cell, e.g., a mortal human mammary epithelial cell), followed by subjecting the cell to conditions that would immortalize the cell in the absence (or downregulation) of full-length wild-type MORT RNA. An example of such conditions are those described in Garbe et al. (2014) Cell Cycle 13(21):3423-3435. If the cell maintains a mortal phenotype, the variant MORT RNA is functional variant. Alternatively, a variant MORT RNA or nucleic acid encoding and configured to express same may be introduced into an immortal cell (e.g., an immortal cell produced as described in Garbe et al. (supra)), and reversion of the cell to a mortal phenotype indicates that the variant MORT RNA is functional variant. The variant MORT RNA or nucleic acid encoding same (e.g., present in an expression vector) may be introduced into cells of interest using suitable cell transformation or cell transfection approaches known in the art. An example approach is described in Example 2 below.

Variant MORT RNAs may be generated using any of the various available strategies including, but not limited to, known recombinant DNA and/or site-directed mutagenesis approaches for generating a variant MORT cDNA from which the variant MORT RNA may be transcribed/expressed. The variant MORT cDNA may be cloned into an expression vector suitable for transcribing the variant MORT RNA in vitro or in a cell type of interest, e.g., in which the variant MORT cDNA is operably linked to a promoter (e.g., a heterologous promoter) suitable for expression in vitro or in the desired cell type.

Accordingly, aspects of the present disclosure include expression vectors (linearized or circular) that include any of the nucleic acids described herein. Expression of natural or synthetic nucleic acids encoding the RNAs of the present disclosure can be achieved by operably linking a nucleic acid encoding an RNA to a promoter (which may be either constitutive or inducible), and incorporating the construct into an expression vector to generate a recombinant expression vector. The vectors can be suitable for replication and integration in prokaryotes, eukaryotes, or both. Typical cloning vectors contain functionally appropriately oriented transcription terminators, initiation sequences, and promoters useful for regulation of the expression of the nucleic acid encoding the RNA. The vectors optionally contain generic expression cassettes containing at least one independent terminator sequence, sequences permitting replication of the cassette in eukaryotes and/or prokaryotes, e.g., as found in shuttle vectors, and selection markers for prokaryotic and/or eukaryotic systems. Suitable expression vectors are typically replicable in the host organisms either as episomes or as an integral part of the host chromosomal DNA. The expression vector may include a selection marker (e.g., ampicillin-resistance, hygromycin-resistance, tetracycline resistance, kanamycin/neomycin resistance, blasticidin resistance, puromycin resistance, or the like) to permit detection of those cells transformed/transfected with the desired DNA sequences.

Once a nucleic acid encoding a subject MORT RNA is isolated and cloned, a MORT RNA of the present disclosure can be produced by in vitro transcription. For example, the nucleic acid encoding a subject MORT RNA can be cloned into a vector such that the nucleic acid is operably linked to an RNA polymerase promoter (e.g., a T3, T7, SP6, or other RNA polymerase promoter). The vector can be linearized, purified, and serve as the promoter and template for an in vitro transcription reaction that includes ribonucleotide triphosphates, a buffer system (e.g., a buffer system that includes DTT and magnesium ions), and an RNA polymerase appropriate for the promoter. Detailed protocols and kits for cDNA cloning and in vitro transcription of an RNA of interest are available and include, e.g., the MEGAscript® and the mMESSAGE mMACHINE® families of in vitro transcription kits available from Ambion, the HiScribe™ family of in vitro transcription kits from New England Biolabs, etc. If desired, the RNA transcription products may be purified using an RNA purification column (e.g., a spin column), ethanol precipitation, and/or the like.

According to certain embodiments, once a nucleic acid encoding a subject MORT RNA is isolated and cloned, the clone may be introduced into a cell for expression in a variety of recombinantly engineered cells known to those of skill in the art. Examples of such cells include bacteria, yeast, filamentous fungi, insect (e.g., those employing baculoviral vectors), and mammalian cells.

*Escherichia coli* is an example of a prokaryotic host cell that can be used for cloning a polynucleotide encoding a MORT RNA. Other microbial hosts suitable for use include bacilli, such as *Bacillus subtilis*, and other enterobacteriaceae, such as *Salmonella, Serratia*, and various *Pseudomonas* species. In these prokaryotic hosts, one can also make expression vectors, which will typically contain expression control sequences compatible with the host cell (e.g., an origin of replication). In addition, any number of a variety of well-known promoters will be present, such as the lactose promoter system, a tryptophan (trp) promoter system, a beta-lactamase promoter system, or a promoter system from phage lambda. The promoters will typically control expression, optionally with an operator sequence, and have ribosome binding site sequences and the like, for initiating and completing transcription and translation.

Other microbes, such as yeast, are also useful for expression. *Saccharomyces* (e.g., *S. cerevisiae*) and *Pichia* are examples of suitable yeast host cells, with suitable vectors having expression control sequences (e.g., promoters), an origin of replication, termination sequences and the like as desired. Typical promoters include 3-phosphoglycerate kinase and other glycolytic enzymes. Inducible yeast promoters include, among others, promoters from alcohol dehydrogenase, isocytochrome C, and enzymes responsible for maltose and galactose utilization.

In addition to microorganisms, mammalian cells (e.g., mammalian cells grown in in vitro cell culture) can also be used to express the MORT RNAs of the present disclosure. Suitable mammalian host cells include CHO cell lines, various Cos cell lines, HeLa cells, myeloma cell lines, and the like. Expression vectors for these cells can include expression control sequences, such as an origin of replication, a promoter, and an enhancer, and necessary processing information sites, such as polyadenylation sites, and transcriptional terminator sequences. Examples of suitable expression control sequences are promoters derived from SV40, adenovirus, bovine papilloma virus, cytomegalovirus and the like.

Accordingly, aspects of the present disclosure include recombinant cells (e.g., recombinant host cells) that include any of the expression vectors, nucleic acids, or MORT RNAs (that is, a wild-type MORT RNA or a functional variant thereof) described herein. In certain embodiments, a recombinant cell of the present disclosure is present in a container. Suitable containers include, but are not limited to, a tube, a vial, a well of a plate (e.g., a tissue culture plate, a 96-well plate, etc.), or the like. In other embodiments, the recombinant cell is present in a subject. In certain aspects, the recombinant cell is present in a subject that has been identified as having a disease or disorder associated with cell immortalization. In certain embodiments, the disease or disorder associated with cell immortalization is cancer or a precancerous condition.

Also provided by the present disclosure are liposomes that include any of the expression vectors, nucleic acids, or MORT RNAs described herein. Such liposomes find use, e.g., in therapeutic applications where it is desirable to deliver any of the expression vectors, nucleic acids, or MORT RNAs described herein to a target cell (e.g., a target immortalized cell) in a subject, e.g., a subject having a disease or disorder associated with cell immortalization.

Liposomes are closed amphiphilic lipid bilayer systems that have gained attention as a carrier system for therapeutically active agents, owing to their unique characteristics, including biocompatibility, bio-degradability, low toxicity, lack of immune system activation, and capability to incorporate both hydrophilic and hydrophobic drugs. Liposomes have shown therapeutic potential as carriers for payloads and for delivery to targeted sites, which has led to several liposomal formulations designed for the clinic and clinical trials for cancer therapy. Liposomal drug delivery systems improve the pharmacokinetic and pharmacodynamic profiles of the therapeutic payload, promote controlled and sustained release of drugs and exhibit lower systemic toxicity compared with the free drug. Various amphiphilic lipids can form bilayers in an aqueous environment to encapsulate a nucleic acid-containing aqueous core as a liposome. These lipids can have an anionic, cationic or zwitterionic hydrophilic head group. Some phospholipids are anionic whereas other are zwitterionic and others are cationic. Suitable classes of phospholipid include, but are not limited to, phosphatidylethanolamines, phosphatidylcholines, phosphatidylserines, and phosphatidyl-glycerols. Useful cationic lipids include, but are not limited to, dioleoyl trimethylammonium propane (DOTAP), 1,2-distearyloxy-N,N-dimethyl-3-aminopropane (DSDMA), 1,2-dioleyloxy-N,Ndimethyl-3-aminopropane (DODMA), 1,2-dilinoleyloxy-N,N-dimethyl-3-aminopropane (Dlin DMA), 1,2-dilinolenyloxy-N,N-dimethyl-3-aminopropane (DLenDMA). Zwitterionic lipids include, but are not limited to, acyl zwitterionic lipids and ether zwitterionic lipids. Examples of useful zwitterionic lipids are DPPC, DOPC, DSPC, dodecylphosphocholine, 1,2-dioleoyl-sn-glycero-3-phosphatidylethanolamine (DOPE), and 1,2-diphytanoyl-sn-glycero-3-phosphoethanolamine (DPyPE). The lipids in the liposomes of the present disclosure can be saturated or unsaturated.

A liposome may include an amphiphilic lipid whose hydrophilic portion is PEGylated (that is, modified by covalent attachment of a polyethylene glycol). This modification can increase stability and prevent non-specific adsorption of the liposomes. Lipids can be conjugated to PEG using known techniques. PEG provides the liposomes with a coat which can confer favorable pharmacokinetic characteristics. Various lengths of PEG can be used e.g. between 0.5-8 kDa.

Techniques for preparing suitable liposomes, including the preparation of liposomes suitable for in vivo delivery of DNAs and RNAs, are known in the art, e.g., see US 2013/0189351; Templeton, N. S. (2004) Liposomal Delivery of Nucleic Acids *In Vivo, DNA and Cell Biology* 21(12): 857-867; Maclachlan et al. (2007) Liposomal Formulations for Nucleic Acid Delivery (DOI: 10.1201/9780849387951.ch9); Faneca et al. (2013) Cationic Liposome-Based Systems for Nucleic Acid Delivery: From the Formulation Development to Therapeutic Applications; Shim et al. (2013) Application of cationic liposomes for delivery of nucleic acids, *Asian Journal of Pharmaceutical Sciences* 8(2):72-80. One suitable method involves mixing (i) an ethanolic solution of the lipids (ii) an aqueous solution of the nucleic acid and (iii) buffer, followed by mixing, equilibration, dilution and purification. Liposomes of the present disclosure are obtainable using this mixing process.

A liposome of the present disclosure may include a targeting ligand on its surface, e.g., to target the liposome to a particular cell type (e.g., a cancer cell type) upon administration of the liposome to a subject in need thereof. In certain aspects, the targeting ligand is a ligand (e.g., an antibody) that specifically binds a tumor-associated or tumor-specific cell-surface molecule (e.g., antigen). Such cell surface molecules include, but are not limited to, HER2, CD19, CD22, CD30, CD33, CD56, CD66/CEACAM5, CD70, CD74, CD79b, CD138, Nectin-4, Mesothelin, Transmembrane glycoprotein NMB (GPNMB), Prostate-Specific Membrane Antigen (PSMA), SLC44A4, CA6, CA-IX, an integrin, C—X—C chemokine receptor type 4 (CXCR4), cytotoxic T-lymphocyte-associated protein 4 (CTLA-4), neuropilin-1 (NRP1), and matriptase.

Compositions

Aspects of the present disclosure include compositions that include any of the nucleic acids, expression vectors, MORT RNAs, liposomes, or cells described herein. In certain aspects, the composition is present in a container, such as a tube, vial, plate well, or the like.

In certain aspects, the compositions include a nucleic acid, expression vector, MORT RNA, liposome, or cell of the present disclosure present in a liquid medium. The liquid medium may be an aqueous liquid medium, such as water, a buffered solution, or the like. One or more additives such as a salt (e.g., NaCl, $MgCl_2$, KCl, $MgSO_4$), a buffering agent (a Tris buffer, N-(2-Hydroxyethyl)piperazine-N'-(2-ethanesulfonic acid) (HEPES), 2-(N-Morpholino)ethanesulfonic acid (MES), 2-(N-Morpholino)ethanesulfonic acid sodium salt (MES), 3-(N-Morpholino)propanesulfonic acid (MOPS), N-tris [Hydroxymethyl]methyl-3-aminopropanesulfonic acid (TAPS), etc.), a solubilizing agent, a detergent (e.g., a non-ionic detergent such as Tween-20, etc.), a nuclease inhibitor (e.g., a ribonuclease inhibitor), glycerol, a chelating agent, and the like may be present in such compositions.

Also provided are pharmaceutical compositions. The pharmaceutical compositions include a nucleic acid, expression vector, MORT RNA, liposome, or cell of the present disclosure, and a pharmaceutically acceptable carrier. The pharmaceutical compositions generally include a therapeutically effective amount of the nucleic acid, expression vector, MORT RNA, liposome, or cell. By "therapeutically effective amount" is meant a dosage sufficient to produce a desired result, e.g., an amount sufficient to effect beneficial or desired therapeutic (including preventative) results, such as a reduction in a symptom of a disease or disorder associated with a target cell or a population thereof (e.g., immortal target cells), as compared to a control. An effective amount can be administered in one or more administrations.

A nucleic acid, expression vector, MORT RNA, liposome, or cell of the present disclosure can be incorporated into a variety of formulations for therapeutic administration. More particularly, the nucleic acid, expression vector, MORT RNA, liposome, or cell can be formulated into pharmaceutical compositions by combination with appropriate, pharmaceutically acceptable excipients or diluents, and may be formulated into preparations in solid, semi-solid, liquid or gaseous forms, such as tablets, capsules, powders, granules, ointments, solutions, injections, inhalants and aerosols.

Formulations of the nucleic acid, expression vector, MORT RNA, liposome, or cell of the present disclosure suitable for administration to a subject (e.g., suitable for human administration) are generally sterile and may further be free of detectable pyrogens or other contaminants contraindicated for administration to a subject according to a selected route of administration.

In pharmaceutical dosage forms, the nucleic acid, expression vector, MORT RNA, liposome, or cell can be administered alone or in appropriate association, as well as in combination, with other pharmaceutically active compounds. The following methods and carriers/excipients are merely examples and are in no way limiting.

The nucleic acid, expression vector, MORT RNA, liposome, or cell can be formulated for parenteral (e.g., intravenous, intra-arterial, intraosseous, intramuscular, intracerebral, intracerebroventricular, intrathecal, subcutaneous, etc.) administration. In certain aspects, the nucleic acid, expression vector, MORT RNA, liposome, or cell is formulated for injection by dissolving, suspending or emulsifying the nucleic acid, expression vector, MORT RNA, liposome, or cell in an aqueous or non-aqueous solvent, such as vegetable or other similar oils, synthetic aliphatic acid glycerides, esters of higher aliphatic acids or propylene glycol; and if desired, with conventional additives such as solubilizers, isotonic agents, suspending agents, emulsifying agents, stabilizers and preservatives.

For oral preparations, the nucleic acid, expression vector, MORT RNA, liposome, or cell can be used alone or in combination with appropriate additives to make tablets, powders, granules or capsules, for example, with conventional additives, such as lactose, mannitol, corn starch or potato starch; with binders, such as crystalline cellulose, cellulose derivatives, acacia, corn starch or gelatins; with disintegrators, such as corn starch, potato starch or sodium carboxymethylcellulose; with lubricants, such as talc or magnesium stearate; and if desired, with diluents, buffering agents, moistening agents, preservatives and flavoring agents.

Pharmaceutical compositions that include the nucleic acid, expression vector, MORT RNA, liposome, or cell may be prepared by mixing the nucleic acid, expression vector, MORT RNA, liposome, or cell having the desired degree of purity with optional physiologically acceptable carriers, excipients, stabilizers, surfactants, buffers and/or tonicity agents. Acceptable carriers, excipients and/or stabilizers are nontoxic to recipients at the dosages and concentrations employed, and include buffers such as phosphate, citrate, and other organic acids; antioxidants including ascorbic acid, glutathione, cysteine, methionine and citric acid; preservatives (such as ethanol, benzyl alcohol, phenol, m-cresol, p-chlor-m-cresol, methyl or propyl parabens, benzalkonium chloride, or combinations thereof); amino acids such as arginine, glycine, ornithine, lysine, histidine, glutamic acid, aspartic acid, isoleucine, leucine, alanine, phenylalanine, tyrosine, tryptophan, methionine, serine, proline and combinations thereof; monosaccharides, disaccharides and other carbohydrates; low molecular weight (less than about 10 residues) polypeptides; proteins, such as gelatin or serum albumin; chelating agents such as EDTA; sugars such as trehalose, sucrose, lactose, glucose, mannose, maltose, galactose, fructose, sorbose, raffinose, glucosamine, N-methylglucosamine, galactosamine, and neuraminic acid; and/or non-ionic surfactants such as Tween, Brij Pluronics, Triton-X, or polyethylene glycol (PEG).

The pharmaceutical composition may be in a liquid form, a lyophilized form or a liquid form reconstituted from a lyophilized form, wherein the lyophilized preparation is to be reconstituted with a sterile solution prior to administration. The standard procedure for reconstituting a lyophilized composition is to add back a volume of pure water (typically equivalent to the volume removed during lyophilization); however solutions comprising antibacterial agents may be used for the production of pharmaceutical compositions for parenteral administration.

Methods

As summarized above, aspects of the present disclosure include methods. As demonstrated in the Examples section below, the present inventors found that MORT is expressed in cells having a mortal phenotype (that is, cells having a finite lifespan), while MORT expression is downregulated in 15 out of the 17 most common human cancers. Accordingly, in certain embodiments, provided are methods that include quantifying a level of a MORT RNA in a biological sample obtained from a subject. Such methods may include quantifying the level of MORT RNA alone, or may further include quantifying the level of expression of other analytes (e.g., other RNAs) such as p53 and/or the like.

The quantifying may be performed using any suitable approach, including but not limited to, quantitative reverse transcription polymerase chain reaction (qRT-PCR) using primers specific for cDNA reverse transcribed from the MORT RNA, next-generation sequencing (e.g., based on the number of sequencing reads obtained for the MORT RNA or fragments thereof), quantitative microarray analysis, RNAse protection assays, Northern blot analysis, fluorescence in situ hybridization (FISH), or the like. An example approach that employs qRT-PCR is provided in the Examples section below. The quantifying may include comparing the level of the MORT RNA to a reference RNA expressed in the sample, e.g., an RNA transcribed from a housekeeping gene (e.g., GAPDH or other suitable housekeeping gene), the expression levels of which do not vary substantially between cells having a mortal phenotype and immortalized cells. By way of example, if the quantifying is performed using qRT-PCR, the cycle threshold (Ct) for MORT may be normalized by comparing to the Ct value for the reference RNA (e.g., a housekeeping RNA, such as GAPDH).

The biological sample obtained from the subject may be any sample of interest and generally will include one or more cells suspected of being immortal or suspected of being susceptible to becoming immortal. Suitable samples include fluid samples, including but not limited to blood, serum, or plasma samples, or fluid samples such as excreta, cerebrospinal fluid (CSF), peritoneal fluid, pericardial fluid, pleural fluid, synovial fluid, urine, saliva, tears, semen, amniotic fluid, sputum, and the like, as well as fluids obtained from cysts, tumors, and the like.

According to certain embodiments, the biological sample is a tissue sample. Tissue samples of interest include, but are not limited to, primary tissue samples, solid tumor tissue samples, tissue biopsy samples, or the like.

In certain aspects, the tissue sample is a premalignant lesion (or "pre-cancerous" lesion). By "premalignant lesion" is meant morphologically atypical tissue which appears abnormal under microscopic examination, and in which cancer is more likely to occur than in its apparently normal counterpart. According to some embodiments, the premalignant lesion is carcinoma in situ (CIS). Many forms of CIS have a high probability of progression into cancer, and therefore removal may be recommended; however, progression of CIS is known to be highly variable and not all CIS becomes invasive cancer. Accordingly, in certain aspects, the present methods find use for prognosis with respect to whether or not a CIS will develop into cancer (e.g., invasive cancer), where the level of MORT RNA being below a threshold level indicates poor prognosis (e.g., a high likelihood that the CIS will become invasive cancer) and the level of MORT RNA being above the threshold level indicates that the likelihood of the CIS becoming invasive cancer is low.

The carcinoma in situ may be of the skin (e.g., Bowen's disease), of the colon (e.g., polyps), of the bladder (e.g., preinvasive papillary cancer), of the breast, etc. In certain aspects, the carcinoma in situ is of the breast and is selected from ductal carcinoma in situ (DCIS) or lobular carcinoma in situ (LCIS).

According to certain embodiments, the subject is a primate. For example, the subject may be a non-human primate. In certain aspects, the subject is a human subject. According to certain embodiments, the subject has, is suspected of having, or is at risk of developing cancer.

In certain aspects, the methods further include, prior to the quantifying, obtaining the biological sample from the subject. Suitable approaches for obtaining the biological sample will vary depending upon the type of sample. Samples that are primarily fluid in nature may be aspirated using a needle or other suitable aspirating device. Solid tissue samples may be excised, e.g., using a suitable cutting device (e.g., a scalpel), or any other suitable excision instrument.

According to certain embodiments, the methods further include, subsequent to the quantifying, identifying the subject as having a disease or disorder associated with cell immortalization when the quantified level of the MORT RNA is below a threshold level. In certain aspects, the disease or disorder associated with cell immortalization is cancer. According to some embodiments, the cancer is breast cancer, acute myeloid leukemia (AML), bladder cancer, colon cancer, head and neck cancer, kidney cancer, liver cancer, lung cancer, pancreatic cancer, cancer of the rectum, skin cancer, uterine cancer, or B-cell lymphoma. In certain aspects, the cancer is a cancer listed in Table 2.

If the subject is identified as having a disease or disorder associated with cell immortalization based on the quantified level of the MORT RNA being below a threshold level, the method may further include treating the disease or disorder associated with cell immortalization by administering to the subject a therapeutically effective amount of a pharmaceutical composition. In some embodiments, the pharmaceutical composition is any of the pharmaceutical compositions of the present disclosure, e.g., a pharmaceutical composition that includes any of the nucleic acids, expression vectors, MORT RNAs, liposomes, or cells of the present disclosure.

By "treating" or "treatment" is meant that at least an amelioration of the symptoms associated with the condition afflicting the subject is achieved, where amelioration is used in a broad sense to refer to at least a reduction in the magnitude of a parameter, e.g. symptom, associated with the condition being treated. As such, treatment also includes situations where the pathological condition, or at least symptoms associated therewith, are completely inhibited, e.g., prevented from happening, or stopped, e.g., terminated, such that the subject no longer suffers from the condition, or at least the symptoms that characterize the condition. Thus treatment includes: (i) prevention, that is, reducing the risk of development of clinical symptoms, including causing the clinical symptoms not to develop, e.g., preventing disease progression to a harmful state; (ii) inhibition, that is, arresting the development or further development of clinical symptoms, e.g., mitigating or completely inhibiting an active disease, e.g., so as to decrease tumor load, which decrease can include elimination of detectable cancerous cells (e.g. metastatic cancer cells); and/or (iii) relief, that is, causing the regression of clinical symptoms.

In practicing the methods, routes of administration (path by which the nucleic acid, expression vector, MORT RNA, liposome, or cell of the present disclosure is brought into a subject) may vary, where representative routes of administration for a subject nucleic acid, expression vector, MORT RNA, liposome, or cell are described in greater detail below. The nucleic acid, expression vector, MORT RNA, liposome, or cell can be administered systemically (e.g., by parenteral, intravenous, intramuscular, intrathecal, intraventricular, or subcutaneous administration) or locally (e.g., at a local tumor site, e.g., by intratumoral administration (e.g., into a solid tumor, into an involved lymph node in a lymphoma or leukemia, or by convection enhanced delivery, e.g., into the brain, e.g., as disclosed in US 20090209937), administration into a blood vessel supplying a solid tumor, etc.), into a body cavity or lumen, or into an organ. These different routes of administration may be carried out by injection or infusion.

Also provided by the present disclosure are methods that include determining the methylation status of the MORT promoter in a biological sample obtained from a subject. Methylation of cytosines allows the encoding of epigenetic information directly onto the DNA. In the human genome, methylated cytosines are found in CpG dinucleotides whose palindromic nature allows for the maintenance of methylation patterns by DNA methyltransferases following semiconservative replication of DNA. Regions of DNA with a relatively high CpG dinucleotide content are referred to as CpG islands. CpG islands are distributed in a non-random manner across the human genome and often span the promoter region and the first exon of protein coding genes. Methylation of individual promoter region CpG islands usually acts to turn off (silence) transcription by recruiting histone deacetylases thereby inducing the formation of inactive chromatin.

For the methods that include methods that include determining the methylation status of the MORT promoter, the types of samples and subjects may be the same or similar as those described above with respect to the methods involving quantifying MORT RNA levels. A variety of approaches are available for determining the methylation status of a promoter of interest. In one example, isolated genomic DNA from the sample obtained from the subject is digested with a restriction enzyme (e.g., with MseI), and the resulting DNA fragments may be incubated with the methylation binding protein MeCP2 (also known as MBP). The methylated DNA fragments may be isolated (e.g., using a spin column) and amplified with promoter specific primers. Agarose gel electrophoresis may be used to visualize the PCR products. The presence of a band on the gel indicates that a specific promoter is methylated in your genomic DNA sample. Kits for carrying out such a procedure are available and include the Promoter Methylation PCR Kit from Affymetrix.

Another example approach is methylation-sensitive high resolution melting (MS-HRM). Methylated DNA and unmethylated DNA acquire different sequences after sodium bisulfite treatment resulting in PCR products with markedly different melting profiles. HRM relies upon on the precise monitoring of the change of fluorescence as a DNA duplex melts Like many real-time PCR techniques, HRM utilizes the ability of certain dyes to fluoresce when intercalated with double-stranded DNA. Detailed guidance for performing MS-HRM to determine the methylation status of a promoter of interest may be found in, e.g., Wojdacz et al. (2007) *Nucleic Acids Res.* 35(6): e41; Dimitrakopoulos et al. (2012) *BMC Cancer* 12:486; and Wojdacz et al. (2008) *Nature Protocols* 3:1903-1908.

The methylation status of the MORT promoter may be determined using other methods, including bisulfite conversion followed by sequence analysis, e.g., classical sequence analysis, pyrosequencing, next-generation sequencing, or the like.

In addition, one may employ a MassARRAY system to determine the methylation status of the MORT promoter. According to one example, genomic DNA may be treated with bisulfite, followed by PCR amplification, in vitro transcription, cleavage at uracil residues, and analysis on a MALDI-TOF mass spectrometer. Further details may be found, e.g., in Clark et al. (2007) *Nucleic Acid Research* 35(18):e119. Primers which may be used for such MassArray analysis of the MORT promoter are provided in FIG. 18 as SEQ ID NOs:3-6.

As with the methods involving quantifying MORT RNA levels, the present methods that include determining the methylation status of the MORT promoter may further include, e.g., obtaining the sample from the subject, identifying the subject as having a disease or disorder associated with cell immortalization (in this context, based on a determination that the extent of MORT promoter methylation is such that the MORT gene is silenced), and/or treating the disease or disorder associated with cell immortalization by administering to the subject a therapeutically effective amount of a pharmaceutical composition, e.g., a pharmaceutical composition that includes any of the nucleic acids, expression vectors, MORT RNAs, liposomes, or cells of the present disclosure.

The present disclosure also provides methods for reversing immortalization in a cell. Such methods include introducing into an immortalized cell any of the nucleic acids, expression vectors, and/or MORT RNAs of the present disclosure. In certain aspects, such methods include culturing an immortalized cell of interest (e.g., in a cell culture dish), and transfecting the immortalized cell with the nucleic acids, expression vectors, and/or MORT RNAs. Detailed protocols and suitable transfection reagents and kits (with accompanying protocols) are readily available and include Effectene transfection reagent (Qiagen), Xfect transfection reagent (Clontech), Escort transfection reagents (Sigma-Aldrich), Universal transfection reagent (Sigma-Aldrich), DOTAP liposomal transfection reagent (Sigma-Aldrich), and the like. Upon introduction of the nucleic acids, expression vectors, and/or MORT RNAs into the cell, the cell is cultured and acquires a mortal (finite lifespan) phenotype as a result of MORT function in the cell.

According to certain embodiments, the immortalized cell is present in a subject, and the methods for reversing immortalization in a cell include administering a pharmaceutical composition of the present disclosure to the subject, such that the nucleic acids, expression vectors, and/or MORT RNAs of the present disclosure (e.g., naked or encapsulated in a liposome) are taken up by the immortalized cell. Suitable pharmaceutical compositions and routes of administration are detailed elsewhere herein.

Additional methods are provided, such as methods for immortalizing a cell. Such methods may include introducing into a cell having a mortal phenotype an agent that reduces MORT RNA levels in the cell. The agent may be a small molecule, a protein, a nucleic acid, or the like. In certain aspects, the agent is a MORT small interfering RNA (siRNA). Based on the MORT RNA sequence disclosed herein, one of skill in the art can design an siRNA suitable to reduce MORT RNA levels using available siRNA design tools such as siDESIGN Center (GE Lifesciences), siRNA Wizard (Invivogen), siRNA Design Tools (The RNAi Web), etc. Reagents and protocols particularly designed for the transfection of siRNAs are readily available and include, e.g., DharmaFECT transfection reagent (GE Lifesciences), Mission siRNA transfection reagent (Sigma-Aldrich), X-tremeGene siRNA transfection reagent (Roche Life Sciences), etc.

In certain aspects, upon introduction of the agent into the cell having a mortal phenotype, the cell may be cultured for an amount of time sufficient for the agent to reduce MORT RNA levels therein to immortalize the cell. According to certain embodiments, the cell is present in a subject, and the introducing includes administering a pharmaceutical composition that includes the agent (e.g., an siRNA) to the subject such that the agent is taken up by the cell.

Accordingly, the methods for immortalizing a cell may be in vitro or in vivo and find use, e.g., when it is desirable to stimulate cell proliferation, e.g., for tissue regeneration purposes or the like.

EXAMPLES

Immortality is an essential characteristic of human carcinoma cells. We recently developed an efficient, reproducible method that immortalizes human mammary epithelial cells (HMEC) in the absence of gross genomic changes by targeting two critical senescence barriers. Consistent transcriptomic changes associated with immortality were identified using microarray analysis of isogenic normal finite pre-stasis, abnormal finite post-stasis, and immortal HMECs from four individuals. 277 genes consistently changed in cells that transitioned from post-stasis to immortal. Gene ontology analysis of affected genes revealed biological processes significantly altered in the immortalization process. These immortalization-associated changes showed striking similarity to the gene expression changes seen in The Cancer Genome Atlas (TCGA) clinical breast cancer data. The most dramatic change in gene expression seen during the immortalization step was the down-regulation of an unnamed, incompletely annotated transcript that we called MORT, for mortality, since its expression was closely associated with the mortal, finite lifespan phenotype. We show here that MORT (ZNF667-AS1) is expressed in all normal finite lifespan human cells examined to date and is lost in immortalized HMEC. MORT gene silencing at the mortal/immortal boundary was due to DNA hypermethylation of its CpG island promoter. This epigenetic silencing is also seen in human breast cancer cell lines and in a majority of human breast tumor tissues. The functional importance of DNA hypermethylation in MORT gene silencing is supported by the ability of 5-aza-2'-deoxycytidine to reactivate MORT expression. Analysis of TCGA data revealed deregulation of MORT expression due to DNA hypermethylation in 15 out of the 17 most common human cancers. The epigenetic silencing of MORT in a large majority of the common human cancers suggests a potential fundamental role in cellular immortalization during human carcinogenesis.

To identify consistent transcriptomic changes associated with immortality, we used microarray analysis to profile the transcriptomes of isogenic pre-stasis, post-stasis, and immortal HMEC. 277 genes consistently changed in cells that transitioned from post-stasis to immortal. Gene ontology analysis of affected genes revealed biological processes significantly targeted in the immortalization process, and when compared with The Cancer Genome Atlas (TCGA) breast cancer data, the gene changes observed in immortal HMEC showed striking similarity to the gene expression changes seen in clinical cancer. For example the eight genes that comprised the most significantly overrepresented gene ontology, the integrin-mediated signaling pathway, were all downregulated both during the HMEC immortalization step and in clinical human breast carcinomas. Other common gene ontologies affected during HMEC immortalization that are also seen in clinical breast cancer include biological processes associated with apoptosis and programmed cell death, cell adhesion and extracellular matrix organization, and stem cell division and protein tyrosine kinase activity.

The most dramatic change in gene expression seen during the immortalization step was the down-regulation of an unnamed, incompletely annotated transcript that we called MORT, for mortality, since its expression was closely associated with the mortal, finite lifespan phenotype. MORT is a primate-specific lncRNA of the lincRNA class, has a long cellular half-life, and is enriched in the cytoplasmic fraction. The number of lncRNAs annotated in human genome is approaching 60,000[3], and while their diverse mechanistic roles have remained enigmatic and incompletely resolved[4-7], they are increasingly appreciated as regulators of normal cell physiology[8,9]. lncRNAs that play fundamental roles in cell function include XIST in X chromosome inactivation[10-14], and HOTAIR in the control of the HOXD cluster[15]. Correspondingly, lncRNA dysregulation has been well-documented in various diseases including cancers[16-20].

Materials and Methods

Cell Culture.

Finite and immortalized HMEC were generated and grown as previously described[1,2,32]. In brief, finite lifespan HMEC from specimens 184 batch D, 240L batch B, 122L and 805P were obtained from reduction mammoplasty tissue or normal tissue peripheral to a tumor (805P) from women aged 21, 19, 66, and 91 years, respectively. The cells were grown in M87A medium supplemented with 0.5 ng/ml cholera toxin, and 0.1 nM oxytocin (Bachem). Retroviral transduction was performed as described[1,2]. Breast tumor lines MDA-MB231, MDA-MB453, and MCF7 were grown as previously described[33,34].

5-aza-2'-deoxycytidine Treatment

Cells were treated with 1 μM 5-aza-2'-deoxycytidine (Sigma) for 96 h, as previously described[33].

Nucleic Acid Isolation.

Genomic DNA was isolated using the DNeasy Blood and Tissue Kit according to the manufacturer's protocol (Qiagen). Total RNA was harvested using TRIzol and purified using the miRNeasy Kit (Qiagen). The quantity of each sample was assessed using absorbance at 260 nm on the NanoDrop 1000 Spectrophotometer.

Microarray analysis. RNA labeling and hybridization to Affymetrix GeneChip® Human Gene 1.0 ST Arrays, and the microarray scanning was performed according to the manufacturer's protocols. The data were analyzed in R programming environment[35]. The raw data from CEL files were normalized and summarized using package olige[36]. Differential expression was tested using the package limma[37]. All p-values were adjusted to control the false discovery rate according to Benjamini and Hochberg's. Enrichment of Gene Ontology terms in differentially expressed genes was tested using package GOstats[38].

The size of two standard deviations above the mean for random ORF was calculated using function y=91*ln(x)-330 as described[39].

DNA methylation analysis by MassARRAY. DNA methylation analysis by Sequenom MassARRAY (Sequenom) was performed as described[40]. Primer sequences are provided in FIG. 18 and are SEQ ID NOs: 3, 4, 5, and 6.

Figures 4A, 4B, 4D:
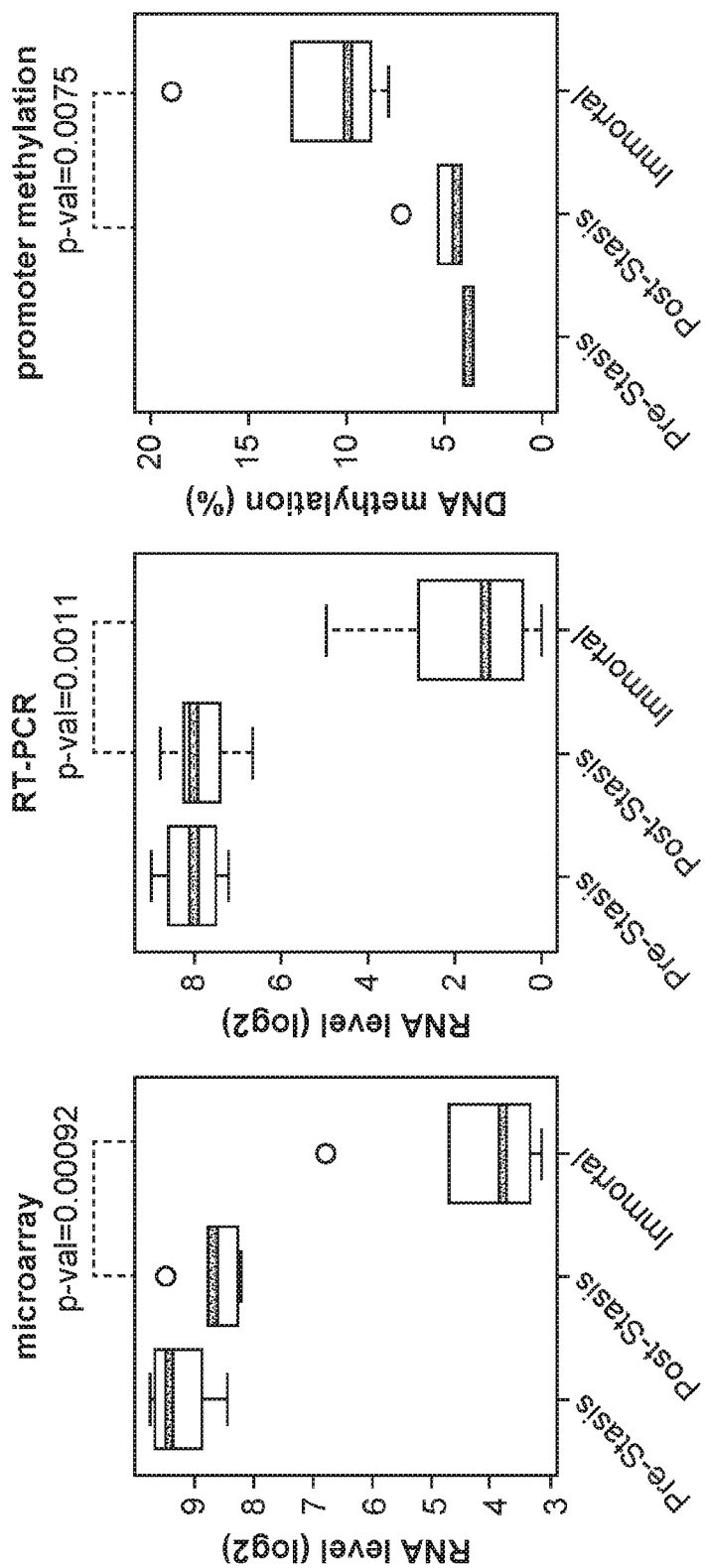
FIG. 4A is a plot showing MORT expression levels in individual cell type groups of the model, determined by Affymetrix microarray.
FIG. 4B is a plot showing MORT expression levels in individual cell type groups of the model, determined by RT-PCR.
FIG. 4D is a plot showing DNA methylation level of MORT promoter in individual cell type groups of the model. P-values indicated (paired t-test) are for contrast immortal vs. post-stasis.
Figure 4C:
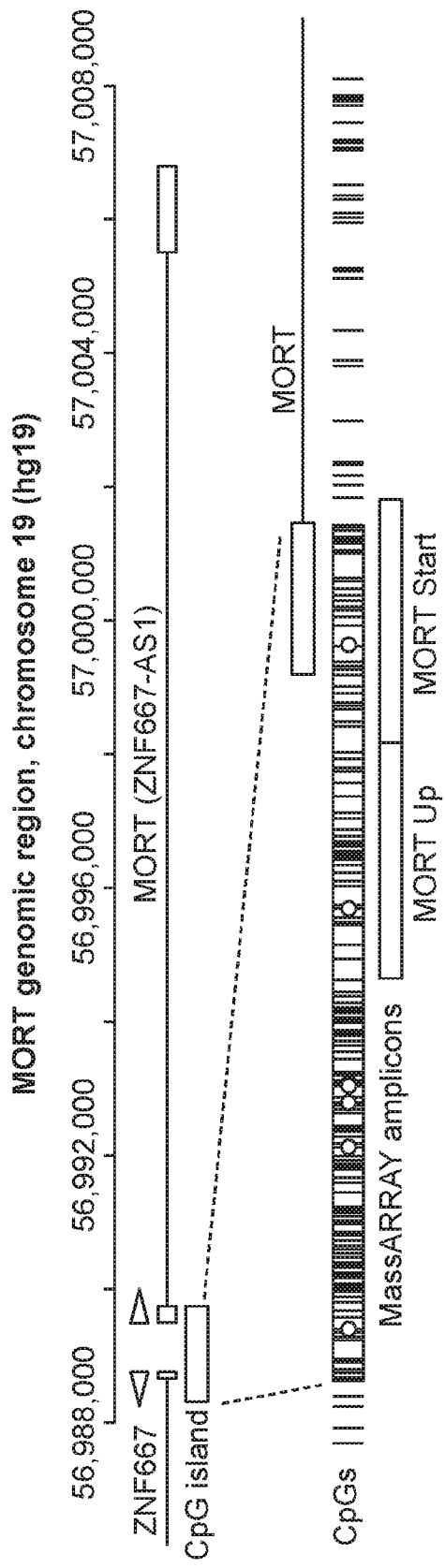
FIG. 4C is a graph of MORT genomic location. The promoter part is expanded in the lower panel. The individual CpG dinucleotides in the region are displayed as vertical black bars. The region analyzed for DNA methylation by MassARRAY is indicated by boxes. The CpGs covered by Illumina HumanMethylation450 array and used to analyze the TCGA data are indicated by circles.

Oligonucleotides used for MassARRAY analysis were ordered from Integrated DNA Technologies. Two MassARRAY amplicons covered 800 bp region including the first MORT exon and about 500 bp upstream MORT transcription start (FIG. 4C). The mean DNA methylation of all 26 informative CpG units within MassARRAY amplicons was used for data presentation and statistical analysis.

Real-Time RT-PCR.

The reverse transcription and real-time PCR was performed as previously described in Oshiro M M, Watts G S, Wozniak R J, Junk D J, Munoz-Rodriguez J L, Domann F E, Futscher B W. Mutant p53 and aberrant cytosine methylation cooperate to silence gene expression. Oncogene 2003; 22:3624-34 (reference 1 herein), and Vrba L, Junk D J, Novak P, Futscher B W. p53 induces distinct epigenetic states at its direct target promoters. BMC Genomics 2008; 9:486 (reference 41 herein), both incorporated herein by reference. Primers were designed for MORT, GAPDH, MYC and XIST and used with the Human Universal Probe Library Set (Roche Diagnostics). The cycle threshold (Ct) MORT values were normalized between the samples using GAPDH Ct values. The data were then converted into a value that is in log 2 scale, but increases with the expression level using formula 40-Ct. Since 40 was the total number of PCR cycles it was the lowest detectable expression level and therefore it was considered the background and set as 0 to display the data in the plots.

Online Data Analysis.

The Illumina Human Body Map 2.0 transcriptome RNA-Seq data were downloaded from SRA (ERP000546) and aligned to hg19 human reference using tophat[42]. The aligned RNA seq data for breast cancer cell lines were downloaded from Cancer Genomics Hub. MORT rpkm values were determined using samtools[43] and custom R scripts. RNASeqV2 and Illumina HumanMethylation450 DNA methylation data for tumor and normal tissue samples were downloaded from The Cancer Genome Atlas Data Portal. Mean RNA-Seq rpkm values for exons constituting the MORT RNA were plotted against the mean DNA methylation of the 7 CpGs from MORT promoter region for individual samples. The spearman correlation coefficient rho between RNA level and DNA methylation was calculated using function cor.test. For the GO categories comparison plots the raw TCGA RNA-Seq counts for individual exons were normalized using voom function[44] from the package limma and the differential expression between tumor and normal samples was calculated using the limma package.

Accession Numbers. The Gene Expression Omnibus (GEO) accession number for microarray dataset is GSE72353, hereby incorporated by reference.

SEQ ID NO:1 is the genomic sequence for the MORT long non-coding RNA and surrounding sequence. SEQ ID NO:2 is human lincRNA MORT as cloned using 2 overlapping PCR fragments corresponding to the exon 1 and the exon 2, that were joined in vitro, the template for PCR was genomic DNA of specimen 184.

Example 1: Using Immortalized Cells to Find Differentially Expressed Genes

We have described previously a two-step procedure of HMEC immortalization using pathologically relevant agents that does not cause gross genomic changes in Garbe J C, Vrba L, Sputova K, Fuchs L, Novak P, Brothman A R, Jackson M, Chin K, LaBarge M A, Watts G, et al. Immortalization of normal human mammary epithelial cells in two steps by direct targeting of senescence barriers does not require gross genomic alterations. Cell Cycle 2014; 13:3423-35 (reference 1 herein) and in U.S. Ser. No. 14/505,491, both of which are incorporated herein by reference in their entireties for all purposes. Herein we characterize gene expression changes occurring during this immortalization process using HMEC from four different individuals (women aged 19, 21, 66 and 91 years). FIG. 1 shows the analyzed samples and the steps taken to bypass the stasis and immortalization barriers. The first step is bypassing the stasis barrier by either targeting p16 using p16sh RNA or overexpression of a ccnd1/CDK2 fusion gene, thereby preventing RB-mediated stasis. These post-stasis cultures are then immortalized by transduction of c-MYC.

Figure 2B:
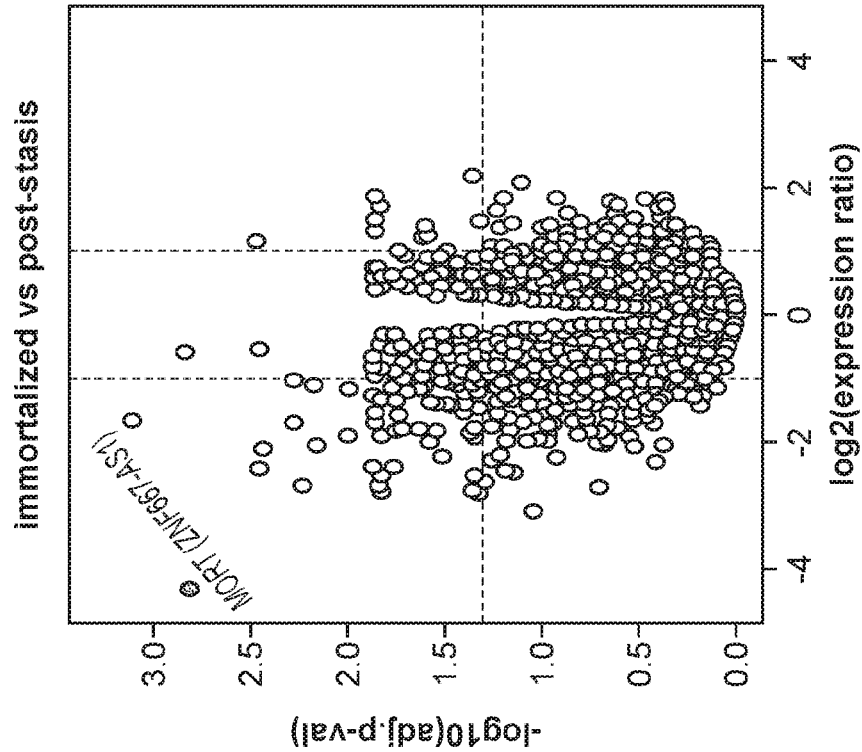
FIG. 2B is a volcano plot of gene expression changes associated with bypassing immortalization barriers. Vertical and dashed lines indicate two-fold changes in expression. The horizontal dashed line indicates 0.05 adjusted p-value cut-off. MORT gene (dot) with outstanding change in expression is labeled.
Figure 2A:
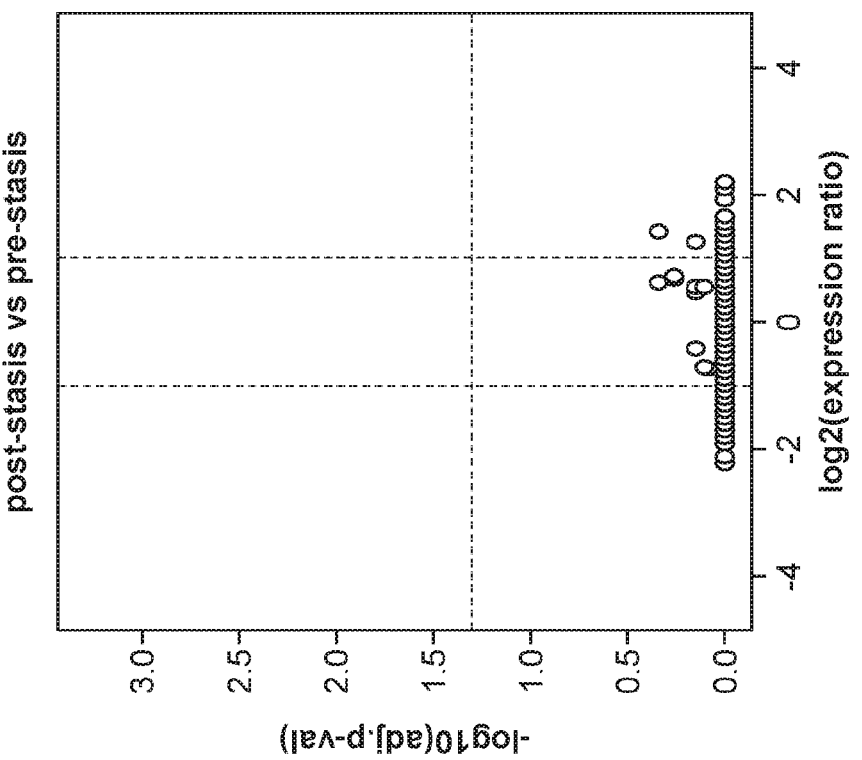
FIG. 2A is a volcano plot of gene expression changes associated with bypassing stasis barriers.

Gene expression was analyzed using Affymetrix Human Gene 1.0 ST microarrays in all three types of samples; finite pre-stasis strains, finite post-stasis strains with interrupted RB pathway, and c-MYC-immortalized lines. Although there were 116 genes with at least two fold mean expression change after the first genetic modification that led to bypassing stasis (FIG. 1, FIG. 15), none of the changes were consistent enough across the four individuals to be statistically significant (FIG. 2A). However, after the second genetic modification, which led to immortalization, there were significant changes in gene expression (FIG. 2B, FIG. 16). 277 genes were significantly changed after multiple testing p-value adjustment (adj.p-value <0.05), and 77 of these genes were changed at least two fold.

Figure 2C:
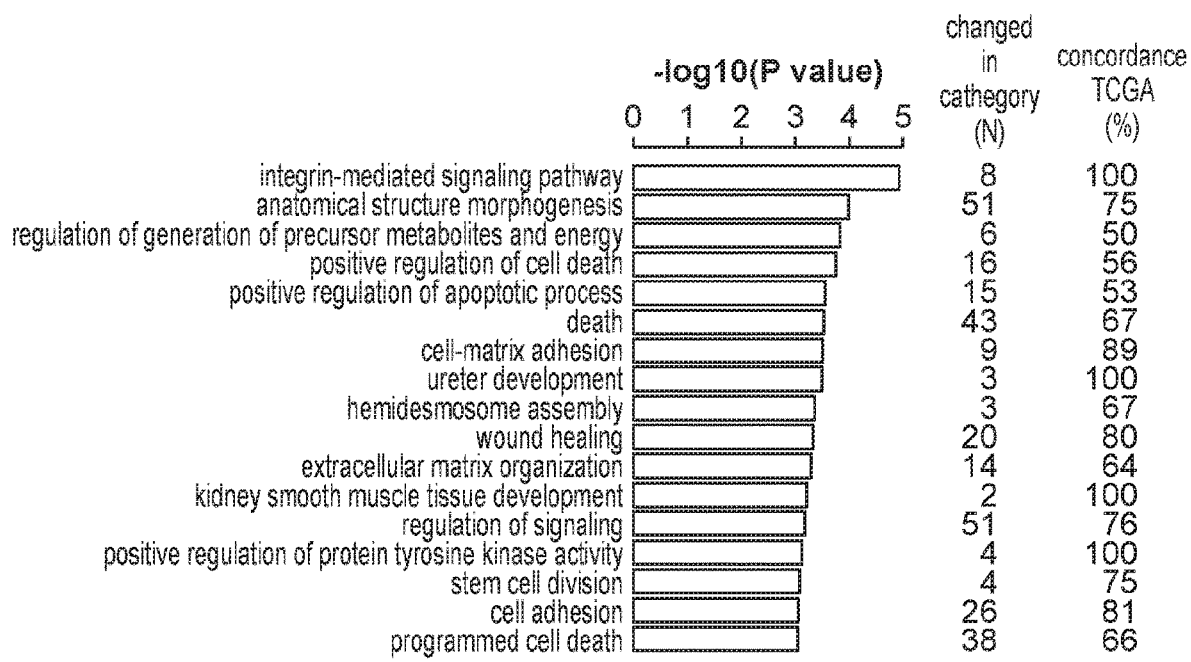
FIG. 2C is a graph showing the biological processes enriched among the genes changed during the immortalization step. The two columns on the right indicate, for each GO biological process, the number of genes that were changed in HMEC model and the proportion of these genes that are changed in TCGA cohort of 917 breast carcinomas in the same direction as in the immortalization step in the in vitro model.

To find relationships between gene expression and phenotypic changes, the 277 differentially expressed genes were tested for enrichment of Gene Ontology (GO) terms. The significantly overrepresented biological processes (FIG. 2C, FIG. 17) included: positive regulation of cell death, positive regulation of apoptotic process, death, stem cell division and integrin-mediated signaling pathway. The enrichment of these GO terms in the differentially expressed genes is consistent with the gene expression changes expected during the gain of immortality, since they include biological processes associated with continued cell proliferation, such as those associated with apoptosis and programmed cell death, cell adhesion and extracellular matrix organization.

Figure 2D:
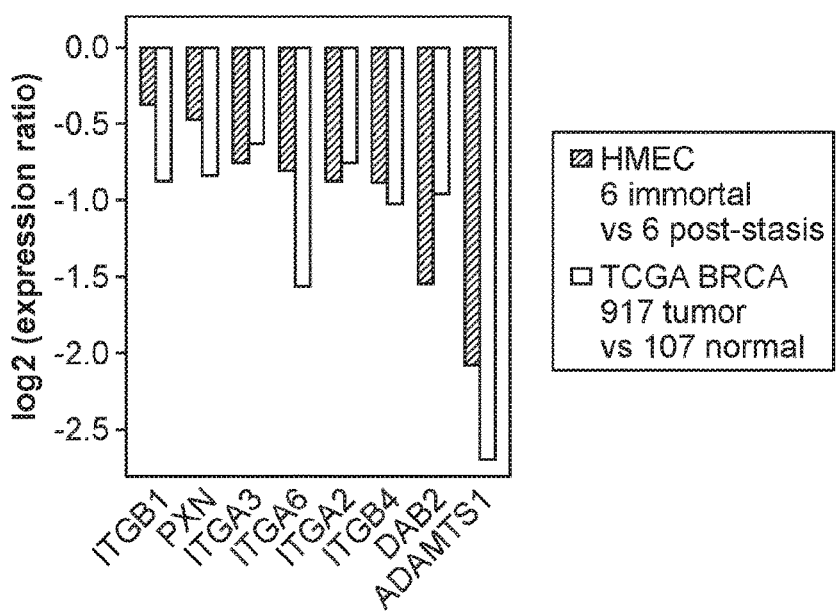
FIG. 2D is a plot showing the direction and the level of change in 8 members of integrin mediated signaling pathway changed during immortalization in the in vitro HMEC immortalization model. The plot shows the ratio the ratio of expression change in the in vitro model in comparison to that observed in clinical TCGA breast carcinoma data.
Figure 3A:
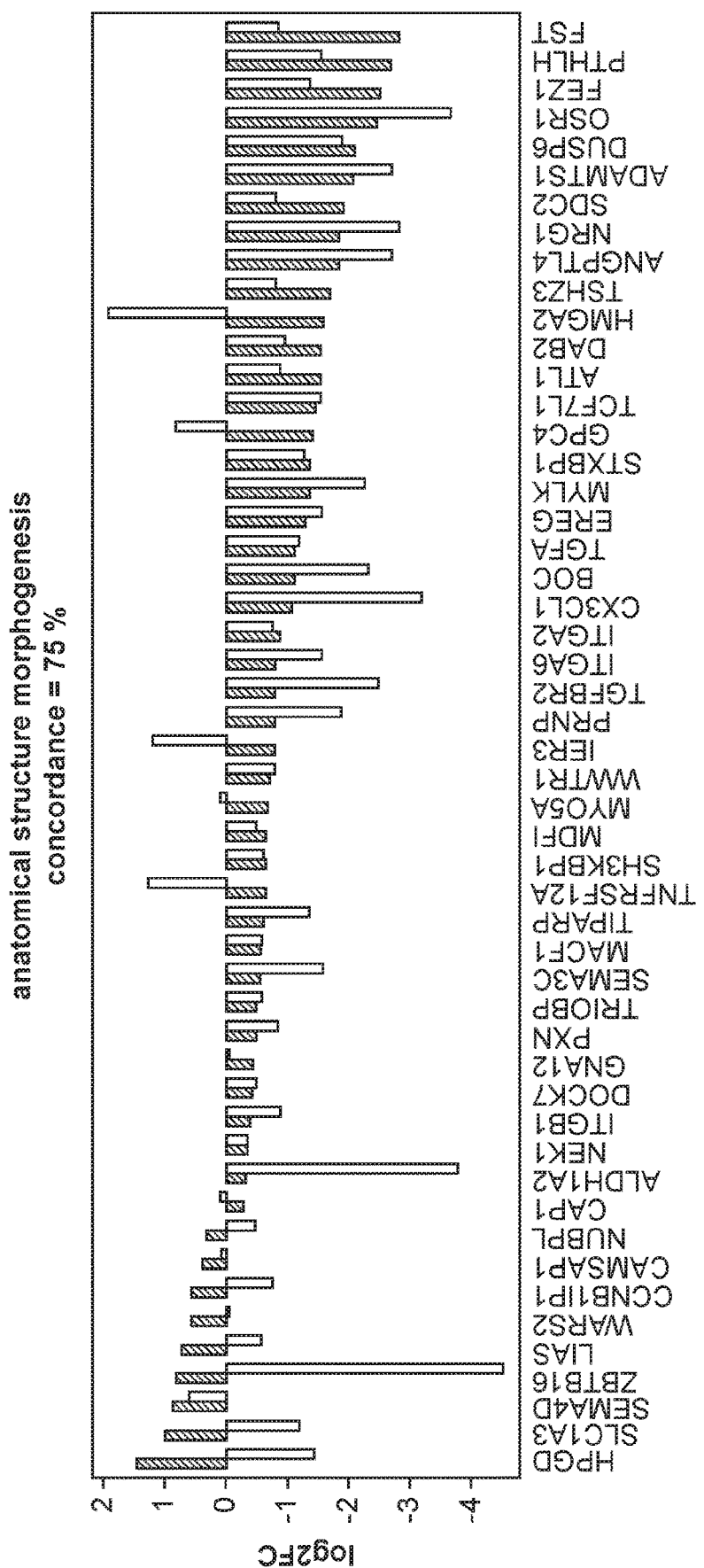
FIG. 3A, FIG. 3B, and FIG. 3C are graphs showing the comparison of gene expression changes in individual enriched GO categories in the in vitro immortalization model with those in the TCGA breast invasive carcinoma samples relative to non-tumor samples.
Figure 3B:
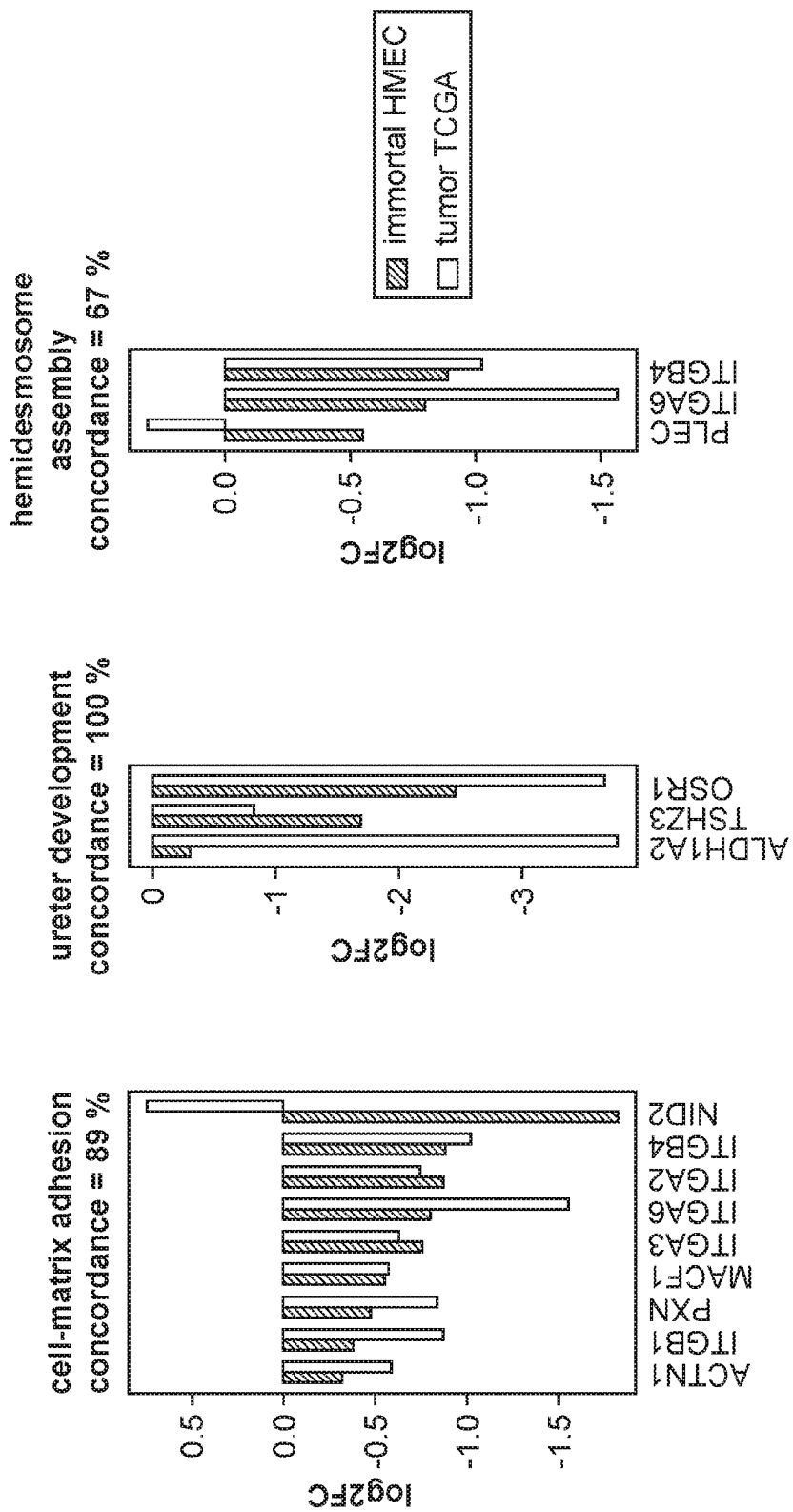
Figure 3C:
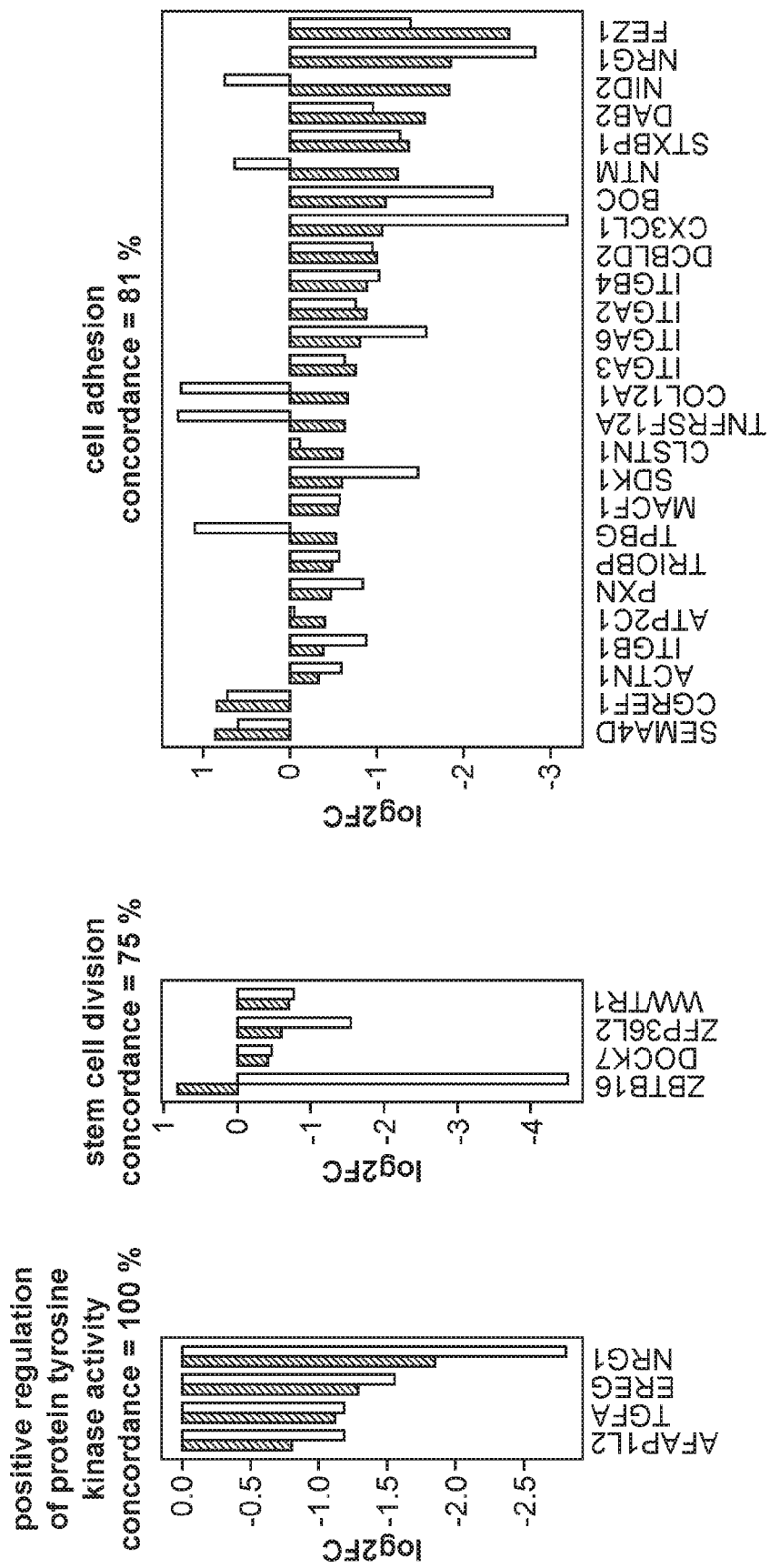
Figure 3C:
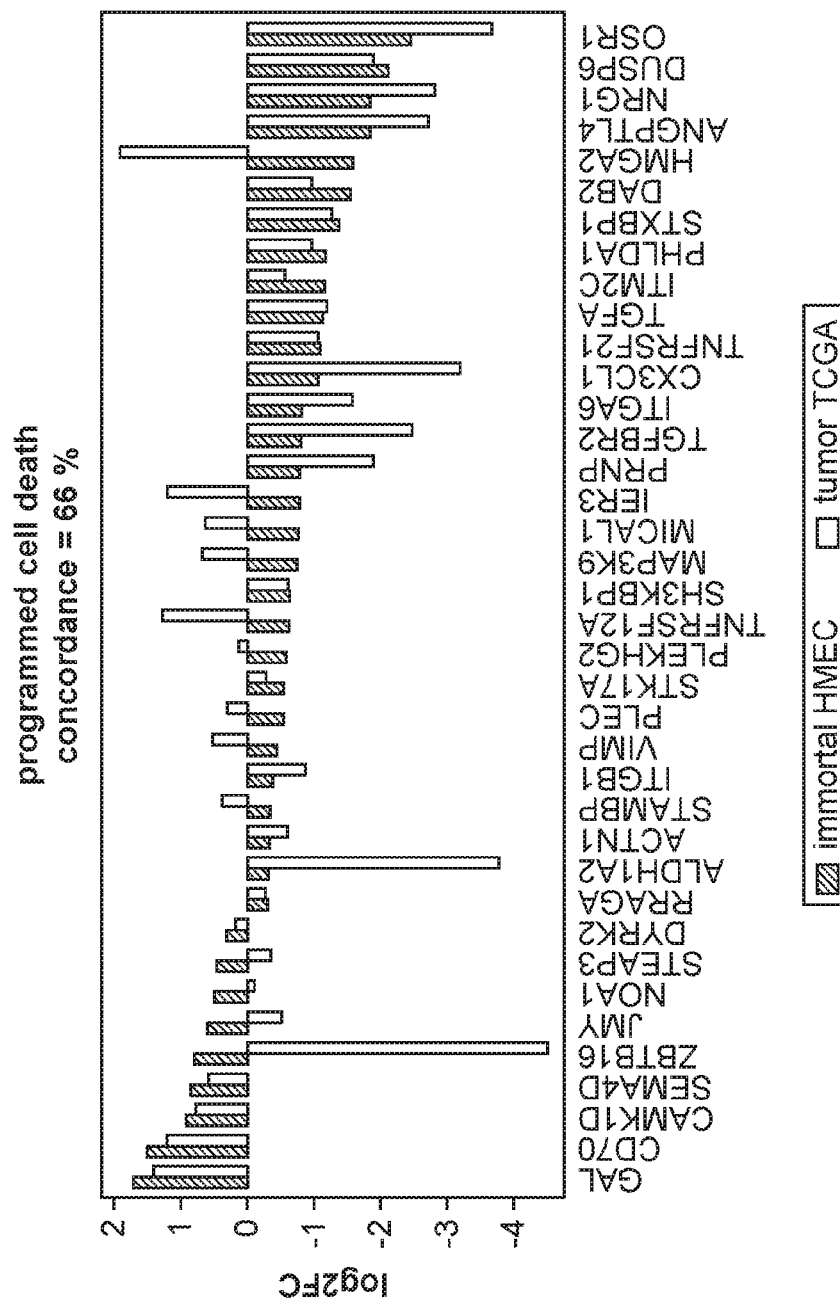

The integrin-mediated signaling pathway, the most overrepresented GO term, is involved in multiple processes including cell adhesion, migration, polarity, growth and death, and perturbed integrin function has long been linked to breast cancer[21-23]. Eight members of the integrin-mediated signaling pathway were significantly down-regulated. We determined if similar changes also occur during in vivo carcinogenesis by comparing the data from the in vitro HMEC immortalization step and TCGA data from clinical breast tumor samples (FIG. 2D). All 8 genes are also down-regulated to a similar extent in clinical breast tumor tissues compared to non-tumor tissues, indicating 100% concordance between the in vitro model and clinical cancer. The data comparing the in vitro model with TCGA data for the other 16 significantly overrepresented biological processes are shown in FIGS. 3A-C. Overall there is good concordance between the in vitro model of non-malignant immortalized HMEC and the TCGA data of breast carcinomas for most of the categories (FIG. 2C), particularly considering that the in vitro model identifies only gene expression changes during immortalization while the clinical tumor samples will have additional changes linked to malignancy. Overall, these findings indicate that the gene expression changes observed in our in vitro immortalization model are relevant for in vivo carcinogenesis and likely occur early during transformation.

Figure 5:
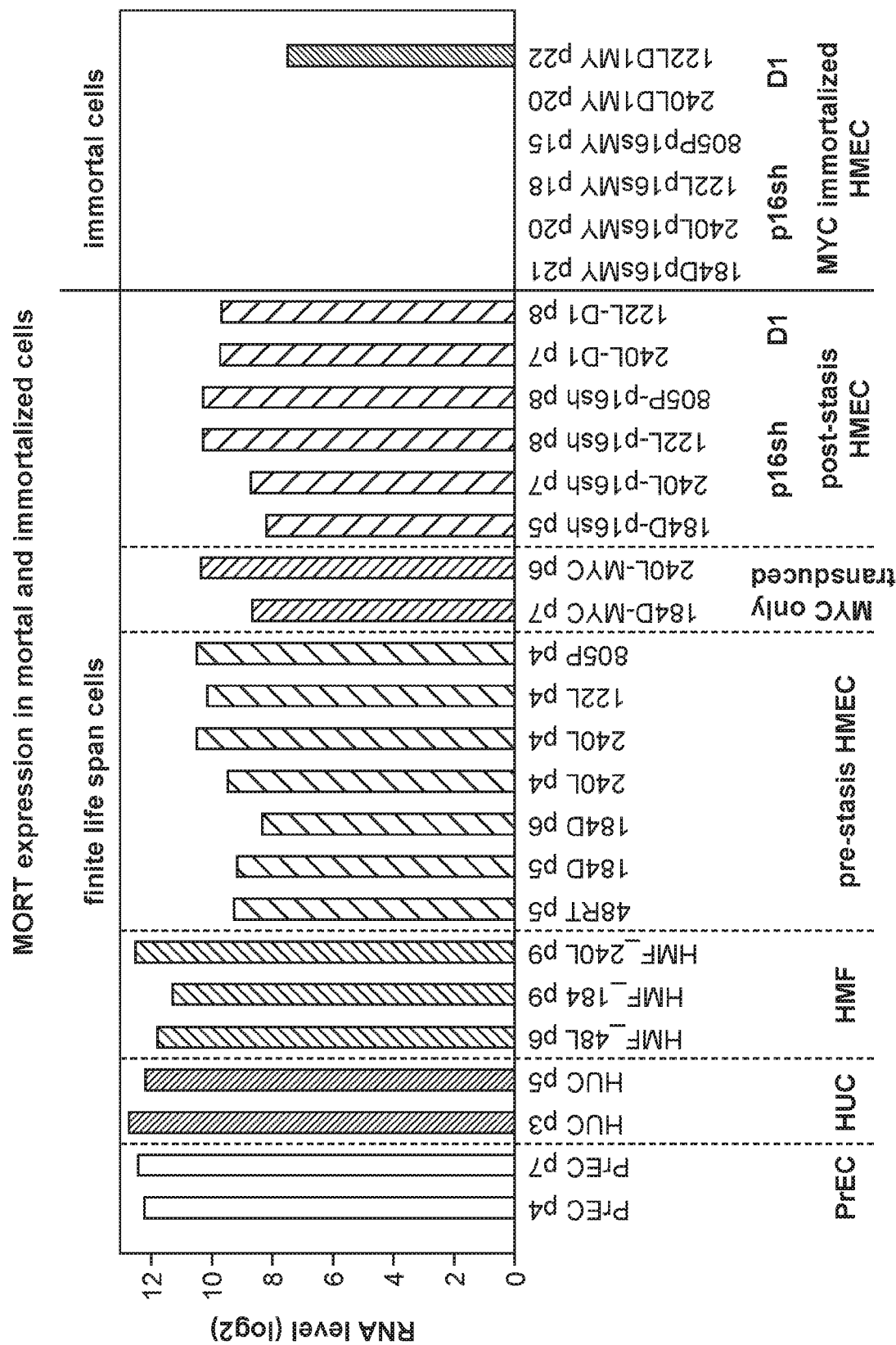
FIG. 5 is a graph of MORT expression in HMEC immortalization model cultures, additional primary cell types, and additional controls. Primary cell types prostate epithelial cells (PrEC), human urothelial cells (HUC), human mammary fibroblasts (HMF), human mammary epithelial cells (HMEC), c-MYC only transduced, and post-stasis HMEC express MORT. c-MYC alone likely has a little to no effect on MORT expression. c-MYC immortalized p16 or D1 cells have MORT either completely silenced or substantially reduced (122LD1MY).
Figure 6:
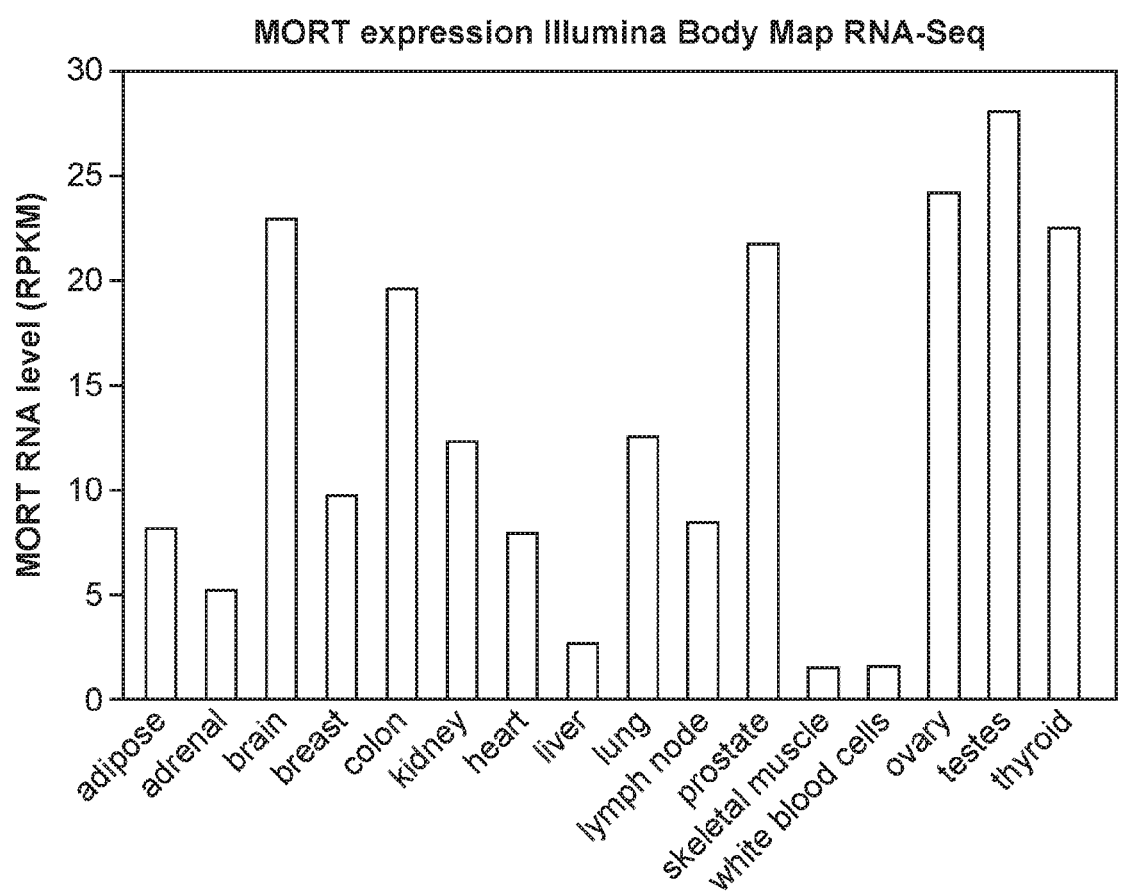
FIG. 6 is a graph of MORT expression across 16 tissues of Illumina Body Map.

Apart from the significant gene expression changes in the whole GO pathways, we identified one gene outside of GO pathways with an outstanding difference in expression between mortal vs immortal cells. This gene, that initially had only a numeric designation LOC100128252 and no GO annotation, is completely silenced during HMEC immortalization (FIG. 2B). We named it MORT since its expression seems to be a hallmark of mortal cells. MORT was found to be a non-coding RNA and it is named ZNF667-AS1 in the current RefSeq release. To validate the microarray data we performed real-time PCR analysis of the MORT transcript level; the microarray (FIG. 4A) and RT-PCR (FIG. 4B) data are in good concordance. We also analyzed MORT expression in three additional primary cell types; human mammary fibroblasts, prostate epithelial cells and human urothelial cells as well as in pre-stasis HMEC transduced by c-MYC alone. MORT is expressed in all the primary cell samples and c-MYC transduction alone does not cause its silencing (FIG. 5). We further expanded our analysis to 16 normal human tissues of Illumina body map data. MORT is expressed, at variable levels, in all 16 normal human tissues tested (FIG. 6). Overall, our gene expression analysis revealed a non-coding RNA transcript that is expressed in all normal cell types examined and is the most consistently and dramatically down-regulated transcript during the process of HMEC in vitro immortalization.

Figure 7:
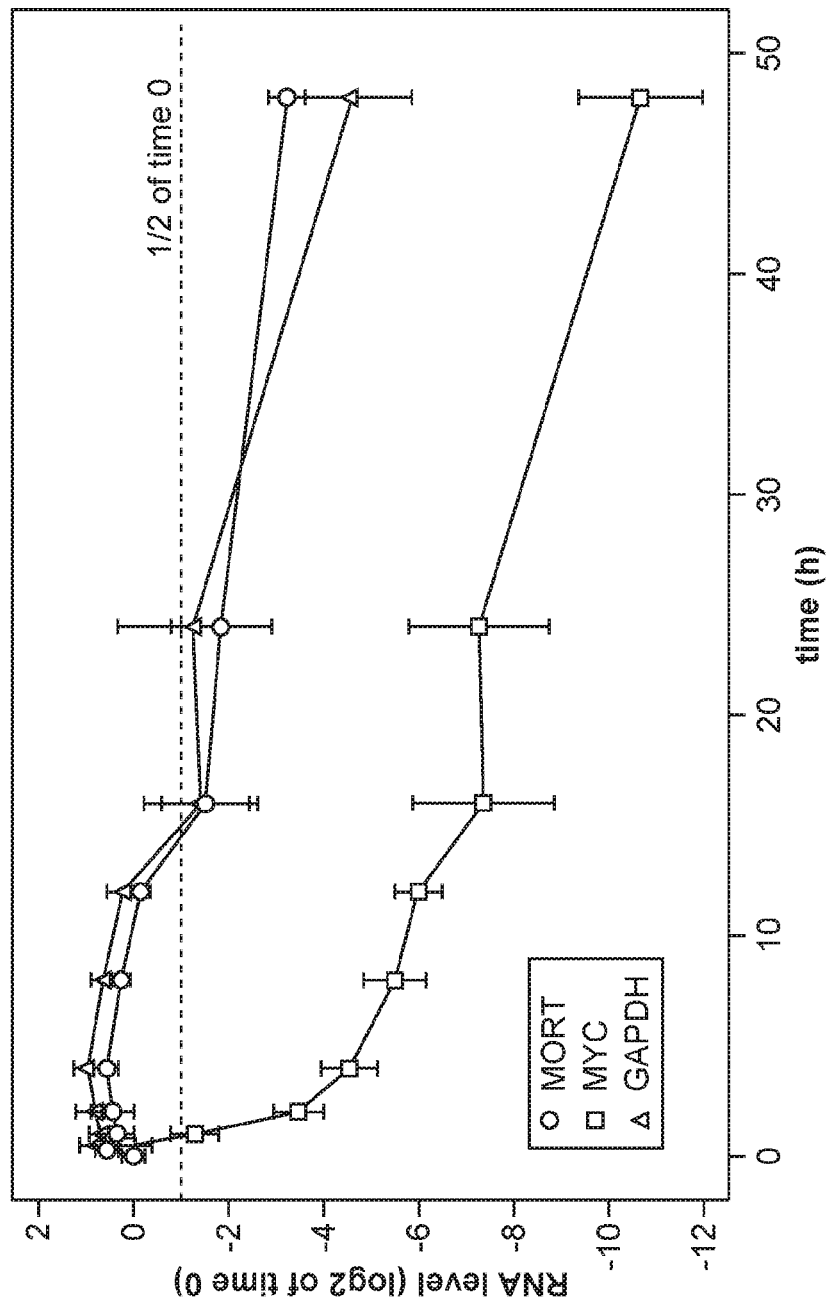
FIG. 7 is a graph showing determination of MORT transcript half-life using actinomycin D (1 µg/ml) treatment. c-MYC was used as a short half-life reference gene and GAPDH was used as a long half-life reference gene. (Yang et al. 2003). The results indicate that MORT has a long half-life of ~15 hours comparable to GAPDH. The error bars show the SEM of 3 independent experiments.
Figure 8:
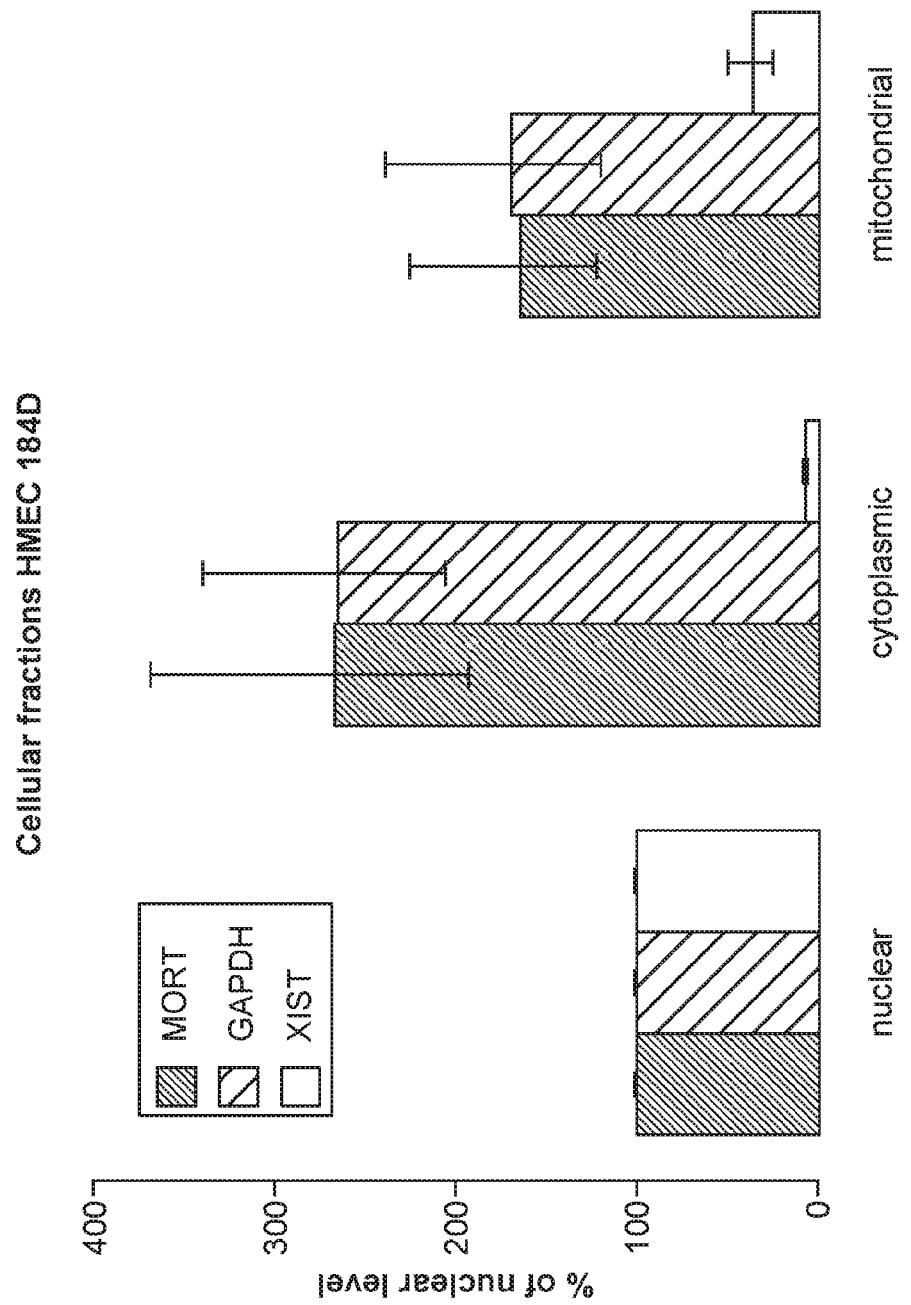
FIG. 8 is a graph of cellular localization of MORT. HMEC cells were lysed in hypotonic conditions using Dounce homogenizer and the lysate was separated by differential centrifugation to nuclear, mitochondrial, and cytoplasmic fractions. Relative representation of MORT, GAPDH (cytoplasmic), and XIST (nuclear) transcripts was determined by real-time PCR. All data are displayed relative to the nuclear fraction, which is set to 100%. The error bars show the SEM of 3 independent experiments. MORT is localized predominantly in the cytoplasmic fraction, similar to GAPDH.

The MORT gene is located on chromosome 19, within the zinc finger gene cluster 19.13. Its 1.53 kb RNA consists of 2 exons of 260 and 1270 bp separated by 16 kbp intron (FIG. 4C). The MORT promoter overlaps a large CpG island (1.4 kbp, 148 CpGs) that is shared with ZNF667 (head to head). The ZNF667 expression is also downregulated during immortalization although much less dramatically than MORT (FIG. 16), possibly due to its very low basal expression level that is about an order of magnitude lower than that of MORT. 12 kb downstream of the MORT terminator there is a promoter of ZNF471. Since the MORT transcript is polyadenylated, it is a product of RNA polymerase II. Although located within a ZNF gene cluster, MORT gene does not share a homology with ZNF genes. The second exon of MORT contains two LINE (L2 and L1MB3) and one LTR (LTR47B) repetitive elements. Based on random chance the transcript of MORT size (1.5 kb) could encode a 110 aa peptide (Dinger 2008). The MORT transcript contains five ORFs larger than 50 codons, however, none of them exceeds 70 codons. BlastX search have not found any putative conserved protein domains in these ORFs. According to Coding-Potential Assessment Tool (CPAT)[24], MORT has a negative hexamer score (−0.29) and a very low coding probability of 0.005 resulting in absence of coding label based on CPAT. Actinomycin D experiments revealed that the MORT transcript has a long half-life, comparable to the housekeeping gene GAPDH (FIG. 7). Cell fractionation experiments show enrichment of MORT in the extra-nuclear fraction suggesting a cytoplasmic function (FIG. 8). Overall, these observations indicate that MORT is unlikely to be a protein coding RNA and likely acts as a lincRNA at a steady transcript level outside the nucleus.

Next we searched for MORT orthologs in other species. Higher primates (chimpanzee, gorilla and orangutan) have regions with high homology to human MORT in a homologous genomic locus, and publicly available RNA-seq data from these species indicate that it is expressed. Old world monkeys (baboon, rhesus) have a region homologous to the first exon of human MORT in the homologous genomic location, however, they do not have a region with homology to the second MORT exon at this genomic locus. Therefore MORT seems to be an evolutionarily young lincRNA that has evolved during late primate evolution and is limited to higher primates. The emergence of a lincRNA that might have tumor suppressive activity during higher primate evolution is consistent with the long life span of higher primates and with the fact that a large fraction of non-coding RNAs found in humans are primate specific[25].

Since the silencing of gene expression is frequently accompanied by DNA methylation of its promoter region, we analyzed the DNA methylation status of the MORT promoter in mortal versus immortal HMEC. The data show a consistent increase in DNA methylation of the MORT promoter in immortalized cells across the four individual specimens (FIG. 4D). Therefore, the lincRNA MORT seems to belong to genes that are silenced by DNA methylation of their promoters.

Figure 9:
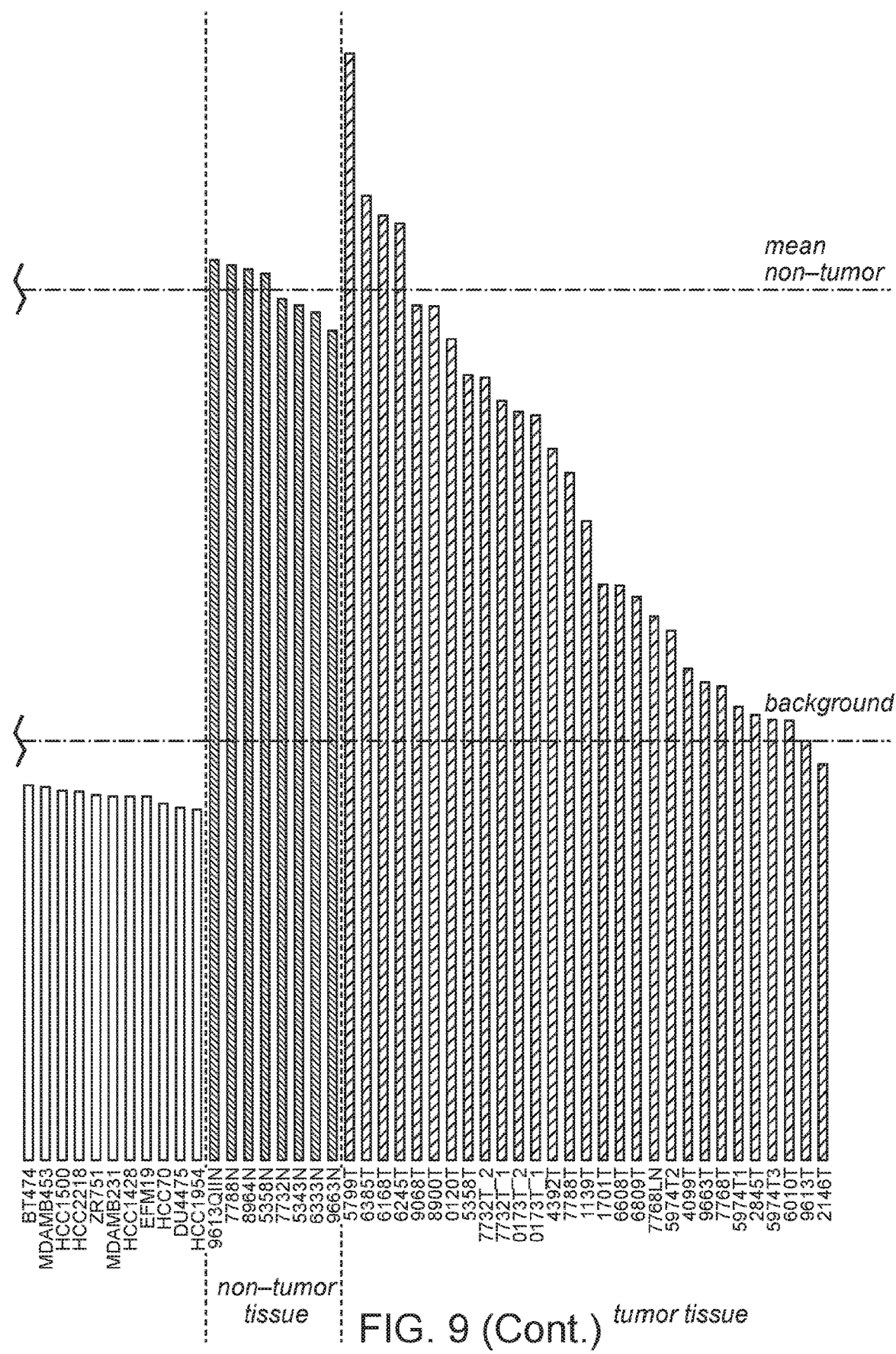
FIG. 9 is a graph of MORT expression level across breast cancer cell lines from cancer cell line encyclopedia (CCLE) and a set of 8 breast non-tumor samples and 27 breast carcinomas.
Figure 10:
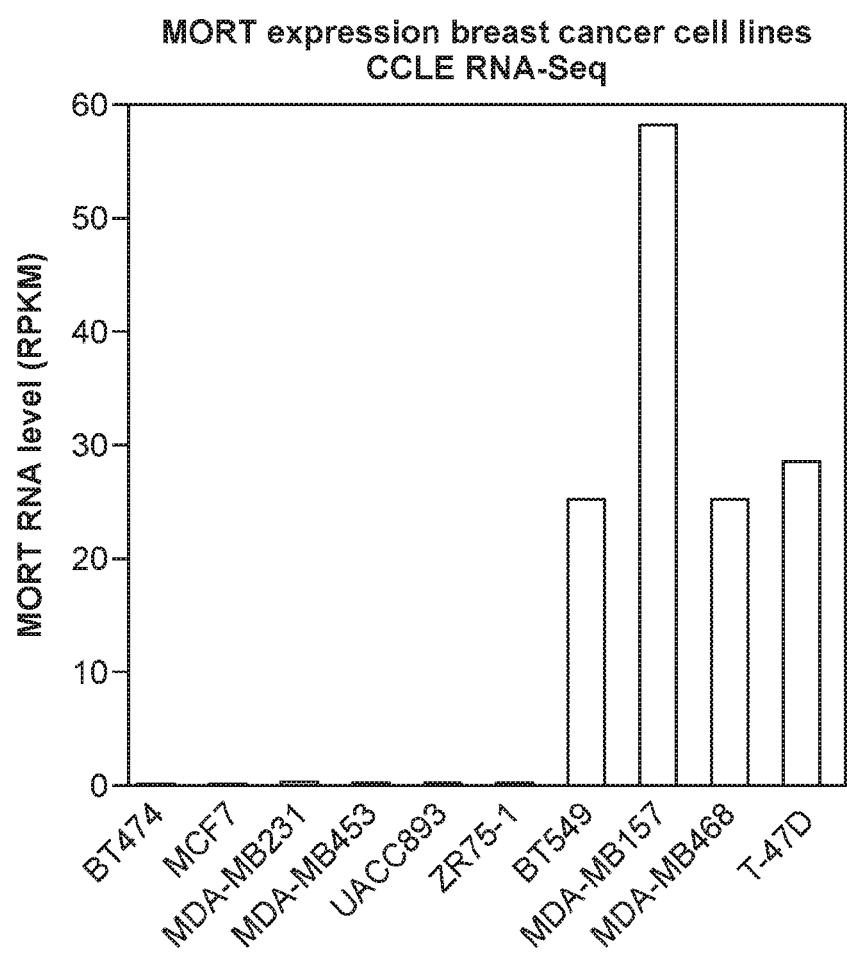
FIG. 10 is a graph of MORT expression level across 10 breast cancer cell lines from cancer cell line encyclopedia (CCLE) as determined by RNA-seq.

To find out whether MORT silencing is a more general process linked to human carcinogenesis, we first analyzed our earlier microarray expression data set from multiple breast tumors and non-tumor tissues (FIGS. 9 and 11A). The microarray data show deregulation of MORT transcript level across the tumor samples with a decrease in expression being the predominant trend. Similar results were found within a panel of breast tumor cell lines from the cancer cell line encyclopedia (CCLE)[26]—about one half of the tumor cell lines do not express any MORT and the level in the other half is deregulated compared to non-tumor breast tissue (FIGS. 9 and 10). These data suggest that MORT silencing is a common event in human breast carcinogenesis.

Figure 11D:
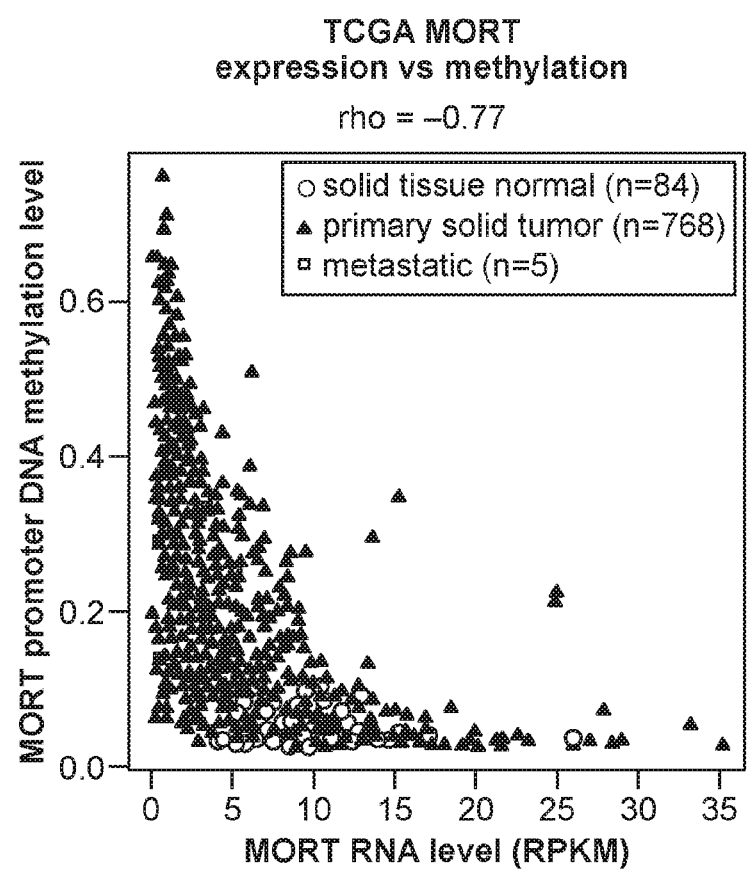
FIG. 11D is a plot showing the integration of DNA methylation and expression data of the TCGA cohort.
Figure 12A:
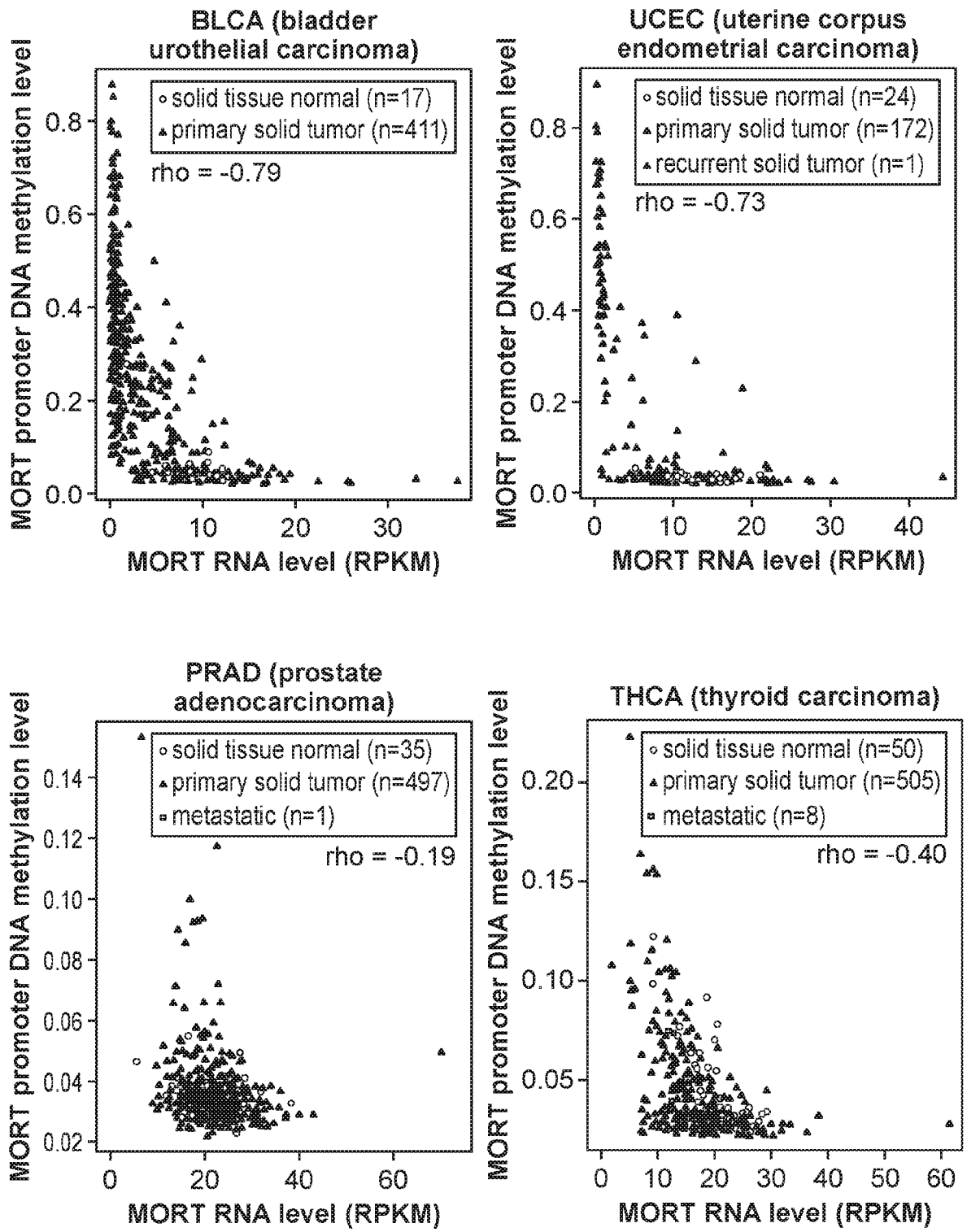
FIGS. 12A, 12B, 12C and 12D are graphs showing the integration of MORT expression and DNA methylation TCGA data for 16 additional TCGA tumor types. The x-axis shows MORT expression level according to RNA-seq and y-axis shows the level of MORT promoter methylation according to Illumina HumanMethylation450 microarray. The correlation coefficient rho between MORT expression and promoter methylation for each tumor type is displayed.
Figure 12B:
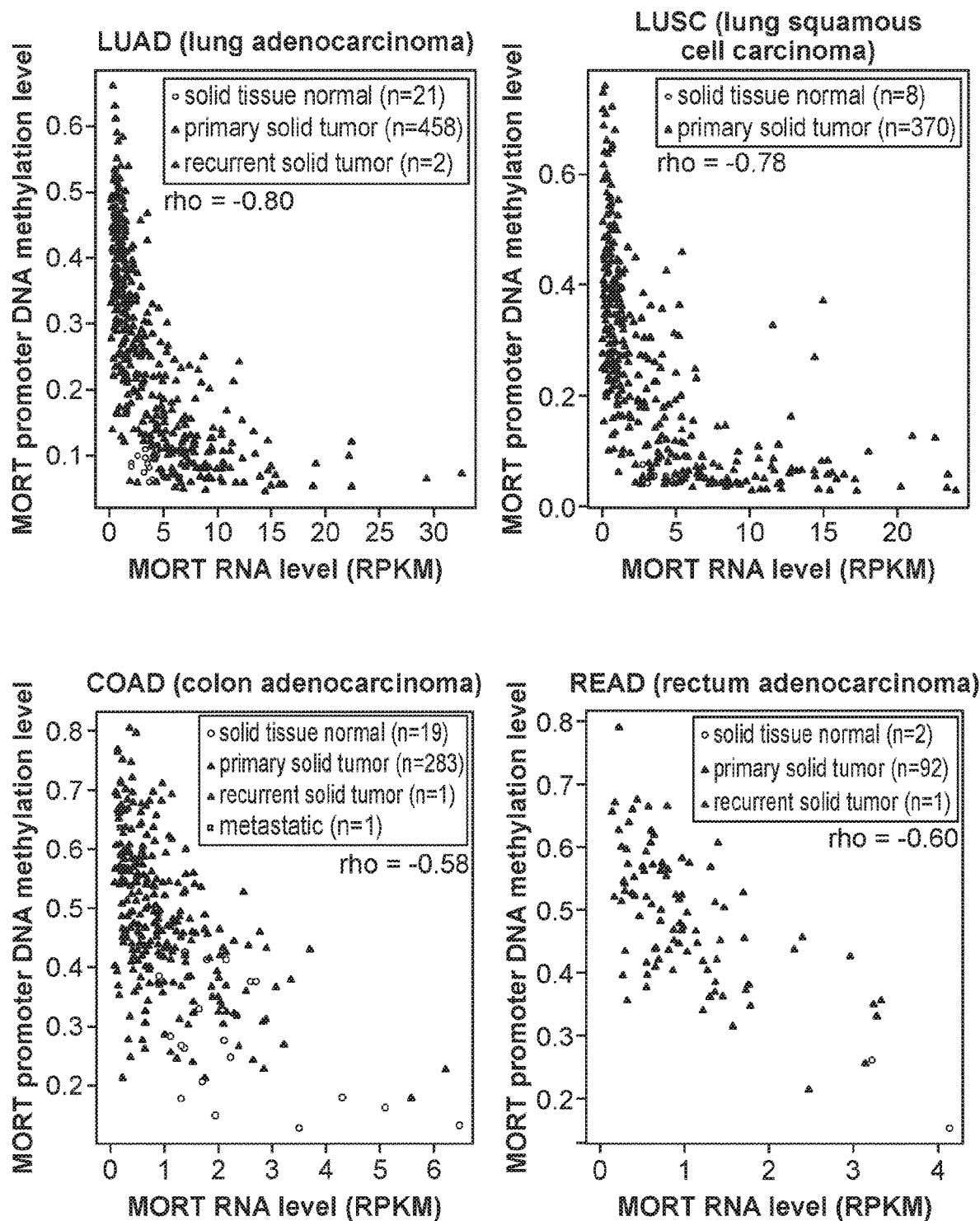
Figure 12C:
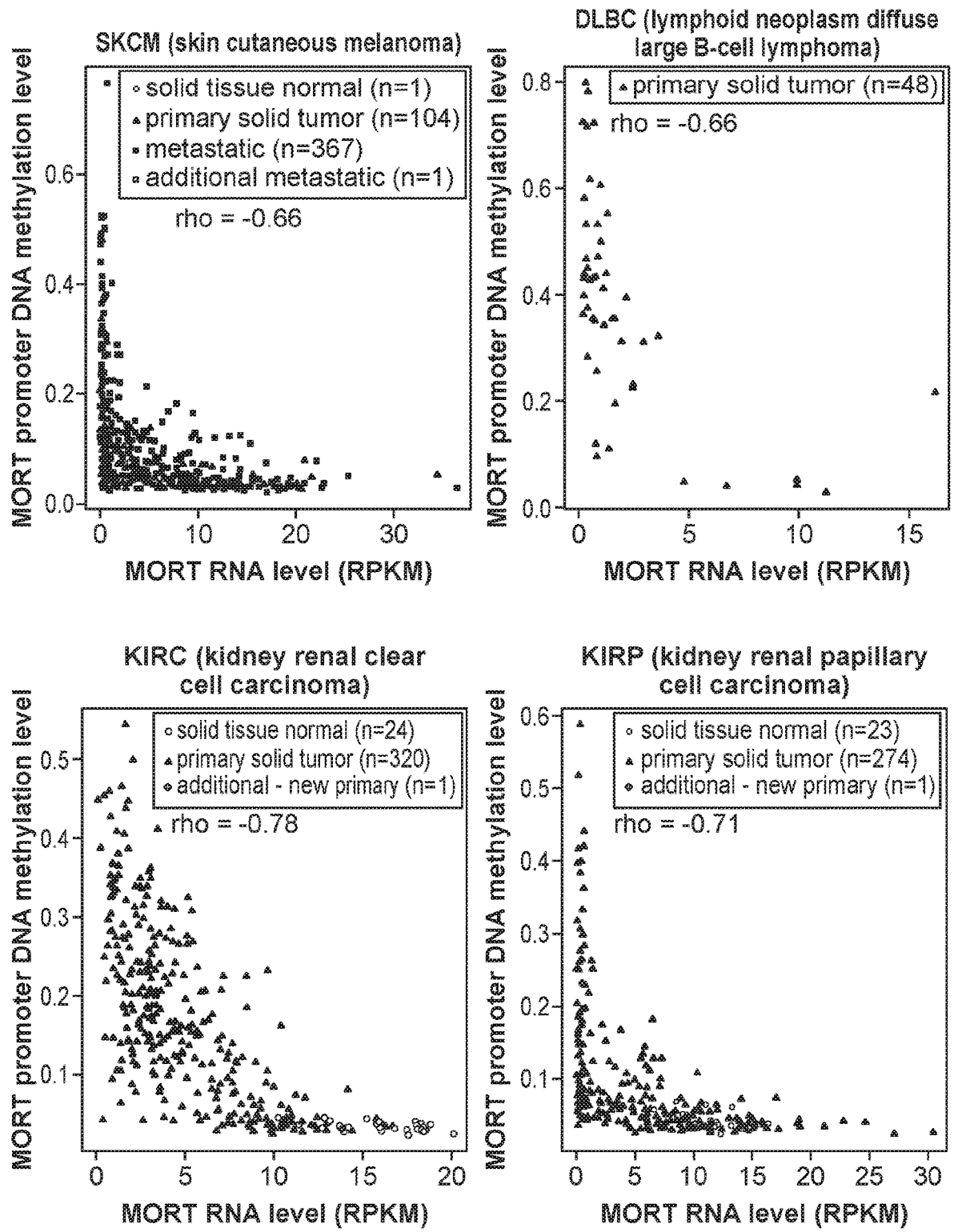
Figure 12D:
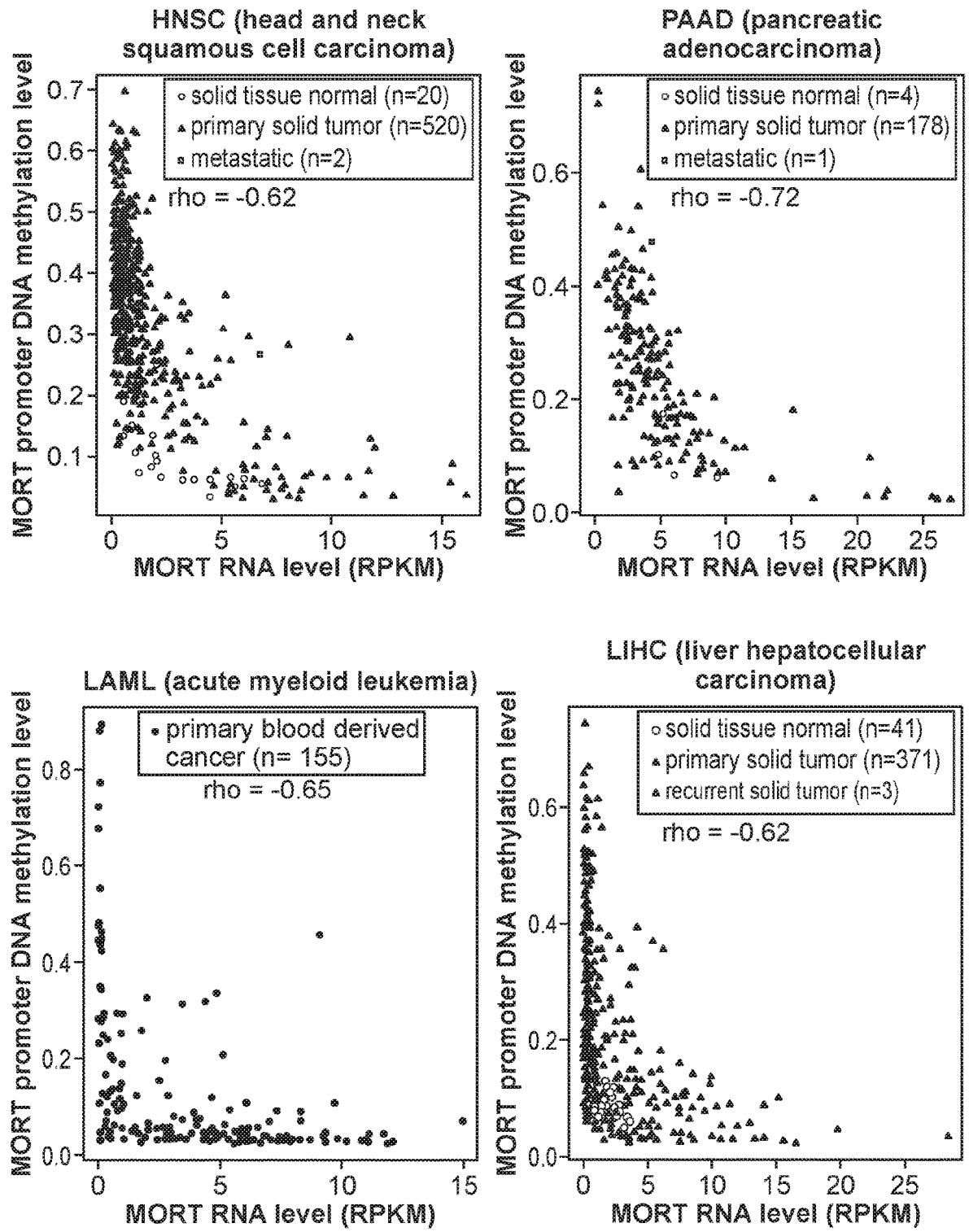

We used TCGA data to further empower our analysis of MORT in breast cancer. RNA-seq data of the MORT transcript and Illumina HumanMethylation450 DNA methylation data that covers several CpGs within MORT promoter region were integrated for over 800 clinical breast tumor or non-tumor tissue samples. The integrated transcriptome and DNA methylation data show a highly significant decrease in the level of MORT expression in tumors relative to non-tumor breast tissue (FIG. 11B) that is linked to a significant DNA hypermethylation of the MORT promoter (FIG. 11C). The strong negative correlation (rho=−0.77) between DNA methylation and the expression of this lncRNA (FIG. 11D) strongly suggests that MORT is epigenetically silenced in most breast cancers.

To expand the analysis of MORT's role in human carcinogenesis beyond breast cancer, we analyzed TCGA data from 16 additional tumor types that represent the top ten most frequent cancers found in males and females according to Cancer Facts and Figures. 2015[27]. MORT is deregulated in 14 out of the 16 tumor types analyzed (Table 1; FIGS. 12A-D). Table 1 shows the TCGA cancer type and disease abbreviation and correlation coefficient rho between DNA methylation of MORT promoter and MORT RNA level in individual TCGA samples for particular cancer type.

TABLE 2

Correlation between MORT RNA level and MORT promoter methylation for the 17 most common cancer types.

| Cancer Type | rho |
|---|---|
| Acute Myeloid Leukemia [LAML] | −0.65 |
| Bladder Urothelial Carcinoma [BLCA] | −0.79 |
| Breast invasive carcinoma [BRCA] | −0.77 |
| Colon adenocarcinoma [COAD] | −0.58 |
| Head and Neck squamous cell carcinoma [HNSC] | −0.62 |
| Kidney renal clear cell carcinoma [KIRC] | −0.78 |
| Kidney renal papillary cell carcinoma [KIRP] | −0.71 |

TABLE 2-continued

Correlation between MORT RNA level and MORT promoter methylation for the 17 most common cancer types.

| Cancer Type | rho |
| --- | --- |
| Liver hepatocellular carcinoma [LIHC] | −0.62 |
| Lung adenocarcinoma [LUAD] | −0.80 |
| Lung squamous cell carcinoma [LUSC] | −0.78 |
| Lymphoid Neoplasm Diffuse Large B-cell Lymphoma [DLBC] | −0.66 |
| Pancreatic adenocarcinoma [PAAD] | −0.72 |
| Prostate adenocarcinoma [PRAD] | −0.19 |
| Rectum adenocarcinoma [READ] | −0.60 |
| Skin Cutaneous Melanoma [SKCM] | −0.66 |
| Thyroid carcinoma [THCA] | −0.40 |
| Uterine Corpus Endometrial Carcinoma [UCEC] | −0.73 |

The majority of the tumor samples have MORT silenced in association with hypermethylation of its CpG island promoter. There is overall strong negative correlation (rho=−0.6 to −0.8, Table 2) between MORT promoter methylation and the MORT transcript level for these 14 tumor types. The two exceptions where MORT transcript level is not decreased and its promoter stays unmethylated are prostate adenocarcinomas and thyroid carcinomas. Overall, these analyses suggest that MORT is generally silenced by DNA methylation in a majority of human cancer types.

Figure 13:
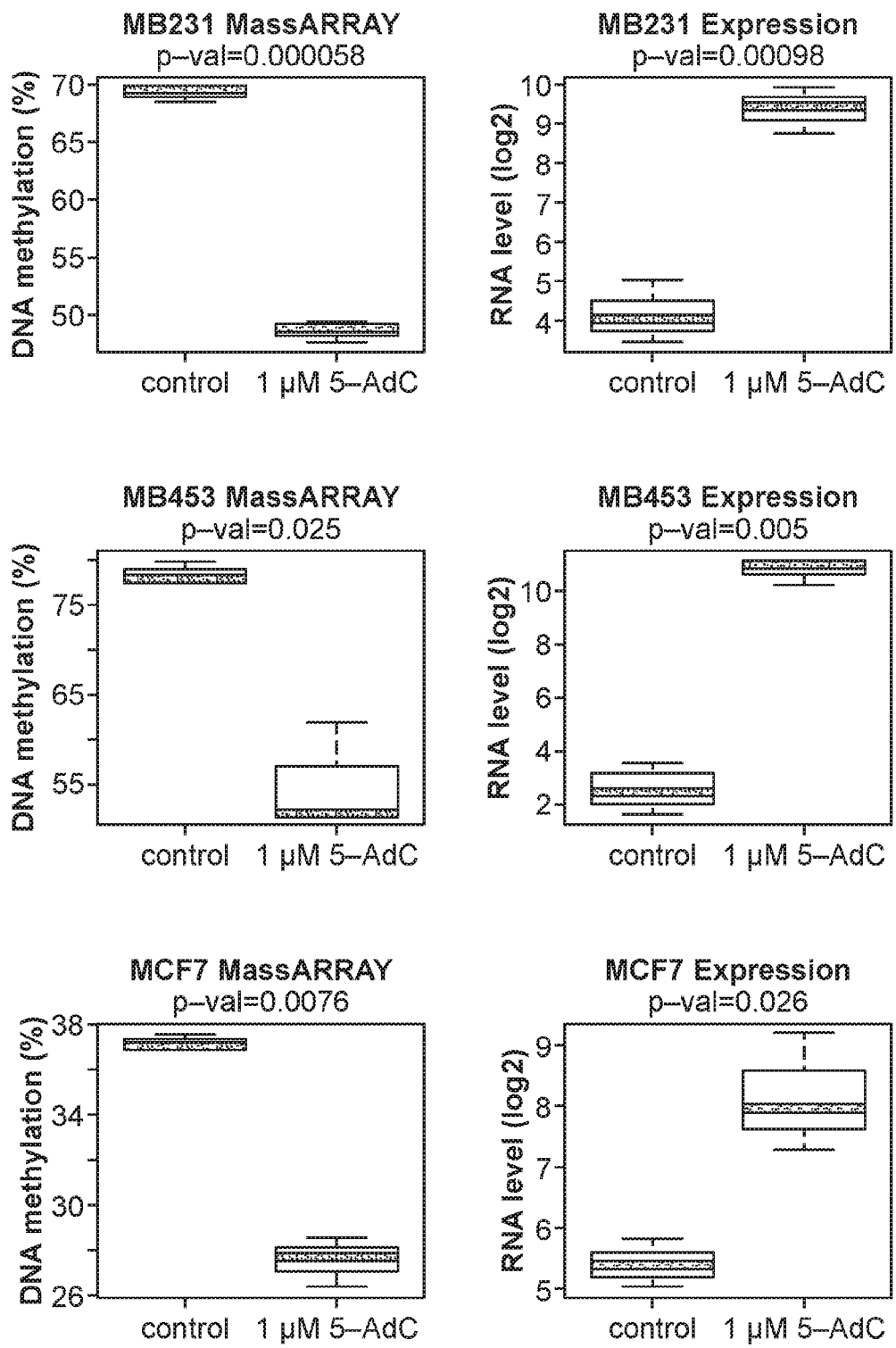
FIG. 13 consists of graphs showing MORT is reactivated by 5-AdC treatment in three MORT negative breast carcinoma tumor cell lines. MDA-MB231, MDA-MB453, and MCF7 cells were grown for 96 h in the presence or absence of 1 µM 5-AdC. The experiment was repeated three times. DNA methylation of MORT promoter was determined by Sequenom MassARRAY and MORT transcript level by real-time PCR. P-values are from paired t-test
Figure 14:
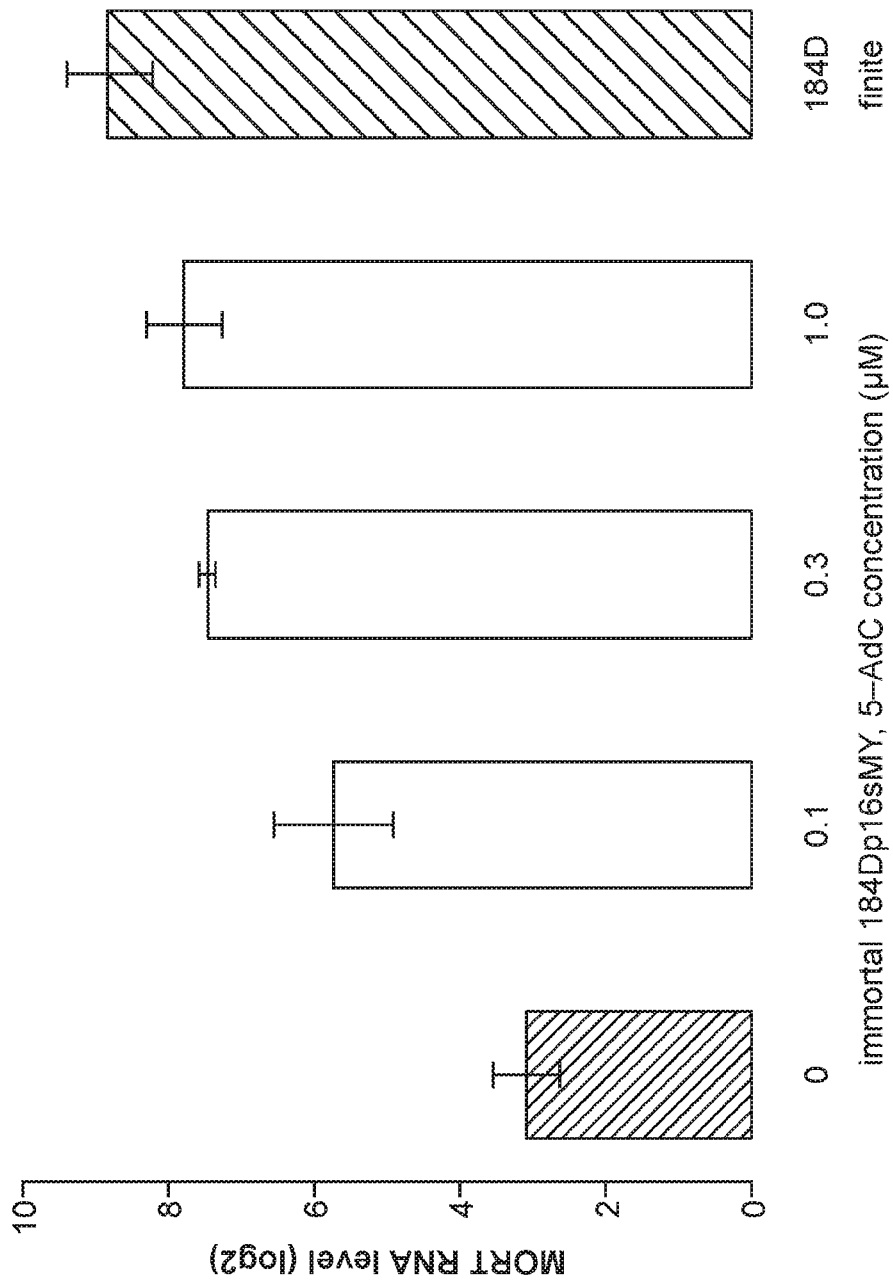
FIG. 14 is a graph showing that MORT is reactivated by 5-AdC treatment of immortalized HMEC 184Dp16SMY. The figure shows MORT transcript level in untreated 184Dp16SMY, an increased MORT level after 96 h treatment with three concentrations of 5-AdC and the MORT level in untreated finite parental 184D HMEC. The error bars show the SEM of 3 independent experiments.

To confirm that epigenetic mechanisms are functionally involved in cancer cell specific silencing of MORT, we tested whether its silencing could be reactivated by treatment with the epigenetic modifier and DNA methyltransferase inhibitor 5-aza-2'-deoxycytidine (5-AdC). The MORT-negative breast tumor lines MDA-MB231, MDA-MB453, and MCF7 (FIGS. 9 and 10) were exposed to 1 μM 5-AdC for 96 h. Each of the three tumor cell lines showed a significant decrease in the level of DNA methylation of the MORT promoter and reactivation of MORT expression after the 5-AdC treatment (FIG. 13). The treatment of immortalized MORT negative HMEC line 184Dp16sMY by 5-AdC also resulted in reactivation of MORT transcription (FIG. 14). These data further support that the silencing of MORT expression in cancer is due to the aberrant DNA methylation of its promoter.

Example 2: Reversal of Immortalization Using a MORTRNa

Figure 19A:
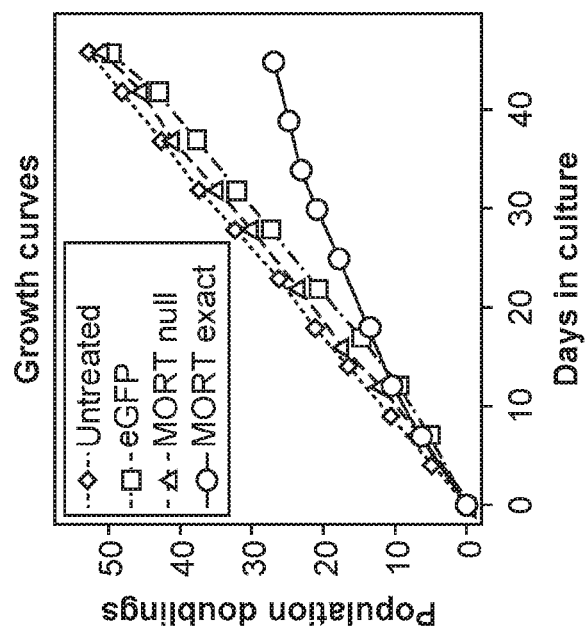
FIG. 19A, 19B depict the senescence of immortal HMEC upon restoration of MORT expression.
Figure 19B:
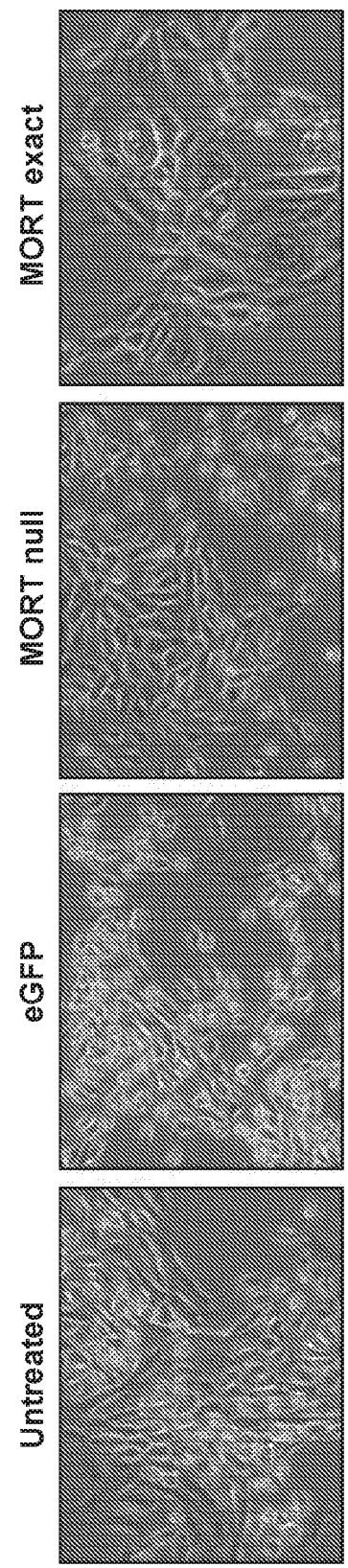

Clontech's Tet-On® 3G system was used to construct lentiviral vectors that express 1) the MORT lncRNA sequence (MORT-Exact)(SEQ ID NO:8) and 2) an aberrant MORT lncRNA to which 60 nucleotides were added at the 5' end of MORT that was predicted to disrupt RNA secondary structure rendering MORT either hypomorphic or completely nonfunctional (MORT-null). The experiments demonstrated that MORT can reverse immortalization ("remortalize") cells and induce senescence (FIG. 19). Immortal, MORT(−) 184Dp16sMY HMEC were either untreated or transduced with a lentivirus that expressed MORT-Exact, MORT-Null, or eGFP. Cells transduced with MORT-Exact cease growth and take on senescent phenotypes (FIG. 19A-19B). Specifically, MORT Exact-transduced cells: 1) express senescence-associated β-galactosidase (SA-βGal); 2) increase in size—quantitative measurements show a 1.5-fold increase in senescent MORT-Exact cells; 3) show many cells becoming multinucleated; and 4) permanently cease proliferation over time. None of these characteristics were seen in untreated control, eGFP-transduced, or MORT Null-transduced cells.

In contrast, none of these characteristics were seen in untreated control, eGFP-transduced, or MORT Null-transduced cells. qRT/PCR analysis of both experiments showed that the observed senescence was not due to induced over-expression of p16 or p14 that could overcome the p16shRNA-mediated inhibition of this pathway. Similarly, qRT/PCR analysis suggests that p53 is also not involved in this senescence, since neither p53 nor well-defined p53 target genes, MDM2, p21, PIG3, and MASPIN were induced during the MORT-mediated senescence. This result suggests that a DDR, such as would be expected from telomere dysfunction, may not be responsible for the observed senescence.

DISCUSSION

In an effort to better understand the transcriptional events associated with pathologic immortalization, we analyzed gene expression changes that arise during the controlled genetic immortalization of HMEC. This two-step model of non-clonal HMEC immortalization uses pathologically relevant genetic changes that bypass defined tumor-suppressive proliferation barriers and reproducibly create immortal, non-malignant cell lines that lack the gross genomic changes and passenger errors typically observed in tumors[1,2]. We reasoned that this model system would allow for the identification of consistent gene expression changes pertinent to epithelial cell immortalization itself.

We did not observe any consistent gene expression changes among the different HMEC strains that bypassed the initial stasis proliferation barrier through p16 inhibition or cyclin D1 overexpression. Since p16 appears to be the prime mediator of cell stasis induced by sub-optimal environmental conditions, gene expression differences between the pre-stasis cells and those that were made post-stasis by transduction with p16 shRNA prior to exposure to such sub-optimal environmental conditions, could well be expected to be minimal and variable among the different individual cell strains. With respect to the cyclin D1 over-expressing post-stasis cells, it is reasonable to predict that the overexpression of the ccnd1/CDK2 fusion gene resulting in hyperphosphorylated RB protein, as well as the likely phosphorylation of a number of other substrates, could lead to significant changes in gene expression; however, the D1 post-stasis group in our study was too small to have sufficient statistical power to decisively quantify these changes. Despite the minimal differences in gene expression between pre-stasis and post-stasis HMEC cultures, they display at least one significant behavioral difference—c-MYC can readily immortalize post-stasis HMEC, but cannot immortalize pre-stasis HMEC In contrast to p16 shRNA-mediated bypass of cell stasis, the c-MYC-mediated bypass of replicative senescence and acquisition of pathologic cell immortality resulted in significant changes in expression of hundreds of genes. Evaluation of gene ontologies that were overrepresented within the differentially expressed genes include biological processes such as cell death, apoptosis, stem cell division, and regulation of protein tyrosine kinase activity; all consistent with cellular pathways one would expect to be targeted during cellular immortalization. The gene ontology term with the most significant overrepresentation was the integrin-mediated signaling pathway, which has been long associated with human breast carcinogenesis[21-23]. A comparison of these immortality-linked genes with TCGA expression data revealed that a large fraction of these genes are also significantly altered in clinical breast cancer. The clinical breast tumor samples, when compared to normal breast tissues, will have, in addition to changes linked to immortality and malignancy, additional changes in cell type specific genes, due to comparing carcinomas of clonal origin to heterogeneous normal tissues containing many cell types. Despite that, for genes changed in the immortalization model, there was a good concordance between the in vitro model and clinical cancer. The fact that the most dramatic gene expression changes found in the in vitro model of HMEC immortalization are also seen in clinical breast cancer samples reinforces the relevance of the model for the study of breast carcinogenesis and suggests further that these gene expression changes seen in clinical cancer may very well occur early in transformation, prior to frank malignancy. Taken together these results illustrate the similarities between non-malignant and malignant immortal cell lines, and fundamental distinctions between non-malignant immortalized lines and normal, finite lifespan cells, lending further significance to the immortalization step in cancer progression[1, 28, 29].

The single gene with the greatest change in expression during the immortalization step is a long intergenic noncoding RNA with unknown function. We designated this lncRNA MORT, since it is present in all mortal human cells examined and is silenced during immortalization, and might therefore be involved in preserving cellular mortality. The MORT transcript does not have a capacity to code for ORFs longer than what happens by random chance and these ORFs do not share homology with known protein domains. The MORT transcript does not have a coding label according to CPAT[24]. The recent study that annotated nearly 60,000 human noncoding transcripts[3] included a ZNF667-AS1 transcript variant corresponding to MORT in the noncoding category.

MORT probably arose during late primate evolution, since MORT gene orthologs are only present in the genomes of higher primates. It is possible that the increased lifespan of higher primates necessitated the rise of additional mechanisms to control undesired cellular proliferation, with MORT serving such a function. The relative level of MORT expression in normal cells is moderate to low; typical, although not exclusive, to lncRNAs[25]. The second exon of the MORT transcript contains regions homologous to three repetitive elements, indicating that this part of the gene evolved from repetitive elements. The presence of repetitive elements within the exons and its recent appearance during evolution is also a typical feature of long non-coding RNAs[4, 30, 31] The noncoding nature of MORT and its exclusivity to higher primates limits the experimental models available to study MORT function, although it does not diminish its potential importance in human cellular mortality or carcinogenesis.

MORT gene silencing in transformed cells appears epigenetic in nature; we found that the loss of MORT expression was linked to aberrant DNA methylation of the MORT promoter in immortal HMEC, breast cancer cell lines, and a large fraction of the most common human cancers. Based on our studies in the HMEC system, the timing of this epigenetic dysfunction appears to be at the boundary between the mortal and immortal phenotypes. The DNA methylation level in immortalized HMEC was relatively low, although consistent between samples; much higher levels were seen in cancer cell lines or in the TCGA tumor samples. This suggests that the DNA methylation is likely a consequence, or a signature, of the MORT silencing rather than its primary cause. However, DNA methylation is likely involved in the reinforcement and maintenance of MORT silencing. The ability of 5-aza-2'-deoxycytidine to robustly reactivate MORT gene expression in both immortalized HMEC and human breast cancer cell lines underscores the functional relevance of DNA methylation in this gene's silent state. Together the timing of MORT silencing during the immortalization process and its epigenetic inactivation in 15 out of the 17 most common clinical cancers suggests MORT silencing might be involved in the early, foundational stages of human carcinogenesis.

Since MORT is expressed in all finite lifespan cells and down-regulated in many immortal cells, it likely plays an active role in maintaining the mortal state. Based on the circumstantial evidence to date, we hypothesize two complementary but distinct possible mechanisms for MORT function. It may be involved in the mechanisms that normally repress telomerase activity and telomere maintenance in finite cells, and its expression may be incompatible with an immortal state. Or MORT may be involved in mechanisms that induce cell senescence independent of telomere length, such as cell cycle components, and impose senescence under certain conditions that could otherwise lead to inappropriate cell proliferation. Our preliminary data investigating the function of MORT indicate that the MORT transcript is exported out of the nucleus and is enriched in cellular fractions containing ribosomes (unpublished data), suggesting that it might be involved in the regulation of translation of its targets. The rather long half-life of the MORT transcript indicates that the MORT RNA likely functions at steady transcript levels that do not vary during the cell cycle.

In conclusion, we have identified and characterized a lincRNA, MORT, that we found to be 1) epigenetically silenced at the immortality boundary in an experimental model of HMEC immortalization and 2) epigenetically silenced in a large majority of the most common human cancers. The temporal order of MORT loss during the in vitro arc of malignant transformation and the frequency of its aberrant silencing in clinical cancer suggests a possible important role during human carcinogenesis. Consequently, MORT may potentially represent a new target for cancer therapeutic intervention.

REFERENCES

1. Garbe J C, Vrba L, Sputova K, Fuchs L, Novak P, Brothman A R, Jackson M, Chin K, LaBarge M A, Watts G, et al. Immortalization of normal human mammary epithelial cells in two steps by direct targeting of senescence barriers does not require gross genomic alterations. Cell Cycle 2014; 13:3423-35.
2. Lee J K, Garbe J C, Vrba L, Miyano M, Futscher B W, Stampfer M R, LaBarge M A. Age and the means of bypassing stasis influence the intrinsic subtype of immortalized human mammary epithelial cells. Front Cell Dev Biol 2015; 3:13.
3. Iyer M K, Niknafs Y S, Malik R, Singhal U, Sahu A, Hosono Y, Barrette T R, Prensner J R, Evans J R, Zhao S, et al. The landscape of long noncoding RNAs in the human transcriptome. Nat Genet 2015; 47:199-208.
4. Ulitsky I, Bartel D P. lincRNAs: genomics, evolution, and mechanisms. Cell 2013; 154:26-46.
5. Keniry A, Oxley D, Monnier P, Kyba M, Dandolo L, Smits G, Reik W. The H19 lincRNA is a developmental reservoir of miR-675 that suppresses growth and Igf1r. Nature cell biology 2012; 14:659-65.

6. Cech T R, Steitz J A. The noncoding RNA revolution-trashing old rules to forge new ones. Cell 2014; 157:77-94.
7. Brannan C I, Dees E C, Ingram R S, Tilghman S M. The product of the H19 gene may function as an RNA. Mol Cell Biol 1990; 10:28-36.
8. Rinn J L, Chang H Y. Genome regulation by long noncoding RNAs. Annu Rev Biochem 2012; 81:145-66.
9. Penny G D, Kay G F, Sheardown S A, Rastan S, Brockdorff N. Requirement for Xist in X chromosome inactivation. Nature 1996; 379:131-7.
10. Gendrel A V, Heard E. Noncoding RNAs and epigenetic mechanisms during X-chromosome inactivation. Annu Rev Cell Dev Biol2014; 30:561-80.
11. Heard E, Chaumeil J, Masui O, Okamoto I. Mammalian X-chromosome inactivation: an epigenetics paradigm. Cold Spring Harbor symposia on quantitative biology 2004; 69:89-102.
12. Lee Jeannie T, Bartolomei Marisa S. X-Inactivation, Imprinting, and Long Noncoding RNAs in Health and Disease. Cell 2013; 152:1308-23.
13. Vincent-Salomon A, Ganem-Elbaz C, Manie E, Raynal V, Sastre-Garau X, Stoppa-Lyonnet D, Stern M H, Heard E. X inactive-specific transcript RNA coating and genetic instability of the X chromosome in BRCA1 breast tumors. Cancer Res 2007; 67:5134-40.
14. Engreitz J M, Pandya-Jones A, McDonel P, Shishkin A, Sirokman K, Surka C, Kadri S, Xing J, Goren A, Lander E S, et al. The Xist lncRNA exploits three-dimensional genome architecture to spread across the X chromosome. Science 2013; 341:1237973.
15. Rinn J L, Kertesz M, Wang J K, Squazzo S L, Xu X, Brugmann S A, Goodnough L H, Helms J A, Farnham P J, Segal E, et al. Functional demarcation of active and silent chromatin domains in human HOX loci by noncoding RNAs. Cell 2007; 129:1311-23.
16. Esteller M. Non-coding RNAs in human disease. Nat Rev Genet 2011; 12:861-74.
17. Ling H, Vincent K, Pichler M, Fodde R, Berindan-Neagoe I, Slack F J, Calin G A. Junk DNA and the long non-coding RNA twist in cancer genetics. Oncogene 2015.
18. Mitra S A, Mitra A P, Triche T J. A central role for long non-coding RNA in cancer. Front Genet 2012; 3:17.
19. Gupta R A, Shah N, Wang K C, Kim J, Horlings H M, Wong D J, Tsai M C, Hung T, Argani P, Rinn J L, et al. Long non-coding RNA HOTAIR reprograms chromatin state to promote cancer metastasis. Nature 2010; 464:1071-6.
20. Ji P, Diederichs S, Wang W, Boing S, Metzger R, Schneider P M, Tidow N, Brandt B, Buerger H, Bulk E, et al. MALAT-1, a novel noncoding RNA, and thymosin beta4 predict metastasis and survival in early-stage non-small cell lung cancer. Oncogene 2003; 22:8031-41.
21. Pontier S M, Muller W J. Integrins in mammary-stem-cell biology and breast-cancer progression—a role in cancer stem cells? Journal of cell science 2009; 122:207-14.
22. Mizejewski G J. Role of integrins in cancer: survey of expression patterns. Proc Soc Exp Biol Med 1999; 222:124-38.
23. Hynes R O. Integrins: Bidirectional, Allosteric Signaling Machines. Cell 2002; 110:673-87.
24. Wang L, Park H J, Dasari S, Wang S, Kocher J P, Li W. CPAT: Coding-Potential Assessment Tool using an alignment-free logistic regression model. Nucleic Acids Res 2013; 41:e74.
25. Derrien T, Johnson R, Bussotti G, Tanzer A, Djebali S, Tilgner H, Guernec G, Martin D, Merkel A, Knowles D G, et al. The GENCODE v7 catalog of human long noncoding RNAs: Analysis of their gene structure, evolution, and expression. Genome research 2012; 22:1775-89.
26. Barretina J, Caponigro G, Stransky N, Venkatesan K, Margolin A A, Kim S, Wilson C J, Lehar J, Kryukov G V, Sonkin D, et al. The Cancer Cell Line Encyclopedia enables predictive modelling of anticancer drug sensitivity. Nature 2012; 483:603-7.
27. American Cancer Society. Cancer Facts & FIGS. 2015. In: Society AC, ed.
Atlanta: American Cancer Society, 2015.
28. Li Y, Pan J, Li J L, Lee J H, Tunkey C, Saraf K, Garbe J C, Whitley M Z, Jelinsky S A, Stampfer M R, et al. Transcriptional changes associated with breast cancer occur as normal human mammary epithelial cells overcome senescence barriers and become immortalized. Mol Cancer 2007; 6:7.
29. Stampfer M R, LaBarge M A, Garbe J C. An Integrated Human Mammary Epithelial Cell Culture System for Studying Carcinogenesis and Aging. In: Schatten H, ed. Cell and Molecular Biology of Breast Cancer. New York: Springer Science+Business Media, 2013:323-61.
30. Hezroni H, Koppstein D, Schwartz M G, Avrutin A, Bartel D P, Ulitsky I. Principles of long noncoding RNA evolution derived from direct comparison of transcriptomes in 17 species. Cell Rep 2015; 11:1110-22.
31. Kapusta A, Kronenberg Z, Lynch V J, Zhuo X, Ramsay L, Bourque G, Yandell M, Feschotte C. Transposable elements are major contributors to the origin, diversification, and regulation of vertebrate long noncoding RNAs. PLoS Genet 2013; 9:e1003470.
32. Garbe J C, Bhattacharya S, Merchant B, Bassett E, Swisshelm K, Feiler H S, Wyrobek A J, Stampfer M R. Molecular distinctions between stasis and telomere attrition senescence barriers shown by long-term culture of normal human mammary epithelial cells. Cancer Res 2009; 69:7557-68.
33. Oshiro M M, Watts G S, Wozniak R J, Junk D J, Munoz-Rodriguez J L, Domann F E, Futscher B W. Mutant p53 and aberrant cytosine methylation cooperate to silence gene expression. Oncogene 2003; 22:3624-34.
34. Rice J C, Massey-Brown K S, Futscher B W. Aberrant methylation of the BRCA1 CpG island promoter is associated with decreased BRCA1 mRNA in sporadic breast cancer cells. Oncogene 1998; 17:1807-12.
35. R_Development_Core_Team. R: A Language and Environment for Statistical Computing. Vienna, Austria: R Foundation for Statistical Computing, 2015.
36. Carvalho B, Bengtsson H, Speed T P, Irizarry R A. Exploration, normalization, and genotype calls of high-density oligonucleotide SNP array data. Biostatistics 2007; 8:485-99.
37. Smyth G K. Limma: linear models for microarray data. In: Gentleman R C V, Huber W, Irizarry R, Dudoit S, ed. Bioinformatics and Computational Biology Solutions using R and Bioconductor. New York: Springer, 2005:397-420.
38. Falcon S, Gentleman R. Using GOstats to test gene lists for GO term association. Bioinformatics 2007; 23:257-8.
39. Dinger M E, Pang K C, Mercer T R, Mattick J S. Differentiating protein-coding and noncoding RNA: challenges and ambiguities. PLoS Comput Biol 2008; 4:e1000176.

40. Novak P, Jensen T J, Garbe J C, Stampfer M R, Futscher B W. Stepwise DNA methylation changes are linked to escape from defined proliferation barriers and mammary epithelial cell immortalization. Cancer Res 2009; 69:5251-8.
41. Vrba L, Junk D J, Novak P, Futscher B W. p53 induces distinct epigenetic states at its direct target promoters. BMC Genomics 2008; 9:486.
42. Trapnell C, Pachter L, Salzberg S L. TopHat: discovering splice junctions with RNA-Seq. Bioinformatics 2009; 25:1105-11.
43. Li H, Handsaker B, Wysoker A, Fennell T, Ruan J, Homer N, Marth G, Abecasis G, Durbin R. The Sequence Alignment/Map format and SAMtools. Bioinformatics 2009; 25:2078-9.
44. Law C W, Chen Y, Shi W, Smyth G K. voom: Precision weights unlock linear model analysis tools for RNA-seq read counts. Genome Biol 2014; 15:R29.
45. Yang E, van Nimwegen E, Zavolan M, Rajewsky N, Schroeder M, Magnasco M, Darnell J E, Jr. 2003. Decay rates of human mRNAs: correlation with functional characteristics and sequence attributes. Genome Res 13(8): 1863-1872.

Notwithstanding the appended clauses, the disclosure set forth herein is also defined by the following clauses:

1. A nucleic acid encoding a ribonucleic acid (RNA) comprising the ribonucleotide sequence set forth in SEQ ID NO:7, or a variant RNA thereof that confers a mortal phenotype.
2. The nucleic acid of Clause 1, operably linked to a promoter.
3. The nucleic acid of Clause 2, wherein the promoter is a heterologous promoter.
4. An expression vector comprising the nucleic acid of any one of Clauses 1 to 3.
5. An RNA encoded by the nucleic acid of Clause 1.
6. The RNA of Clause 5, wherein the RNA is transcribed from:
   the nucleic acid of any one of Clauses 1 to 3; or
   the expression vector of Clause 4.
7. A liposome, comprising:
   the nucleic acid of any one of Clauses 1 to 3;
   the expression vector of Clause 4; or
   the RNA of Clause 5 or Clause 6.
8. A recombinant cell comprising:
   the nucleic acid of any one of Clauses 1 to 3;
   the expression vector of Clause 4; or
   the RNA of Clause 5 or Clause 6.
9. The recombinant cell of Clause 8, wherein the cell is present in a container.
10. The recombinant cell of Clause 8, wherein the cell is present in a subject.
11. The recombinant cell of Clause 10, wherein the subject has been identified as having a disease or disorder associated with cell immortalization.
12. A pharmaceutical composition, comprising:
    the nucleic acid of any one of Clauses 1 to 3,
    the expression vector of Clause 4,
    the RNA of Clause 5 or Clause 6,
    the liposome of Clause 7, or
    the recombinant cell of Clause 8; and
    a pharmaceutically acceptable carrier.
13. A method, comprising:
    quantifying a level of a MORT RNA in a biological sample obtained from a subject.
14. The method according to Clause 13, wherein the quantifying is performed by quantitative reverse transcription polymerase chain reaction (qRT-PCR).
15. The method according to Clause 13, wherein the quantifying is performed by next-generation sequencing, microarray analysis, RNAse protection assay, northern blot analysis, or fluorescence in situ hybridization (FISH).
16. The method according to any one of Clauses 13 to 15, wherein the biological sample is a fluid sample.
17. The method according to any one of Clauses 13 to 15, wherein the biological sample is a tissue sample.
18. The method according to Clause 17, wherein the tissue sample is a premalignant lesion.
19. The method according to Clause 18, wherein the premalignant lesion is a ductal carcinoma in situ (DCIS) lesion.
20. The method according to any one of Clauses 13 to 19, further comprising, prior to the quantifying, obtaining the biological sample from the subject.
21. The method according to any one of Clauses 13 to 20, further comprising identifying the subject as having a disease or disorder associated with cell immortalization when the quantified level of the MORT RNA is below a threshold level.
22. The method according to Clause 21, further comprising treating the disease or disorder associated with cell immortalization by administering to the subject a therapeutically effective amount of a pharmaceutical composition.
23. The method according to Clause 22, wherein the pharmaceutical composition is the pharmaceutical composition of Clause 12.
24. A method, comprising:
    determining the methylation status of the MORT promoter in a biological sample obtained from a subject.
25. A method for reversing immortalization in a cell, comprising:
    introducing into an immortalized cell:
    the nucleic acid of any one of Clauses 1 to 3;
    the expression vector of Clause 4; or
    the RNA of Clause 5 or Clause 6.
26. A method for immortalizing a cell, comprising:
    introducing into a non-immortalized cell an agent that reduces MORT RNA levels in the cell.
27. The method according to Clause 26, wherein the agent is a MORT small interfering RNA (siRNA).

The above examples are provided to illustrate the invention but not to limit its scope. Other variants of the invention will be readily apparent to one of ordinary skill in the art and are encompassed by the appended claims. All publications, accession numbers, databases, and patents cited herein are hereby incorporated by reference in their entireties for all purposes.

What is claimed is:

1. A complementary deoxyribonucleotide (cDNA) that encodes a ribonucleic acid (RNA) comprising the ribonucleotide sequence set forth in SEQ ID NO:7, or a variant RNA thereof comprising 99% or greater identity to, and across the entire length of, the ribonucleotide sequence set forth in SEQ ID NO:7 that confers a mortal phenotype, wherein the cDNA is operably linked to an RNA polymerase promoter.

2. An expression vector comprising the cDNA of claim 1.

3. A liposome, comprising the cDNA of claim 1.

4. A recombinant cell comprising the cDNA of claim 1, wherein the cell is present in a container.

5. A pharmaceutical composition, comprising the cDNA of claim 1.

6. A method for reversing immortalization in a cell, comprising:
introducing into an immortalized cell the cDNA of claim 1.

* * * * *